United States Patent
Bocan et al.

(12) 
(10) Patent No.: US 6,340,709 B1
(45) Date of Patent: Jan. 22, 2002

(54) USE OF MATRIX METALLOPROTEINASE INHIBITORS FOR TREATING NEUROLOGICAL DISORDERS AND PROMOTING WOUND HEALING

(75) Inventors: Thomas Michael Andrew Bocan; Peter Alan Boxer, both of Ann Arbor; Joseph Thomas Peterson, Jr., Brighton; Denis Schrier, Ann Arbor; Andrew David White, Pinckney, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/269,123

(22) PCT Filed: Nov. 21, 1997

(86) PCT No.: PCT/US97/21532

§ 371 Date: Mar. 19, 1999

§ 102(e) Date: Mar. 19, 1999

(87) PCT Pub. No.: WO98/26773

PCT Pub. Date: Jun. 25, 1998

Related U.S. Application Data

(60) Provisional application No. 60/032,753, filed on Dec. 17, 1996.

(51) Int. Cl.[7] ............................................... A61K 31/18
(52) U.S. Cl. ........................ 514/602; 514/600; 514/601
(58) Field of Search .............................. 514/600, 601, 514/602

(56) References Cited

U.S. PATENT DOCUMENTS 3,784,701 A    1/1974    Tomcufcik et al. ......... 424/317

FOREIGN PATENT DOCUMENTS

| EP | 0606046 A1 | 7/1994 |
|---|---|---|
| WO | 95/07695 | 3/1995 |
| WO | 96/11209 | 4/1996 |
| WO | 96/15096 | 5/1996 |
| WO | 96/38434 | 12/1996 |
| WO | 97/19068 | 5/1997 |
| WO | 97/23459 | 7/1997 |
| WO | 97/44315 | 11/1997 |

OTHER PUBLICATIONS

Beeley, N.R.A., et al. *Current Opinion In Therapeutic Patents*, Inhibitors Of Matrix Metalloproteinases (MMP's), vol. 4, No. 1, 1994, pp. 7–16, XP002043031.

Beckett, R.P., et al., *Drug Discovery Today*, Recent Advances In Matrix Metalloproteinase Inhibitor Research, vol. 1, No. 1, 1996, pp. 16–26, XP002043033.

Morphy, J.R., et al., *Current Medicnal Chemistry*, Matrix Metalloproteinase Inhibitors: Current Status, vol. 2, 1995, pp. 743–762, XP002043028.

PCT International Search Report, PCT/US97/21532.

*Primary Examiner*—Zohreh Fay
(74) *Attorney, Agent, or Firm*—Charles W. Ashbrook; David R. Kurlandsky

(57) ABSTRACT

This invention provides a method for treating and preventing neurological disorder such as Alzheimer's disease, and for promoting wound healing comprising administering a compound characterized as being a matrix metalloproteinase inhibitor.

8 Claims, No Drawings

USE OF MATRIX METALLOPROTEINASE INHIBITORS FOR TREATING NEUROLOGICAL DISORDERS AND PROMOTING WOUND HEALING

This application is a 371 of PCT/US97/21532 filed on Nov. 21, 1997.

FIELD OF THE INVENTION

This invention provides a method for treating and preventing neurological disorders such as Alzheimer's disease, and for promoting wound healing, comprising administering a compound characterized as being a matrix metalloproteinase inhibitor.

BACKGROUND OF THE INVENTION

Amyloid plaque formation is found in a number of diseases, including Alzheimer's disease, scrapie, bovine spongiform encephalophy, Gerstmann-Straussler Syndrome, and the like. The amyloid plaques comprise proteins bound together in a fibrillous matrix. Amyloidosis is the general name given to diseases and conditions characterized by the presence of amyloid protein. A number of different types of amyloid protein are known, and all types are considered pathological, since no normally occurring amyloids are known. Accordingly, the presence of amyloid protein in a host is an indication of abnormal formation of fibrils and plaques. Amyloidosis has been clinically observed in a number of disease states, including certain mental illnesses, neurological diseases, and collagenosis. Indeed, the brains of subjects diagnosed with Alzheimer's disease have one thing in common, namely an abundance of amyloid in the form of plaques and tangles.

Alzheimer's disease is a degenerative brain disorder characterized clinically by progressive loss of memory, cognition, reasoning, judgment, and emotional stability that gradually leads to mental deterioration and ultimately death. Only two clinically approved treatments are available, one being tacrine hydrochloride (Cognex®, from the Parke-Davis Division of Warner-Lambert Company). Because Alzheimer's disease and related degenerative brain disorders are a major medical issue for an aging population, the need for new treatments and methods for diagnosing the disorders are needed.

We have now discovered that compounds which inhibit the enzymes that mediate the breakdown of connective tissues are useful for treating neurological disorders and wound healing. Such enzymes are known as native matrix metalloproteinases, which are classes of naturally occurring enzymes found in most mammals. They are zinc proteases that hydrolyze collagens, proteoglycans, and glycoproteins. The classes include gelatinase A and B, stromelysin-1 and -2, fibroblast collagenase, neutrophil collagenase, matrilysin, metalloelastase, and interstitial collagenase. These enzymes are implicated with a number of diseases which result from breakdown of connective tissues, such as rheumatoid arthritis, osteoarthritis, osteoporosis, multiple sclerosis, and even tumor metastasis. To date, inhibitors of matrix metalloproteinases have not been utilized to treat or prevent neurological disorders such as Alzheimer's disease and Parkinson's disease, or to promote wound healing. An object of this invention is to provide a method for treating and preventing neurological disorders and promoting wound healing metalloproteinase inhibitor.

SUMMARY OF THE INVENTION

This invention provides a method of treating and preventing neurological disorders and promoting wound healing by administering an effective amount of a matrix metalloproteinase inhibitor.

The method can be practiced by administering any chemical compound that is effective in inhibiting the biological activity of a matrix metalloproteinase such as collagenase, stromelysin, gelatinase or elastase. Numerous compounds are known to be matrix metalloproteinase inhibitors, and any of such compounds can be utilized in the method of this invention.

In a preferred embodiment, the matrix metalloproteinase inhibitor to be utilized is a substituted bicyclic compound of the formula

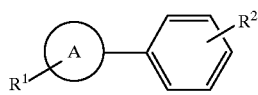

wherein:

A is phenyl or

where

Y is CH or N;

$R^1$ is a substituent such as alkyl, aryl, halo, amino, substituted and disubstituted amino, and alkoxy;

$R^2$ is carboxyalkyl ketone or oxime, or a carboxyalkyl sulfonamide such as

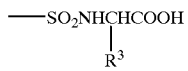

where $R^3$ is alkyl, substituted alkyl, amino, substituted and disubstituted amino, and aryl.

A particularly preferred embodiment is a method of treating and preventing neurological disorders and wound healing by administering a biphenylsulfonamide such as

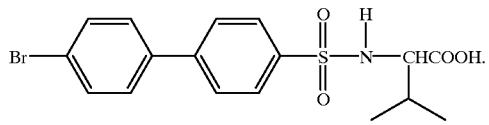

In another embodiment, neurological disorders and wound healing are treated or prevented by administering a matrix metalloproteinase which is a substituted fused tricyclic compound of the formula

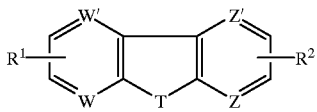

where $R^1$ and $R^2$ are as defined above, T is O, $S_5$ $(O)_{0,1}$, or 2, C=O, $NR^3$, or

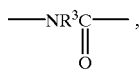

and W, $W^1$, Z, and $Z^1$ are each the same or different and each is $CR^3$, where $R^3$ is alkyl, halo, alkoxy, acyl, and aryl. A preferred method utilizes dibenzofurans of the above formula, for instance compounds such as

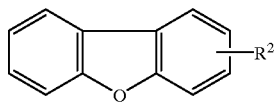

where $R^2$ is, for instance,

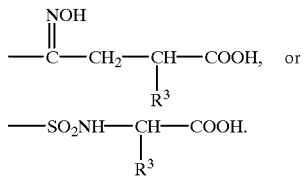

All of the matrix metalloproteinase inhibitors to be utilized in the method of this invention are either known or are readily available by common synthetic processes.

DETAILED DESCRIPTION OF THE INVENTION

All that is required to practice this invention is to administer to a mammal suffering from a neurological disorder or suspected of developing a neurological disorder or in need of wound healing an effective amount of a matrix metalloproteinase inhibitor.

A "matrix metalloproteinase inhibitor" as used herein is any chemical compound that inhibits by at least five percent the hydrolytic activity of at least one matrix metalloproteinase enzyme that is naturally occurring in a mammal. Such compounds are also referred to as "MMP inhibitors". Numerous matrix metalloproteinase inhibitors are known, and all are useful in the method of this invention. For example, 4-biarylbutyric and 5-biarylpentanoic acid derivatives are described in WO 96/15096, which is incorporated herein by reference. The compounds are defined generally as $(T)_xA$—B—D—E—G. Over 400 specific compounds are named, and each is incorporated herein and can be employed in this invention.

The matrix metalloproteinases (MMPs) (Table 1) represent a zinc dependent subset of the protease enzymes. MMP dependent remodeling of the extracellular matrix has been implicated in a variety of human diseases, but is also involved in normal tissue turnover and development. Activity of compounds results from binding to the enzymes in various pockets, such as the P1' pocket and the P3' pocket.

MMP compounds in clinical development include batimastat (2) for the treatment of malignant pleural effusion, and marimastat (1) for the treatment of pancreatic cancer. Galardin (3) is for the treatment of corneal ulcers, and a specific MMP-1 inhibitor is RO 31-9790 (4).

Compounds in Clinical Development

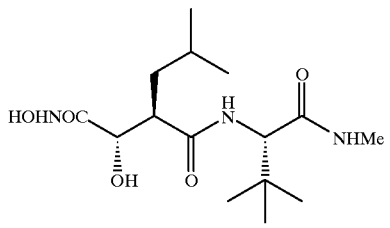

(1)

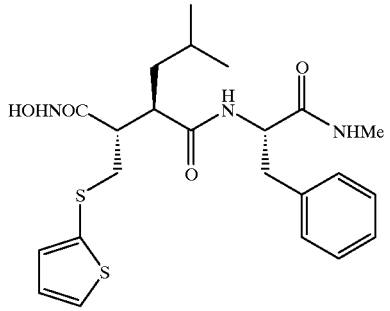

(2)

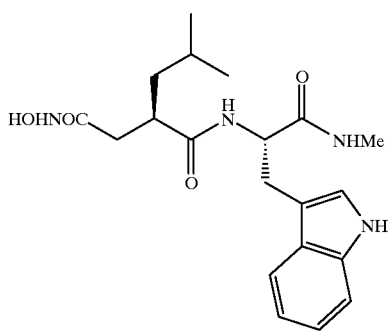

(3)

(4)

TABLE 1

| MMP-Nomenclature | |
|---|---|
| MMP-1 | collagenase-1 (interstitial) |
| MMP-2 | gelatinase A (72kD) |
| MMP-3 | Stromelysin-1 |
| MMP-7 | Matrilysin (PUMP) |
| MMP-8 | Neutrophil Collagenase |
| MMP-9 | Gelatinase B (92kD) |
| MMP-10 | Stromelysin-2 |
| MMP-11 | Stromelysin-3 |
| MMP-12 | metalloelastase |
| MMP-13 | Collagenase-3 |
| MMP-14 | MT1-MMP, Membrane-type 1 |
| MMP-15 | MT2-MMP, Membrane-type 2 |
| MMP-16 | MT3-MMP, Membrane-type 3 |
| MMP-17 | MT4-MMP, Membrane-type 4 |

Succinamides

The majority of the MMP inhibitors with the succinic acid template are potent and nonselective, particularly with a hydroxamate zinc binding group. However, it is possible to achieve selectivity with this moiety (Table 2). The series of compounds (5–10) are potent against MMP-8, and certain examples (9,10) are very potent inhibitors of MMP-9. Selectivity for MMP-3 and MMP-1 can be obtained in this series with the P-1 ligand. The alcohol (5) is selective for MMP-1 over MMP-3. The amides (6, 7) and benzyl ether (8) are selective for MMP-3 over MMP-1. Compound (9) is a potent inhibitor of MMPs 1, 3, 8, and 9. Selectivity for MMP-2 and MMP-3 can be obtained over MMP-1 and MMP-7, when the P1' substituent is a long chain alkyl group (11), in a related series with a carboxylate zinc ligand. The selectivity can be explained by pocket size. Further exquisite selectivity for MMP-2 can be obtained when the chain length is extended. The compound (12) is very selective for MMP-2 over MMP-1, 3, and 7.

Selective Succinate MMP Inhibitors

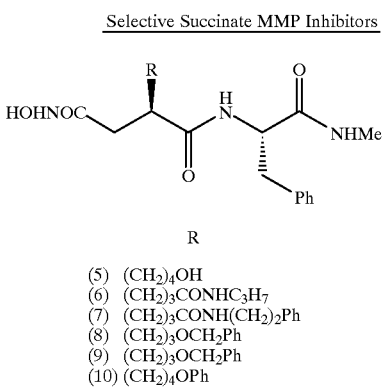

R (5) $(CH_2)_4OH$
(6) $(CH_2)_3CONHC_3H_7$
(7) $(CH_2)_3CONH(CH_2)_2Ph$
(8) $(CH_2)_3OCH_2Ph$
(9) $(CH_2)_3OCH_2Ph$
(10) $(CH_2)_4OPh$

TABLE 2

MMP Selectivity

| Cpd | R = P1' Group | MMP-1 IC$_{50}$ ($\mu$M) | MMP-2 IC$_{50}$ ($\mu$M) | MMP-3 IC$_{50}$ ($\mu$M) | MMP-7 IC$_{50}$ ($\mu$M) | MMP-8 IC$_{50}$ ($\mu$M) | MMP-9 IC$_{50}$ ($\mu$M) |
|---|---|---|---|---|---|---|---|
| 5 | $(CH_2)_4OH$ | 0.064 | | 2.2 | | 0.007 | |
| 6 | $(CH_2)_3CONHC_3H_7$ | 5.1 | | 0.36 | | 0.002 | |
| 7 | $(CH_2)_3CONH(CH_2)_2Ph$ | 1.3 | | 0.006 | | 0.032 | |
| 8 | $(CH_2)_3OCH_2Ph$ | 2.27 | | 0.043 | | <0.001 | |
| 9 | $(CH_2)_4OPh$ | 0.008 | | 0.028 | | <0.002 | |
| 10 | $(CH_2)_5Oph$ | 0.026 | | 0.014 | | 0.002 | 0.00031 |
| 11 | $C_{12}H_{25}$ | 30% @ 100 $\mu$M | 0.5 | 1 | 10% @ 100 $\mu$M | | |
| 12 | $C_{16}H_{33}$ | IA | 0.03 | 10% @ 100 $\mu$M | 20% @ 100 $\mu$M | | |
| 13 | i-Bu | 0.03 | | 3 | | | |
| 14 | i-Bu | 0.01 | 0.7 | 0.008 | | | |
| 15 | i-Bu | 3.5 | | 0.32 | 0.07 | | |
| 16 | —$(CH_2)_5$— | 0.48 | | 5.9 | 0.003 | | |
| 17 | $(CH_2)_3Ph$ | 0.203 | 0.000062 | 0.0083 | | | |
| 18 | $(CH_2)_3Ph$-4 Cl | 0.385 | <0.00001 | | | | 0.000016 |
| 19 | $(CH_2)_3Ph$-4 Me | 22 | 0.001 | 0.47 | | | |
| 20 | $(CH_2)_3Ph$-4 Me | 48 | 0.0009 | 0.38 | | | |
| 21 | i-Bu | 0.1 | 0.2 | 9 | 3 | 0.4 | |
| 22 | | 0.0000025 | 0.0018 | 0.023 | | | |
| 23 | i-Bu | 0.0084 | | 0.0014 | 0.00014 | | |
| 24 | $C_8H_{17}$ | >10 | 0.34 | 0.57 | | | |
| 25 | $(CH_2)_2Ph$-4-$C_3H_7$ | 5.9 | 0.0035 | 0.018 | | | |
| 26 | $(CH_2)_2Ph$-4-$C_3H_7$ | >10 | 0.310 | 0.068 | | | |
| 27 | $(CH_2)_2Ph$ | 0.72 | 0.086 | 0.008 | | | |
| 28 | i-Bu | 0.02 | | 0.091 | | | 0.005 |
| 29 | i-Bu | 0.054 | | 1.4 | | | 0.007 |
| 30 | i-Bu | 0.16 | >10 | | | | 0.035 |
| 31 | i-Bu | 0.056 | 0.178 | | | | 0.074 |
| 32 | $(CH_2)_2Ph$-4-$C_3H_7$ | >10 | 0.0057 | 0.000036 | | | |
| 33 | $NHCOCF_3$ | 0.040 | | | | >1 | |
| 34 | $NHCOCH_3$ | >100 | | | | | |
| 35 | $NHCO(CH_2)_2Ph$ | 3.5 | | | | 0.038 | |
| 36 | NHCObenzotriazole | 0.008 | | | | | 0.024 |
| 37 | $(CH_2)_3Ph$-4 Me | 17 | 0.0025 | 0.277 | | | |
| 38 | $(CH_2)_2Ph$ | >10 | 0.02 | 0.0014 | | | |
| 39 | i-Bu | 0.0176 | | 0.239 | | | |
| 40 | | 0.38 | | 0.017 | | | |
| 43 | | | 0.014 | 0.017 | | 3.2 | |
| 44 | | | 0.00091 | 0.0057 | | 0.0015 | |

IA = inactive

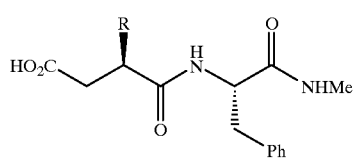
R
(11) C₁₂H₂₅
(12) C₁₆H₃₃
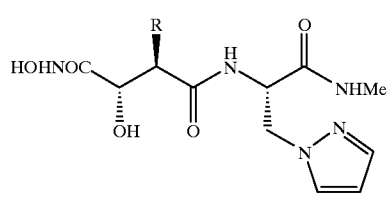
R
(13) $^t$Bu
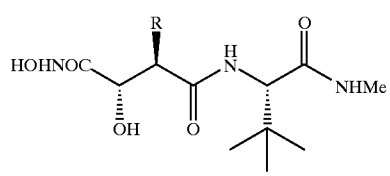
R
(14) $^t$Bu
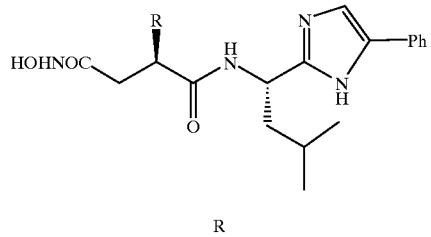
R
(15) $^t$Bu
(16) —(CH₂)₅—
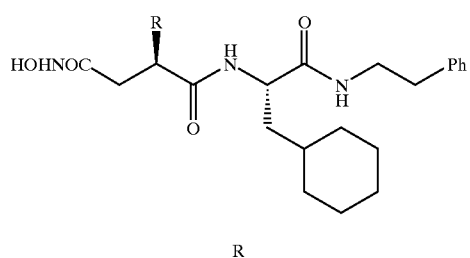
R
(17) (CH₂)₃Ph
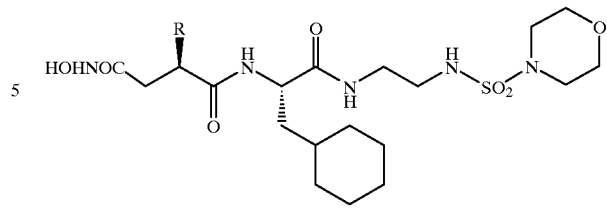
R
(18) (CH₂)₃Ph-4-Cl
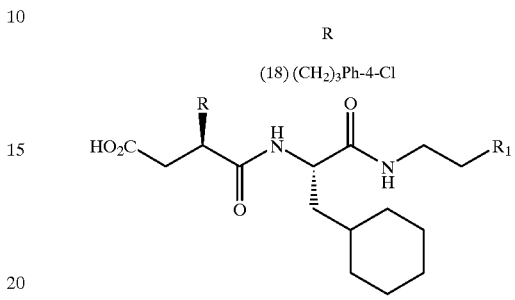
| R | R₁ |
|---|---|
| (19) (CH₂)₃Ph-4-Me | Ph |
| (20) (CH₂)₃Ph-4-Me | PhSO₂NH₂ |
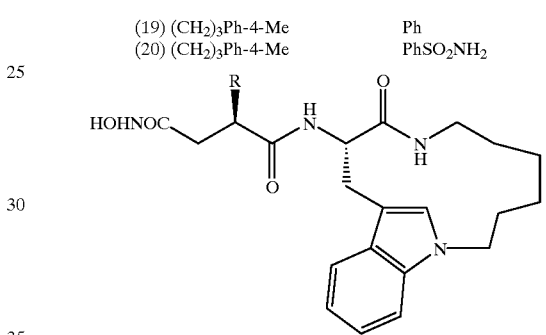
R
(21) $^t$Bu
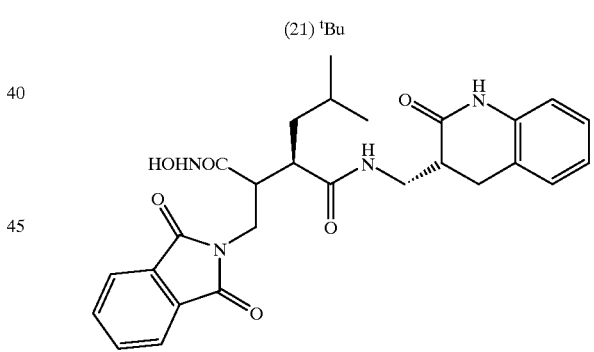
(22)
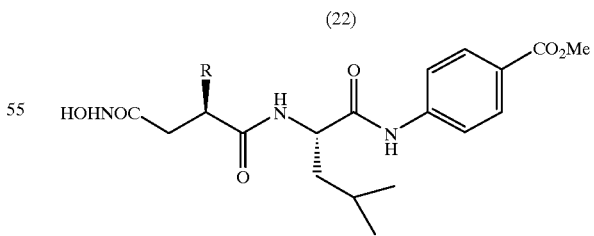
R
(23) $^t$Bu The combination of a small P1' ligand and a pyrazyl-N-methyl/N-methyl amide at P2–P3' affords 100-fold selectivity for MMP-1 over MMP-3 (13). With tert-butyl at P2' selectivity for MMP-1 and 3 over MMP-2 is obtained with N—Me amides at P3' (14). MMP-2 potency is restored with P3' N-phenyl substituents. Compounds selective for MMP-7 over MMP-1 and 3 have been obtained with a bulky P3' substituent and a small P1' substituent (15). MMP-7 and MMP-1 selectivity can be attenuated with cyclohexyl at P1' (16).

Compounds with 100-fold selectivity for MMP-2 over 3- and 10,000-fold selectivity for MMP-2 over one have been reported by Celltech (17). A compound (18) from this series also potently inhibits MMP-13. The corresponding carboxylates (19,20) also retain this specificity profile. These compounds all contain a cyclohexyl at P2' and a phenethyl amide, or sulfonamide at P3'.

Modest selectivity for MMPs 1, 2, and 8 over MMP-3 and 7 can be obtained with the analog constrained in the P2'-P3' region (21).

Significant selectivity for MMP-1 over MMP-2 and 3 is observed with the quinolone analog (22). These compounds probably bind the same way as compound (33), in which the hetero amide group is postulated to occupy P1' via a conformational expansion of the P1' pocket.

Modest selectivity for MMP-7 over MMP-1 and 3 is obtained with substituted phenyl amides at P3' (23).

α-Aminocarboxylates

α-Aminocarboxylates are potent MMP inhibitors. A long chain substituent at P1' yields selectivity for MMP-3 and 2 over MMP-1, with a methyl group at P1 (24). A phenethyl moiety substituted para with small alkyl groups also affords compounds that are MMP-3 and 2 selective versus MMP-1 (25, 26). Interestingly, selectivity of 100-fold for MMP-3 over -1 and 10-fold over MMP-2 can be achieved with a phthalimidobutyl group at P1 (27). A related series of aminocarboxylates developed at Glaxo have selectivity for MMP-1 and 9 over MMP-3. These compounds contain large extended napthalimide groups on the nonprime side. Selectivity over MMP-3 can be attenuated by substitution in the napthalimide ring (28,29). A variety of amino acid replacements were tolerated at P2' by MMP-1 and -9 but good activity for MMP-3 was only found with an aryl side chain. Selectivity for MMP-3 could also be obtained with a non-peptoid substituent at P2'. Phenethyl substitution eliminates MMP-3 activity while benzoic acid substitution retains it (30,31).

In the related glutamic acids, selectivity for MMP-3 and 2 over MMP-1 is achieved with 4-alkylphenethyl substituents at P1' (32).

Phosphorus/Sulfur Containing Compounds

An intriguing series of compounds in terms of selectivity was published by Glaxo in which an acetamide functionality was postulated to occupy P1'. The thiol compound (33) showed selectivity for MMP-1 over 9 as a result of favorable interactions of the trifluoroacetamide in P1'. The corresponding acetamide (34) did not inhibit MMP-1 presumably as it lacks the capacity to form a fluorine-hydrogen bond. Increased bulk with the phenylethyl amide (35) reversed the selectivity for MMP-9 over MMP-1. However the benzotriazole (36) which would not be expected to fit in P1' of MMP-1 was an MMP-1 inhibitor. This observation has been reported with phenylethers in P1', where it was postulated that arg 214 swings out of the way and allows a δ—δ stack between an electron rich phenolic ring and an electron deficient guanidinium ring. A conformational adjustment has been reported recently in the P2'–P3' region to accommodate hydrophobic inhibitors of MMP-3 and crystal structures of matrilysin have shown the P1' pocket can expand to accommodate large hydrophobic P1' substituents. This enzyme flexibility is not surprising given that several of the MMP enzymes can cleave many different natural substrates.

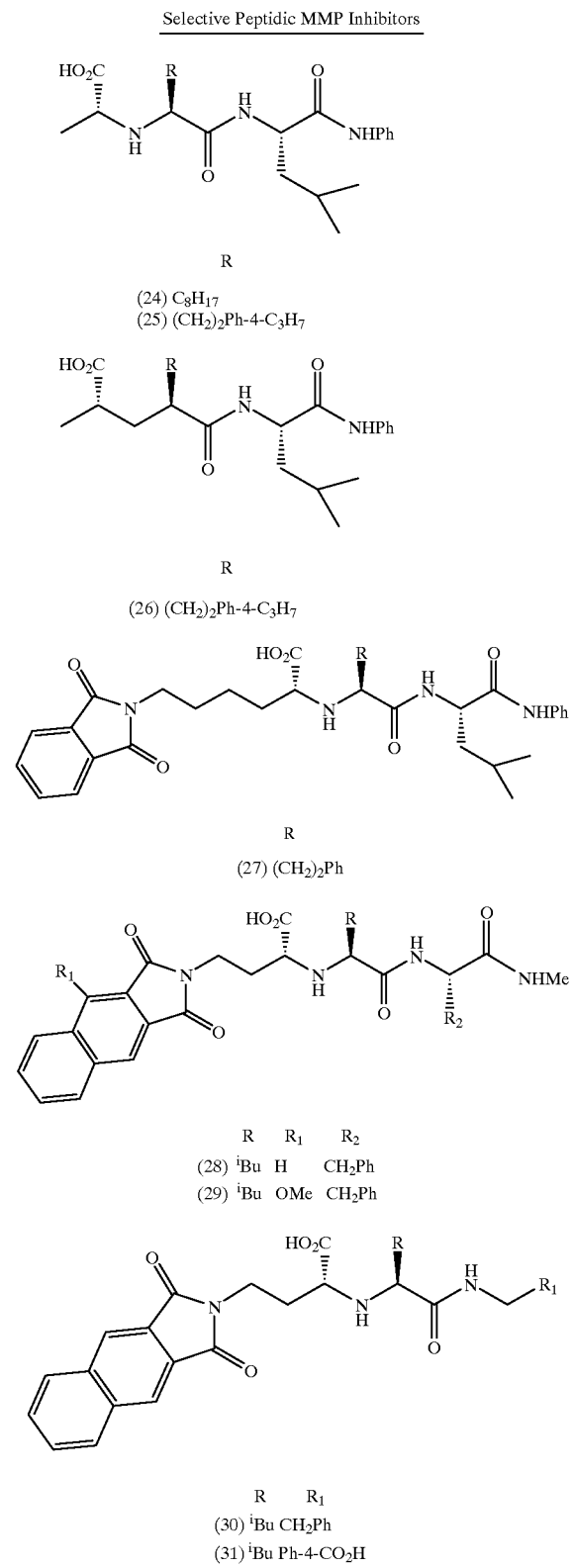

Selective Peptidic MMP Inhibitors

R
(24) C$_8$H$_{17}$
(25) (CH$_2$)$_2$Ph-4-C$_3$H$_7$

R
(26) (CH$_2$)$_2$Ph-4-C$_3$H$_7$

R
(27) (CH$_2$)$_2$Ph

| R | R$_1$ | R$_2$ |
|---|---|---|
| (28) $^i$Bu | H | CH$_2$Ph |
| (29) $^i$Bu | OMe | CH$_2$Ph |

R   R$_1$
(30) $^i$Bu  CH$_2$Ph
(31) $^i$Bu  Ph-4-CO$_2$H

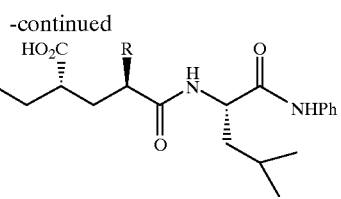

(32) (CH₂)₂Ph-4-C₃H₇

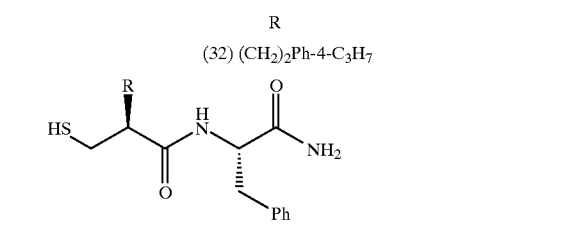

(33) NHCOCF₃
(34) NHCOMe
(35) NHCO(CH₂)₂Ph
(36) NHCO-[benzotriazole]

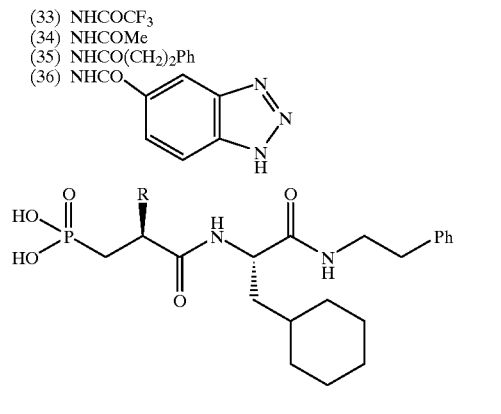

R
(37) (CH₂)₃Ph-4-Me

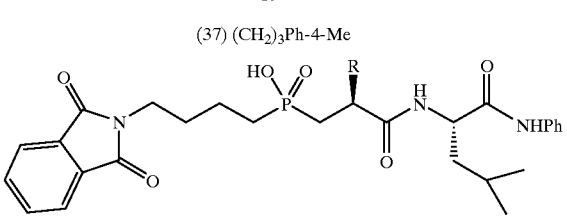

R
(38) (CH₂)₂Ph

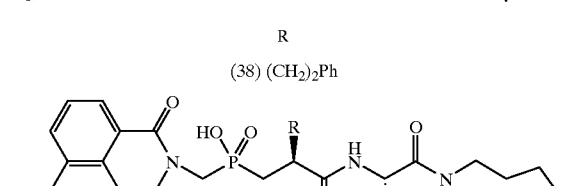

R
(39) ⁱBu

The phosphinic acid (37) mirrors the MMP-2 selectivity over MMP-1 and 3 found with the analogous succinamide. This selectivity can be reversed for compound (38) with a P1 substituent and N-phenyl amide at P3'. Bulky P1 substituents and a constrained P2'–P3' region as exemplified in (39), give rise to MMP-1 selectivity over MMP-3.

Nonpeptidic Inhibitors

Ciba Geigy disclosed a series of aryl sulfonamides of which CGS27023A (40) shows a 20-fold selectivity for MMP-3 over MMP-1. In vivo the compound blocks proteoglycan break down when dosed orally at 30 mg/kg in rabbits injected with stromelysin and is effective in the guinea pig model of osteoarthritis. Related sulfonamides (41) have been disclosed by British Biotech in which the aryl group has been replaced by a long alkyl chain and Pfizer have replaced the picolinyl group with a methylene amide functionality (42). Bayer has disclosed a series of aryl succinic acids in which the usual 2 amino acid residues have been replaced by an aryl moiety. Compounds with phenylalkyl substituents alpha to the acid (43) inhibit MMP-3 and MMP-2 selectively over MMP-9. Inhibition of MMP-9 can also be obtained with a phthalimidoalkyl group a to the carboxylic acid (44). This MMP-9 profile is similar to that observed with α-aminocarboxylates (28–31), thus the phthalimido group presumably occupies the non-prime side. Both compounds (43,44) were active in the guinea pig model of osteoarthritis. In both of these series as with the peptidic SAR most of the activity resides in one stereoisomer suggesting a similar mode of binding. Constrained analogues around the zinc binding region do not increase potency. In vivo, compound (44) was antimetastatic in both a tail vein metastasis model and in a spontaneous metastasis model. Both 43 and 44 were effective in the guinea pig model of osteoarthritis inhibiting femoral lesions 37.8 and 53% respectively.

Derivatives of futoenone, exemplified by compound 45 have been shown to weakly inhibit MMPs 1, 3, and 9, with modest selectivity for MMP-3. These compounds are thought to bind on the non-prime side (by overlap modeling with Galardin).

Tetracycline antibiotics, exemplified by aranciamycin (46), are weak inhibitors of MMPs. The MMP activity has been distinguished from antibiotic activity yielding submicromolar MMP-1 inhibitors with the monosaccharide ring deleted (47). Anthracene carboxylic acids (48) have also been reported as MMP-1 inhibitors suggesting the tetracycline D-ring is not needed for MMP activity.

Coumarin derivatives (49) have been shown to be weak inhibitors of MMP-1.

The recent crystallographic publications have provided exquisite insight into the mode of action of peptidic inhibitors with the MMPs. The real situation is more complex than the X-ray/homology models would suggest. It has been noted that the P1' pockets of the enzymes MMP-3 and MMP-7 are flexible and can breath or change conformation. This is not surprising given that these enzymes, particularly MMP-3 can degrade many natural substrates. Peptidic inhibitors pick up 2 hydrogen bonds per amide, and conformationally these dominate along with Zn coordination. In the case of nonpeptoid inhibitors or simplified peptides which have the propensity to interact hydrophobically, the enzyme may be more accommodating not being constrained in a rigid peptide H-bond framework. Hydrophobic effects would also be amplified with a weaker zinc binding group. Thus expanding the P1' pocket or changing conformation to take advantage of hydrophobic interactions, seems more likely with a nonpeptidic inhibitor and may possibly give rise to unique selectivities not observed with peptidic inhibitors.

Non-Peptidic MMP Inhibitors

(40) 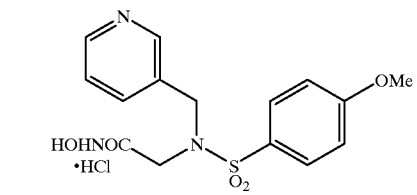

(41) 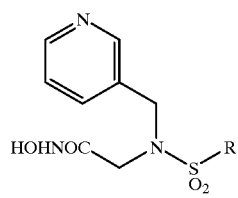

(42) 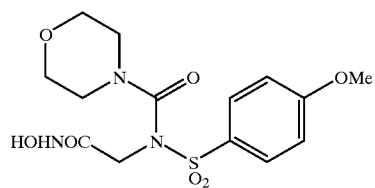

(43) 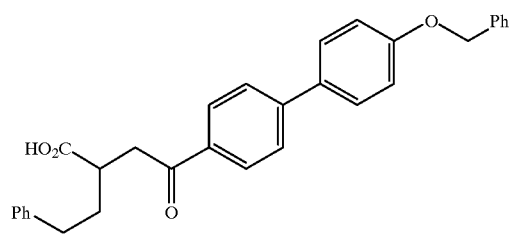

(44) 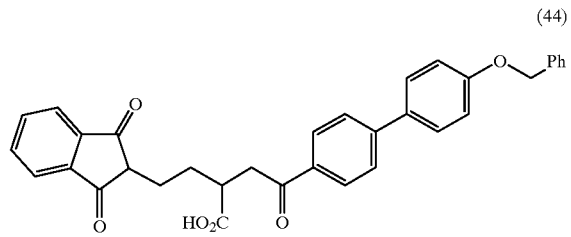

(45) 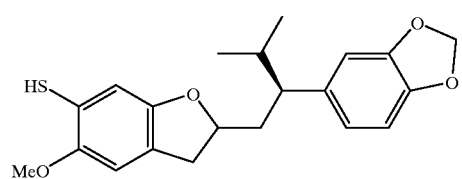

(46) 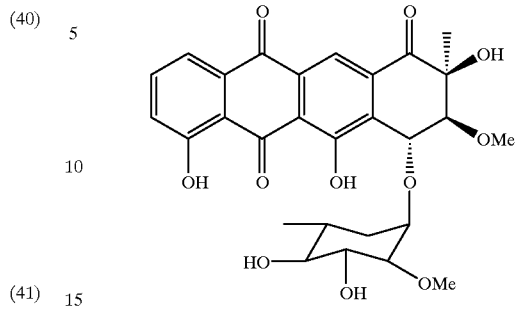

(47) 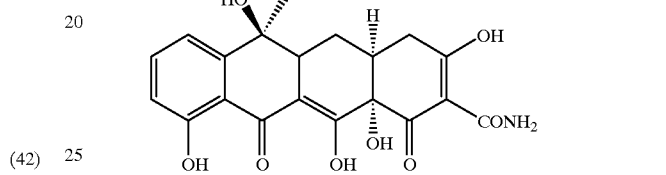

(48) 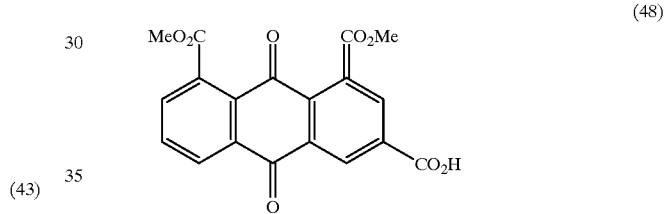

(49) 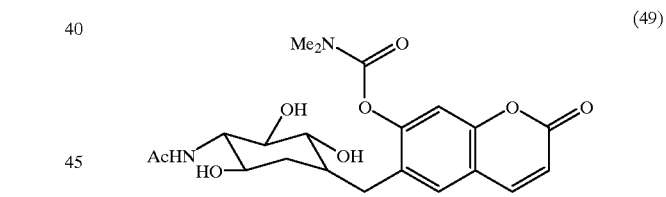

Matrix Metalloproteinases in Neurological Disorders

Inflammatory diseases can affect the central nervous system (brain and spinal cord); the best characterized of such disorders are multiple sclerosis (MS) and various forms of meningitis and encephalitis. A common feature of these diseases is a breakdown of the blood-brain barrier (BBB) followed by inflammatory perivascular infiltration and eventual demyelination and astrogliosis. MMPs play a key role in allowing inflammatory cells access to the CNS. Both MMP-2 and MMP-9 are found in the CSF of patients with MS and MMP-9 immunoreactivity can be detected in active MS lesions. Similarly, using zymography increased levels of MMP-9 can be found in the cerebrospinal fluid (CSF) of animals with experimental autoinimmnune encephalitis (EAE). In this commonly used animal model of neuroinflammatory diseases animals are immunized with myelin basic protein or the active epitope of this protein. Further stimulation with pertussis toxin or other endotoxin produces behavioral symptomology ranging from limp tails to complete paralysis. Most animals and humans can be shown to have activated T cells which recognize MBP and other proteins in the myelin sheath, but these cells do not appear to cross the BBB. Direct evidence that MMPs can degrade the BBB and allow infiltration of T cells comes from studies in which MMP-2 has been injected directly in the brain of experimental animals.

The most convincing evidence for the involvement of MMPs in contributing to the breakdown of the BBB and the ensuing inflammation is the ability of hydroxamate inhibitors of MMPs to reduce the clinical symptomology of EAE. Both galardin (GM 6001) and RO 31-9790 have been examined in models of EAE and found to prevent and/or delay the clinical signs. It is clear that the actions of these drugs is occurring after the induction of T cells, since RO 31-9790 has also been shown to protect in a model of adoptively transferred EAE from MBP-sensitized splenocytes. In addition to the role of MMPs in contributing to the breakdown of the BBB there is good evidence that MMPs can also directly degrade myelin basic protein leading to the demyelination characteristic of MS. Using MMPs expressed in Chinese hamster ovary cells, it has been demonstrated that MMP-2 has the greatest activity at digesting MBP, but MMP-9 has also been shown to degrade MBP in an EAE model. This indicates that MMPs play a critical role in two key processes in the pathophysiology of MS; namely breakdown of the BBB and demyelination. This provides a strong rationale for the development of systemically active inhibitors of MMP-2 and/or MMP-9 in the treatment of multiple sclerosis.

MMPs also play a role in other neurological disorders, which are not generally considered to be inflammatory in nature. For example, MMPs are probably responsible for the opening of the BBB in focal ischemia and hemorrhagic brain injury leading to secondary injury from vasogenic edema. In post mortem tissue from Alzheimer's diseased brain both MMP-2 and MMP-9 have been detected and using zymography the activity of MMP-9 was approximately 4-fold that seen in control brains. â-Amyloid is a potent stimulator of both MMP-2 and MMP-9 in cortical cultures and TIMP staining was found to co-distribute with neuritic lesions and the amyloid precursor protein in Alzheimer's brains. Increased amounts of MMP-9 were also observed in the motor cortex, thoracic, and lumbar cord regions of patients suffering from amyotrophic lateral sclerosis. Taken together these results suggest that MMPs may play a more general role in the degradation of the extracellular matrix in a variety of chronic neurodegenerative disorders.

Wound Healing

Wound healing is characterized by the biosynthesis of normal connective tissue composed of appropriate extracellular and vascular organization and function. This process is dynamic and involves the closely regulated remodeling of ECM by MMPs. Regardless of the wound site, the balance between MMP activity and their endogenous inhibitors is responsible for the establishment of a stable extracellular matrix architecture. However, MMP profiles vary depending on the nature of the injury, wound site, and species. Proteolytic activity within the wound environment is also an important determinant of wound chronicity. In general, excess MMP activity is observed in chronic wounds. Moreover, wound fluid obtained from chronic wounds contains elevated levels of vitronectin and fibronectin degradation products. Factors specific to each class of wound are described below.

Acute Healing Wounds

Collagenase activity is critical for the turnover and restructuring of matrix components during wound repair, and this process appears to be critical for cell movement in the extracellular matrix. Elevation of collagenolytic activity has been reported in association with wound healing. Many cell types have the potential to produce interstitial collagenase, including fibroblasts, macrophages, endothelial cells and neutrophils. Keratinocytes have collagenolytic activity when cultured on certain matrices and in migrating cells during the early phase at the wounds edge. Disruption of the basement membrane appears to be a primary stimulus for induction of MMP-1 expression in keratinocytes. In in vitro systems, keratinocytes migrating on collagen express enhanced collagenolytic activity, whereas contact with laminin does not stimulate collagenolysis. In normal skin, keratinocytes are in contact with laminin and thus are not exposed to collagen. The consistent finding of MMP-1 expression in wound edge epithelium and its close association with keratinocyte migration and re-epithelialization suggest a distinct and temporal role for MMP-1 in wound healing. It appears that MMP-1 contributes to the efficient healing of acute wounds. Indeed, external sources of MMP-1 have been used as a therapeutic approach to promote wound healing.

MMP-2 and 9 are present in healing wounds. The expression of MMP-2 is stable during the first week in healing wounds, with an apparent peak at 4–6 days. The same time at which collagenolytic influences in the wound diminish. Latent and multiple active forms of the active enzyme are present in wound fluid with the two lowest molecular weight forms appearing toward the end of the first week. This temporal sequence is consistent with the appearance of fibroblasts and a decline in macrophages in the wound site. The fibroblasts accumulate near newly formed capillary loops where cell division and deposition of fibrillar collagen occur. Collagen remodeling is a prominent feature during this period and capillaries appear in the wound along with the fibroblasts. Capillary endothelial cells are also a potential source of MMP-2. MMP-9 has also been observed in wound tissues and fluids during the earliest phases of wound repair. MMP-9 is expressed by infiltrating neutrophils, granulation tissue, a few basal layers of the migrating epithelial sheet and in basal layers in the non wounded area. Most of the enzyme is found in its latent form. However, active enzyme is also present in most instances.

An important consideration regarding the involvement of MMPs in wound healing is the level of endogenous inhibitor present during the healing process. Several studies have shown that the MMP inhibitory activity increases rapidly during the wound healing process. The levels generally reach a peak within the first few days and decline thereafter. Presumably, high levels are required during the early phase of wound healing to temper remodeling during a period of matrix deposition.

Chronic Wounds

Compared with acute wound fluid, total but inactive levels of collagenases are higher in chronic ulcers. Analyzed by immunoblotting/western, immunoreactivities for MMP-1 and MMP-8 are both present. Studies with the MMP-1 inhibitor doxycycline suggest that the dominant enzyme appears to be of the MMP-1 type. Although MMP-1 plays an important role in wound healing, only a few matrix proteins, primarily types 1 and 3 collagen, are cleaved by the enzyme in a wound healing environment.

In order for cleavage of other connective tissue components, including laminin, fibronectin, type IV collagen and glycosaminoglycans, additional proteinase activity is required. MMP-3 and stromelysin-2 (MMP-10) are other metalloproteinases involved in proteolysis and tissue remodeling. MMP-3 is prominently expressed by dermal cells and keratinocytes within chronic wounds. In the dermis, fibroblasts are a major source of the enzyme. In the epidermis, basal cells which are distal to the wound edge, and distinct from those cells producing MMP-1 produce MMP-3. It is likely that the cells which express MMP-3 are those which proliferate and become migrating cells, suggesting that these keratinocytes have distinct roles in tissue remodeling. Because both normal keratinocytes (which do not express MMP-3), and MMP-3 positive keratinocytes are found in contact with basement membrane, the stimulus for enzyme expression is probably due to an interaction with a soluble factor. Stromelysin-2 also has a unique pattern of expression in wound healing and is produced by basal keratinocytes at the leading edge of the migrating cells (the same cells which make MMP-1). In contrast with MMP-3, however, a signal for stromelysin-2 is not detected within the dermis. Because stromelysin-2 and MMP-1 are expressed in keratinocytes at the migrating front, contact with the dermal matrix (e.g. collagen) may stimulate release of both enzymes. In addition, stromelysin-2 is not expressed in cells attached to the basement membrane, suggesting that altered cell matrix interactions may stimulate its expression.

Although gelatinase levels are elevated in acute wounds, these enzymes are found in much greater quantities in chronic wounds and ulcers. The levels of MMP-2 are approximately 3–5 fold elevated in chronic wounds, and MMP-9 levels are 5- to 25-fold higher. In addition the local gelatinase profile is not common to all patients and the profiles are much more complex than in acute wound fluid. Several smaller molecular weight bands are detectable in chronic wound fluid consistent with cleavage to smaller activated forms.

The distinct localization of MMP-1, MMP-3 and stromelysin-2 in chronic wounds suggest that the enzymes have different functions. In the dermis, MMP-1 and MMP-3 and the gelatinases affect tissue repair at multiple stages, including remodeling during the formation and removal of granulation tissue and the resolution of scar tissue. In the epidermis, MMP-1 appears to promote keratinocyte migration and promote remodeling of dermal connective tissue. Stromelysin-2 may also facilitate keratinocyte migration by degrading non-collagenous matrix or by removing damaged basement membrane. Stromelysin-2 activates secreted pro-collagenase but it is unclear whether the enzyme performs this function in vivo. MMP-3 may be useful for restructuring the newly formed basement membrane. Although the over production of MMPs may contribute to wound chronicity, it is also clear that the activity of these enzymes is ultimately beneficial. Therefore, strategies developed for the treatment of chronic wounds with MMP inhibitors must be carefully focused to moderate those mechanisms which prevent healing. The reduction of TIMP-1 and TIMP-2 levels observed in chronic wounds, however, suggests that it might be productive to restore the balance of inhibitory and degradative influences within a chronic wound.

This invention thus provides a method for treating neurological disorders and promoting wound healing by administering an effective amount of an MMP inhibitor. Especially preferred compounds to be utilized include the following:

[1,1'-Biphenyl]-4-butanoic acid, 4'-chloro-α-(2-methylpropyl)-γ-oxo;
[1,1'-Biphenyl]-4-butanoic acid, 4'-chloro-α-(2-methylpropyl)-γ-oxo-, (S)-;
[1,1'-Biphenyl]-4-butanoic acid, 4'-chloro-α-(2-methylpropyl)-γ-oxo-, (R)-;
[1,1'-Biphenyl]-4-butanoic acid, 4'-chloro-β-(2-methylpropyl)-γ-oxo-, (S);
[1,1'-Biphenyl]-4-butanoic acid, 4'-chloro-β-(2-methylpropyl)-γ-oxo-, (R)-;
[1,1'-Biphenyl]-4-butanoic acid, 4'-chloro-γ-oxo-;
[1,1'-Biphenyl]-4-butanoic acid, 4'-bromo-γ-oxo-;
[1,1'-Biphenyl]-4-butanoic acid, 4'-fluoro-γ-oxo-;
[1,1'-Biphenyl]-4-butanoic acid, 2'-fluoro-γ-oxo-;
[1,1'-Biphenyl]-4-butanoic acid, 2'-chloro-γ-oxo-;
[1,1'-Biphenyl]-4-butanoic acid, 2',4'-difluoro-pl)-oxo-;
[1,1'-Biphenyl]-4-butanoic acid, 3'-chloro-γ-oxo-;
[1,1'-Biphenyl]-4-butanoic acid, α-(2-methyl-propyl)-γ-oxo-;
[1,1'-Biphenyl]-4-butanoic acid, 4'-bromo-α-(2-methylpropyl)-γ-oxo-;
[1,1'-Biphenyl]-4-butanoic acid, 4'-fluoro-α-(2-methylpropyl)-γ-oxo-;
[1,1'-Biphenyl]-4-butanoic acid, 4'-ethyl-α-(2-methylpropyl)-γ-oxo-;
[1,1'-Biphenyl]-4-butanoic acid, 2'-fluoro-α-(2-methylpropyl)-γ-oxo-;
[1,1'-Biphenyl]-4-butanoic acid, 2'-chloro-α-(2-methylpropyl)-γ-oxo-;
[1,1'-Biphenyl]-4-butanoic acid, 4'-methoxy-α-(2-methylpropyl)-γ-oxo-;
[1,1'-Biphenyl]-4-butanoic acid, 2',4'-difluoro-α-(2-methylpropyl)-γ-oxo-;
[1,1'-Biphenyl]-4-butanoic acid, 4'-methyl-α-(2-methylpropyl)-γ-oxo-;
[1,1'-Biphenyl]-4-butanoic acid, α-(2-methyl-propyl)-γ-oxo-4'-pentyl-;
[1,1'-Biphenyl]-4-butanoic acid, 4'-chloro-α-methylene-γ-oxo-;
[1,1'-Biphenyl]-4-butanoic acid, 2'-chloro-α-methylene-γ-oxo-;
[1,1'-Biphenyl]-4-butanoic acid, 4'-chloro-α-methyl-γ-oxo-;
[1,1'-Biphenyl]-4-butanoic acid, 4'-chloro-γ-oxo-α-pentyl-;
Benzenebutanoic acid, 4-chloro-α-(2-methylpropyl)-γ-oxo-;
Benzenebutanoic acid, 4-methyl-α-methylene-γ-oxo-;
2-Butenoic acid, 4-(4'-chloro[1,1'-biphenyl]-4-yl)-4-oxo-, (E)-;
2-Butenoic acid, 4-[4-(4-chlorophenyoxy)-phenyl]-4-oxo, (E)-;
[1,1'-Biphenyl]-4-butanoic acid, 4'-hydroxy-α-(2-methylpropyl)-γ-oxo-;
[1,1'-Biphenyl]-4-butanoic acid, 4'-chloro-β-methylene-γ-oxo-;
[1,1'-Biphenyl]-4-butanoic acid, 4'-chloro-γ-hydroxy-α-(2-methylpropyl)-;
[1,1'-Biphenyl]-4-butanoic acid, 4'-chloro-γ-hydroxy-α-(2-methylpropyl)-;
2(3H)-Furanone, 5-(4'-chloro[1,1'-biphenyl]-4-yl)dihydro-3-(2-methylpropyl)-;
2(3H)-Furanone, 5-(4'-chloro[1,1'-biphenyl]-4-yl)dihydro-3-(2-methylpropyl)-;
[1,1'-Biphenyl]-4-butanoic acid, 3',4'-dichloro-γ-oxo-α-(3-phenylpropyl)-;
[1,1'-Biphenyl]-4-butanoic acid, 3',5'-dichloro-γ-oxo-α-(3-phenylpropyl)-;
[1,1'-Biphenyl]-4-butanoic acid, 4'-(acetyloxy)-γ-oxo-o-(3-phenylpropyl)-;
Benzenepentanoic acid, α-[2-[4-(5-chloro-2-thienyl)phenyl]-2-oxoethyl]-;
2-Furancarboxylic acid, 5-[4-(3-carboxy-1-oxo-6-phenylhexyl)phenyl]-;
Benzenepentanoic acid, α-[2-oxo-2-[4-(3-pyridinyl)phenyl]ethyl]-;
Benzenepentanoic acid, α-[2-oxo-2-[4-[6-(pentyloxy)-3-piridinyl]phenyl]ethyl]-;

[1,1'-Biphenyl]-4-butanoic acid, γ-oxo-4'-(pentylthio)-α-(3-phenylpropyl)-;
[1,1'-Biphenyl]-4-butanoic acid, 4'-methoxy-γ-oxo-α-(3-phenylpropyl)-;
[1,1'-Biphenyl]-4-butanoic acid, 3'-chloro-4'-fluoro-γ-oxo-α-(3-phenylpropyl)-;
[1,1'-Biphenyl]-4-butanoic acid, 4'-ethoxy-γ-oxo-α-(3-phenylpropyl)-;
Benzenepentanoic acid, α-[2-oxo-2-[4-(3-thienyl)phenyl]ethyl]-;
[1,1'-Biphenyl]-4-butanoic acid, 2',4'-dichloro-γ-oxo-α(3-phenylpropyl)-;
[1,1'-Biphenyl]-4-butanoic acid, 4'-formyl-γ-oxo-α-(3-phenylpropyl)-;
[1,1'-Biphenyl]-4-butanoic acid, γ-oxo-α-(3-phenylpropyl)-3',5'-bis(trifluoromethyl)-;
Benzenepentanoic acid, α-[2-oxo-2-[4-(2-thienyl)phenyl]ethyl]-;
[1,1'-Biphenyl]-4-butanoic acid, γ-oxo-α-(3-phenylpropyl)-3'-(trifluoromethyl)-;
[1,1'-Biphenyl]-4-butanoic acid, 2'-formyl-γ-oxo-α-(3-phenylpropyl)-;
[1,1'-Biphenyl]-4-butanoic acid, 4-hydroxy-γ-oxo-α-(3-phenylpropyl)-;
[1,1'-Biphenyl]-4-butanoic acid, γ-oxo-α-(3-phenylpropyl)-4'-propoxy-;
[1,1'-Biphenyl]-4-butanoic acid, γ-oxo-4'-(pentyloxy)-α-(3-phenylpropyl)-;
[1,1'-Biphenyl]-4-butanoic acid, γ-oxo-4'-(pentyloxy)-α-(3-phenylpropyl)-, (S)-;
[1,1'-Biphenyl]-4-butanoic acid, γ-oxo-4'-(pentyloxy)-α-(3-phenylpropyl)-, (S)-;
[1,1'-Biphenyl]-4-butanoic acid, 4'-(hexyloxy)-γ-oxo-α-(3-phenylpropyl)-;
[1,1'-Biphenyl]-4-butanoic acid, 4'-butoxy-γ-oxo-α-(3-phenylpropyl)-;
[1,1'-Biphenyl]-4-butanoic acid, γ-oxo-4'-(3-phenylpropoxy)-α-(3-phenylpropyl)-;
[1,1'-Biphenyl]-4-butanoic acid, 4'-(1-methylethoxy)-γ-oxo-α-(3-phenylpropyl)-;
[1,1'-Biphenyl]-4-butanoic acid, 4'-(heptyloxy)-γ-oxo-α-(3-phenylpropyl)-;
[1,1'-Biphenyl]-4-butanoic acid, 4'-(cyclohexyl-methoxy)-γ-oxo-α-(3-phenylpropyl)-;
[1,1'-Biphenyl]-4-butanoic acid, 4'-(2-methyl-propoxy)-γ-oxo-α-(3-phenylpropyl)-;
[1,1'-Biphenyl]-4-butanoic acid, γ-oxo-α-(3-phenylpropyl)-4'-(2-propenyloxy)-;
[1,1'-Biphenyl]-4-butanoic acid, 4'-chloro-α-heptyl-γ-oxo-;
[1,1'-Biphenyl]-4-butanoic acid, 4'-chloro-α-decyl-γ-oxo-;
[1,1'-Biphenyl]-4-butanoic acid, 4'-nitro-γ-oxo-α-(2-phenylethyl)-;
[1,1'-Biphenyl]-4-butanoic acid, 4'-cyano-γ-oxo-α-(2-phenylethyl)-;
[1,1'-Biphenyl]-4-butanoic acid, 4'-chloro-α-[2-(2-iodophenyl)ethyl]-γ-oxo-;
[1,1'-Biphenyl]-4-butanoic acid, 4'-chloro-α-[2-(3-iodophenyl)ethyl]-γ-oxo-;
[1,1'-Biphenyl]-4-butanoic acid, 4'-chloro-α-[2-(4-iodophenyl)ethyl]-γ-oxo-;
[1,1'-Biphenyl]-4-butanoic acid, 4'-chloro-α-[2-(3,5-dimethoxyphenyl)ethyl]-γ-oxo-;
[1,1'-Biphenyl]-4-butanoic acid, 4'-chloro-γ-oxo-α-phenyl-;
[1,1'-Biphenyl]-4-butanoic acid, 4'-chloro-γ-oxo-α-(phenylmethyl)-;
[1,1'-Biphenyl]-4-butanoic acid, 4'-chloro-γ-oxo-α-(2-phenylethyl)-;
[1,1'-Biphenyl]-4-butanoic acid, 4'-chloro-γ-oxo-α-[(trimethylsilyl)methyl]-;
[1,1'-Biphenyl]-4-butanoic acid, 4'-bromo-γ-oxo-α-(3-phenylpropyl)-;
[1,1'-Biphenyl]-4-butanoic acid, -γ-oxo-α-(3-phenylpropyl)-;
[1,1'-Biphenyl]-4-butanoic acid, 4'-amino-γ-oxo-α-(2-phenylethyl)-;
[1,1'-Biphenyl]-4-butanoic acid, γ-oxo-α-(2-phenylethyl)-4'-[[(phenylmethoxy)carbonyl]amino]-;
[1,1'-Biphenyl]-4-butanoic acid, 4'-[[(1,1-dimethylethoxy)carbonyl]amino]-γ-oxo-α-(2-phenylethyl)-;
[1,1'-Biphenyl]-4-butanoic acid, 4'-(acetylamino)γ-oxo-α-(2-phenylethyl)-;
[1,1'-Biphenyl]-4-butanoic acid, γ-oxo-4'-[(1-oxopentyl)amino]-α-(2-phenylethyl)-;
[1,1'-Biphenyl]-4-butanoic acid, 4'-[(3,3-dimethyl-1-oxobutyl)amino]-γ-oxo-γ-(2-phenylethyl)-;
[1,1'-Biphenyl]-4-butanoic acid, 4'-chloro-α-[2-[2-(methoxycarbonyl)phenyl]ethyl]-γ-oxo-;
[1,1'-Biphenyl]-4-butanoic acid, α-[2-(2-carboxyphenyl)ethyl]-4'-chloro-γ-oxo-;
[1,1'-Biphenyl]-4-butanoic acid, 4'-chloro-α-[2-[2-[(diethylamino)carbonyl]phenyl]ethyl]-γ-oxo-;
[1,1'-Biphenyl]-4-butanoic acid, 4'-chloro-α-[2-[3-[(diethylamino)carbonyl]phenyl]ethyl]-γ-oxo-, (S)-;
[1,1'-Biphenyl]-4-butanoic acid, 4'-chloro-α-[2-[3-[(diethylamino)carbonyl]phenyl]ethyl]-γ-oxo-, (R)-;
Cyclopentanecarboxylic acid, 2-[(4'-chloro[1,1'-biphenyl]-4-yl)carbonyl]-5-[(phenylmethoxy)methyl]-, (1α,2β,5β)-;
Cyclopentanecarboxylic acid, 2-[(4'-chloro[1,1'-biphenyl]-4-yl)carbonyl]-5-(phenoxymethyl)-, (1α,2β,5β)-;
Cyclopentanecarboxylic acid, 2-[(benzoyloxy)-methyl]-5-[(4'-chloro[1,1'-biphenyl]-4-yl)carbonyl]-, (1α,2β,5β)-;
1,2-Benzenedicarboxylic acid, 1-[[2-carboxy-3-[(4'-chloro[1,1'-biphenyl]-4-yl)carbonyl]cyclopentyl]-methyl]-2-methyl ester,(1α,2β,3β)-;
Cyclopentanecarboxylic acid, 2-[(4'-chloro[1,1'-biphenyl]-4-yl)carbonyl]-5-[(2-thienylthio)methyl]-, (1α,2β,5β)-;
Cyclopentanecarboxylic acid, 2-[(benzoylamino)methyl]-5-[(4'-chloro [1,1'-biphenyl]-4-yl)carbonyl]-, (1α,2β,5β)-;
Cyclopentanecarboxylic acid, 2-[(4'-chloro[1,1'-biphenyl]-4-yl)carbonyl]-5-[[(2-methoxyethoxy)methoxy]methyl]-, (1α,2β,5β)-;
Cyclopentanecarboxylic acid, 2-[(4'-chloro[1,1'-biphenyl]-4-yl)carbonyl]-5-[[(phenylmethyl)thio]methyl]-, (1α,2β, 5β)-;
Cyclopentanecarboxylic acid, 2-[(4'-chloro[1,1'-biphenyl]-4-yl)carbonyl]-5[(phenylthio)methyl]-, (1 a,2p,5, )-;
Cyclopentanecarboxylic acid, 2-[(4'-chloro[1,1'-biphenyl]-4-yl)carbonyl]-5-[(propylthio)methyl]-, (1α,2β,5β)-;
Cyclopentanecarboxylic acid, 2-[(2-benzothiazolylthio)methyl]-5-[(4'-chloro[1,1'-biphenyl]-4-yl)carbonyl]-, (1α,2β,5β,)-;
Benzoic acid, 2-[[[2-carboxy-3-[(4'-chloro[1,1'-biphenyl]-4-yl)carbonyl]cyclopentyl]methyl]thio]-, 1-methyl ester, (1α,2β,3β)-;
Cyclopentanecarboxylic acid, 2-[(4'-chloro[1,1'-biphenyl]-4-yl)carbonyl]-5-[[[(phenylmethoxy)carbonyl]-amino]methyl]-, (1α,2β,5β)-;
Benzoic acid, 2-methyl-, [2-carboxy-3-[(4'-chloro[1,1'-biphenyl]-4-yl)carbonyl]cyclopentyl]methyl ester, (1α, 2β,3α)-;
Benzoic acid, 3-methyl-, [2-carboxy-3-[(4'-chloro[1,1'-biphenyl]-4-yl)carbonyl]cyclopentyl]methyl ester, (1α, 2β,3β)-;

Benzoic acid, 4-methyl-, [2-carboxy-3-[(4'-chloro[1,1'-biphenyl]-4-yl)carbonyl]cyclopentyl]methyl ester, (1α,2β,3β)-;
Benzoic acid, 2-methoxy-, [2-carboxy-3-[(4'-chloro[1,1'-biphenyl]-4-yl)carbonyl]cyclopentyl)methyl ester, (1α,2β,3β)-;
Benzoic acid, 3-methoxy-, [2-carboxy-3-[(4'-chloro[1,1'-biphenyl]-4-yl)carbonyl]cyclopentyl]methyl ester, (1α,2β,3β)-;
Benzoic acid, 4-methoxy-, [2-carboxy-3-[(4'-chloro[1,1'-biphenyl]-4-yl)carbonyl]cyclopentyl]methyl ester, (1α,2β,3β)-;
Cyclopentanecarboxylic acid, 2-[(2-benzoxazolylthio)methyl]-5-[(4'-chloro[1,1'-biphenyl]-4-yl)carbonyl]-, (1α,2β,5β)-;
Cyclopentanecarboxylic acid, 2-[(4'-chloro[1,1'-biphenyl]-4-yl)carbonyl]-5-[(,3-dihydro-4-nitro-1,3-dioxo-2H-isoindol-2-yl)methyl]-, (1α,2β,5β)-;
Cyclopentanecarboxylic acid, 2-[(4'-chloro[1,1'-biphenyl]-4-yl)carbonyl]-5-[(1,3-dihydro-5-nitro-1,3-dioxo-2H-isoindol-2-yl)methyl]-, (1α,2β,5β)-;
2H-Benz[f]isoindole-2-butanoic acid, α-[2-(4'-ethoxy[1,1'-biphenyl]-4-yl)-2-oxoethyl]-1,3-dihydro-1,3-dioxo-;
[1,1'-Biphenyl]-4-butanoic acid, α-(acetylamino)-4'-chloro-γ-oxo-;
2H-Isoindole-2-hexanoic acid, α-[2-(4'-chloro[1,1'-biphenyl]-4-yl)-2-oxoethyl]-1,3-dihydro-1,3-dioxo-;
[1,1'-Biphenyl]-4-butanoic acid, 4'-chloro-α-[[[3-(methoxycarbonyl)phenyl]thio]methyl]-γ-oxo-;
[1,1'-Biphenyl]-4-butanoic acid, 4'-chloro-α-[[(2,6-(dimethylphenyl)thio]methyl]-γ-oxo-;
[1,1'-Biphenyl]-4-butanoic acid, 4'-chloro-α-[[[4-fluoro-2-(methoxycarbonyl)phenyl]thio]methyl]-γ-oxo-;
[1,1'-Biphenyl]-4-butanoic acid, 4'-chloro-α-[[[3-[(diethylamino)carbonyl]phenyl]thio]methyl]-γ-oxo-;
[1,1'-Biphenyl]-4-butanoic acid, 4'-chloro-α-[[[2-[(dimethylamino)carbonyl]phenyl]thio]methyl]-γ-oxo-;
[1,1'-Biphenyl]-4-butanoic acid, 4'-chloro-α-[[[3-[(dimethylamino)carbonyl]phenyl]thio]methyl]-γ-oxo-;
Bicyclo[2.2.1]hept-5-ene-2-carboxylic acid, 3-[[4'-(pentyloxy)[1,1'-biphenyl]4-yl]carbonyl]-, (2-endo,3-exo)-;
1-Cyclopentene-1-carboxylic acid, 5-[(4'-chloro[1,1'-biphenyl]-4-yl)carbonyl]-;
Cyclopentanecarboxylic acid, 2-[(4'-chloro[1,1'-biphenyl]-4-yl)carbonyl]-5-[(phenylmethyl)thio]-, (1α,2β,5β)-;
Cyclopentanecarboxylic acid, 2-[(4'-chloro[1,1'-biphenyl-4-yl)carbonyl]-5-[(phenylmethyl)thio]-, (1α,2β,5β)-;
1-Cyclopentene-1-carboxylic acid, 5-[[4'-(pentyloxy)[1,1'-biphenyl]4-yl]carbonyl]-;
1-Cyclopentene-1-carboxylic acid, 5-[[4'-(hexyloxy)[1,1'-biphenyl]-4-yl)]carbonyl]-;
[1,1'-Biphenyl]-4-butanoic acid, 4'-hydroxy-γ-oxo-α-[(phenylthio)methyl]-;
[1,1'-Biphenyl]-4-butanoic acid, α-[2-2-[(butylamino)carbonyl]phenyl]ethyl]-4'-chloro-γ-oxo-;
[1,1'-Biphenyl]-4-butanoic acid, α-[2-(3-carboxyphenyl)ethyl]-4'-chloro-γ-oxo-;
[1,1'-Biphenyl]-4-butanoic acid, 4'-chloro-α-[2-[3-[(diethylamino)carbonyl]phenyl]ethyl]-γ-oxo-;
[1,1'-Biphenyl]-4-butanoic acid, α-[2-[3-[(butylamino)carbonyl]phenyl]ethyl]-4'-chloro-γ-oxo-;
[1,1'-Biphenyl]-4-butanoic acid, 4'-chloro-α-[2-[4-[(diethylamino)carbonyl]phenyl]ethyl]-γ-oxo-;
[1,1'-Biphenyl]-4-butanoic acid, α-[2-4-[(butylamino)carbonyl]phenyl]ethyl]-4'-chloro-γ-oxo-;
[1,1'-Biphenyl]-4-butanoic acid, α-[2-(4-carboxyphenyl)ethyl]-4'-chloro-γ-oxo-;

[1,1'-Biphenyl]-4-butanoic acid, 4'-methoxy-γ-oxo-α-(2-phenylethyl)-;
[1,1'-Biphenyl]-4-butanoic acid, 4'-hydroxy-γ-oxo-α-(2-phenylethyl)-;
[1,1'-Biphenyl]-4-butanoic acid, 4'-ethoxy-γ-oxo-α-(2-phenylethyl)-;
[1,1'-Biphenyl]-4-butanoic acid, γ-oxo-α-(2-phenylethyl)-4'-propoxy-;
[1,1'-Biphenyl]-4-butanoic acid, γ-oxo-4'-(pentyloxy)-α-(2-phenylethyl)-;
[1,1'-Biphenyl]-4-butanoic acid, 4'-(hexyloxy)-γ-oxo-α-(2-phenylethyl)-;
[1,1'-Biphenyl]-4-butanoic acid, 4'-butoxy-γ-oxo-α-(2-phenylethyl)-;
[1,1'-Biphenyl]-4-butanoic acid, γ-oxo-α-(2-phenylethyl)4'-(phenylmethoxy)-;
[1,1'-Biphenyl]-4-butanoic acid, α-[2-(3-iodophenyl)ethyl]-γ-oxo-4'-(pentyloxy)-;
[1,1'-Biphenyl]-4-butanoic acid, α-[2-(3-iodophenyl)ethyl]-γ-oxo4'-(phenylmethoxy)-;
[1,1'-Biphenyl]-4-butanoic acid, α-[2-(3-[(diethylamino)carbonyl]phenyl)ethyl]-γ-oxo-4'-(pentyloxy)-;
[1,1'-Biphenyl]-4-butanoic acid, α-[2-(3-[(diethylamino)carbonyl]phenyl]ethyl]-γ-oxo-4'-(phenylmethoxy)-;
1,2-Pyrrolidinedicarboxylic acid, 3-[(4'-chloro[1,1'-biphenyl]-4-yl)carbonyl]-, 1-(phenylmethyl)ester, (2S-trans)-;
1,2-Pyrrolidinedicarboxylic acid, 3-[(4'-chloro[1,1'-biphenyl]-4-yl)carbonyl]-, 1-(phenylmethyl)ester, (2'R-trans)-;
L-Proline, 3-[(4'-chloro[1,1'-biphenyl]-4-yl)carbonyl]-1-[[(phenylmethyl)amino]carbonyl]-, trans-;
L-Proline, 3-[(4'-chloro[1,1'-biphenyl]-4-yl)carbonyl]-1-(1-oxo-3-phenylpropyl)-, trans-;
L-Proline, 3-[(4'-chloro[1,1'-biphenyl]-4-yl)carbonyl]-1-(phenylacetyl)-, trans-;
L-Proline, 3-[(4'-chloro[1,1'-biphenyl]-4-yl)carbonyl]-1-(3,3-dimethyl-1-oxobutyl)-, trans-;
[1,1'-Biphenyl]-4-butanoic acid, 4'-chloro-α-heptyl-γ-oxo-;
[1,1'-Biphenyl]-4-butanoic acid, 4'-chloro-α-decyl-γ-oxo-;
[1,1'-Biphenyl]-4-butanoic acid, 4'-nitro-γ-oxo-α-(2-phenylethyl)-;
[1,1'-Biphenyl]-4-butanoic acid, 4'-cyano-γ-oxo-α-(2-phenylethyl)-;
[1,1'-Biphenyl]-4-butanoic acid, 4'-chloro-α-[2-(2-iodophenyl)ethyl]-γ-oxo-:
[1,1'-Biphenyl]-4-butanoic acid, 4'-chloro-α-[2-(3-iodophenyl)ethyl]-γ-oxo-;
[1,1'-Biphenyl]-4-butanoic acid, 4'-chloro-α-[2-(4-iodophenyl)ethyl]-γ-oxo-;
[1,1'-Biphenyl]-4-butanoic acid, 4'-chloro-α-[2-(3,5-dimethoxyphenyl)ethyl]-γ-oxo-;
[1,1-Biphenyl]-4-butanoic acid, 4'-chloro-γ-oxo-α-phenyl-;
[1,1'-Biphenyl]-4-butanoic acid, 4'-chloro-γ-oxo-α-(phenylmethyl)-;
[1,1'-Biphenyl]-4-butanoic acid, 4'-chloro-γ-oxo-α-(2-phenylethyl)-;
[1,1'-Biphenyl]-4-butanoic acid, 4'-chloro-γ-oxo-α-[(trimethylsilyl)methyl]-;
[1,1'-Biphenyl]-4-butanoic acid, 4'-bromo-γ-oxo-α-(3-phenylpropyl)-;
[1,1'-Biphenyl]-4-butanoic acid, γ-oxo-α-(3-phenylpropyl)-;
[1,1'-Biphenyl]-4-butanoic acid, 4'-amino-γ-oxo-α-(2-phenylethyl)-;
[1,1'-Biphenyl]-4-butanoic acid, γ-oxo-α-(2-phenylethyl)-4'-[[(phenylmethoxy)carbonyl]amino]-;
[1,1'-Biphenyl]-4-butanoic acid, 4'-[[(1,1-dimethylethoxy)carbonyl]amino]-γ-oxo-α-(2-phenylethyl)-;

[1,1'-Biphenyl]-4-butanoic acid, 4'-(acetylamino)-γ-oxo-α-(2-phenylethyl)-;
[1,1'-Biphenyl]-4-butanoic acid, γ-oxo-4'-[(1-oxopentyl)amino3-α-(2-phenylethyl)-;
[1,1'-Biphenyl]-4-butanoic acid, 4'-[(3,3-dimethyl-1-oxobutyl)amino]-γ-oxo-α-(2-phenylethyl)-;
[1,1'-Biphenyl]-4-butanoic acid, 4'-chloro-α-[2-[2-methoxycarbonyl)phenyl]ethyl]-γ-oxo-;
[1,1'-Biphenyl]-4-butanoic acid, α-[2-(2-carboxyphenyl)ethyl]-4'-chloro-γ-oxo-; [1,1'-Biphenyl]-4-butanoic acid, 4'-chloro-α-[2-[2-[(diethylamino)carbonyl)phenyl]ethyl]-γ-oxo-; [1,1'-Biphenyl]-4-butanoic acid, 4'-chloro-α-[2-[3-[(diethylamino)carbonyl)phenyl]ethyl]-γ-oxo-, (S)-; and [1,1'-Biphenyl]-4-butanoic acid, 4'-chloro-α-[2-[3-[(diethylamino)carbonyl)phenyl]ethyl]-γ-oxo-, (R)-.

Fenbufen and compounds related to fenbufen can be utilized. Such compounds are described in U.S. Pat. No. 3,784,701 and by Child, et al., *J. Pharm. Sci.*, 66, 466–476 (1977), and Arzneim-Forsch, 1980, 30(4A):695–702, all of which are incorporated herein by reference. Preferred compounds from the fenbufen series to be utilized in this invention have the formula

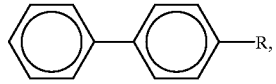

where R is

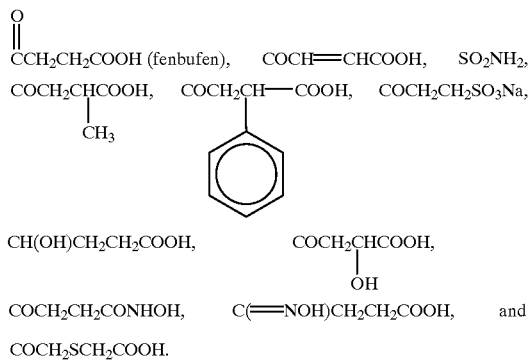

and COCH$_2$SCH$_2$COOH.

Numerous peptides are known matrix metalloproteinase inhibitors. Typical of such peptides are those described in U.S. Pat. Nos. 5,300,501; 5,530,128; 5,455,258; 5,552,419; WO 95/13289; and WO 96/11209, all of which are incorporated herein by reference. Such compounds are illustrated by the formula

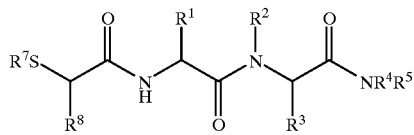

where each of the variable groups can include hydrogen alkyl, aryl, heteroaryl, alkenyl, alkynyl, carboxy, and the like. Preferred compounds from within this class which can be utilized in the method of this invention include the following:

N-[2,3-bis-Acetylmercaptopropanoyl]-L-leucyl-L-phenylalanine N-methylamide;
N-[2-Acetylmercapto-3-methoxycarbonylpropanoyl]-L-leucyl-L-phenylalanine N-methylamide;
N-[2-Acetylmercapto-4-methoxycarbonylbutanoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanoyl]-L-leucyl-L-phenylalanine N-methylamide;
N-[2-Acetylmercapto-4-phthalimidobutanoyl]-L-leucyl-L-phenylalanine N-methylamide;
N-[2-Acetylmercapto-5-phthalimidopentanoyl]-L-leucyl-L-phenylalanine N-methylamide;
N-[2-Acetylmercapto-6-phthalimidohexanoyl]-L-leucyl-L-phenylalanine N-methylamide;
N-[2,3-bis-Mercaptopropanoyl]-L-leucyl-L-phenylalanine N-methylamide;
N-[2-Mercapto-3-methoxycarbonylpropanoyl]-L-leucyl-L-phenylalanine N-methylamide;
N-[2-Mercapto-4-methoxycarbonylbutanyol]-L-leucyl-L-phenylalanine N-methylamide;
N-[2-Mercapto-4-methoxycarbonylpentanoyl]-L-leucyl-L-phenylalanine N-methylamide;
N-[2-Mercapto-6-methoxycarbonylhexanoyl]-L-leucyl-L-phenylalanine N-methylamide;
N-[2-Mercapto-4-phthalimidobutanoyl]-L-leucyl-phenylalanine N-methylamide;
N-[2-Mercapto-5-phthalimidopentanoyl]-L-leucyl-L-phenylalanine N-methylamide;
N-[2-Mercapto-6-phthalimidohexanyoyl]-L-leucyl-L-phenylalanine N-methylamide;
N-[2-Acetylmercapto-5-methoxycarbonylpentanoyl]-L-leucyl-L-phenylalanine N-methylamide;
N-[2-Acetylmercapto-6-methoxycarbonylhexanyol]-L-leucyl-L-phenylalanine N-methylamide;
N-[2-Acetylmercapto-6-methoxycarbonylhexanyol]-L-valinyl-L-phenylalanine N-methylamide;
N-[2-Acetylmercapto-6-methoxycarbonylhexanyol]-L-leucyl-L-tryptophan N-methylamide;
N-[2-Acetylmercapto-5-phthalimidopentanoyl]-L-leucyl-L-phenylalanine N-methylamide;
N-[2-Acetylmercapto-5-phthalimidopentanoyl]-L-valinyl-L-phenylalanine N-methylamide;
N-[2-Acetylmercapto-5-phthalimidopentanoyl]-L-leucyl-L-tryptophan N-methylamide;
N-[2-Acetylmercapto-5-phthalimidopentanoyl]-L-leucyl-L-[β-(4-thiazolyl)]alaine N-methylamide;
N-[2-Acetylmercapto-5-phthalimidopentanoyl]-L-leucyl-L-(β-(2-pyridyl)alanine N-methylamide;
N-[2-Acetylmercapto-5-phthalimidopentanoyl]-L-leucyl-5-methyl-L-glutamicacid N-methylamide;
N-[2-Acetylmercapto-6-phthalimidohexanoyl]-L-leucyl-L-phenylalanine N-methylamide;
N-[2-Acetylmercapto-2-(3-phthalimido)phenylacetyl]-L-leucyl-L-phenylalanine N-methylamide;
N-[2-Mercapto-5-methoxycarbonylpentanoyl]-L-phenylalanine N-methylamide;
N-[2-Mercapto-6-methoxycarbonylhexanyol]-L-leucyl-L-phenylalanine N-methylamide;
N-[2-Mercapto-6-methoxycarbonylhexanyol]-L-leucyl-L-trptophan N-methylamide;
N-[2-Mercapto-5-phthalimidopentanoyl]-L-leucyl-L-phenylalanine N-methylamide;
N-[2-Mercapto-5-phthalimidopentanoyl]-L-leucyl-L-tryptophan N-methylamide;
N-[2-Mercapto-5-phthalimidopentanoyl]-L-leucyl-L-[β-(4-thiazolyl)alanine N-methylamide;
N-[2-Mercapto-5-phthalimidopentanoyl]-L-leucyl-L-[β-(2-pyridyl)]alanine N-methylamide;

N-[2-Mercapto-5-phthalimidopentanoyl]-L-leucyl-5-methyl-L-glutamic acid N-methylamide;
N-[2-Mercapto-6-phthalimidohexanoyl]-L-leucyl-L-phenylalanine N-methylamide;
N-[N-Mercaptoacetyl)-L-leucyl]-L-phenylalanine N-methylamide;
N-[Acetomercaptoacyl)-L-leucyl-L-phenylalanine methylamide;
(RS)-2-(Acetylthio)pentanoyl-L-leucyl-L-phenylalanine N-methylamide;
(RS)-2-(Acetylthio)propanoyl-L-leucyl-L-phenylalanine N-methylamide;
(RS)-2-(Acetylthio)-3-methylbutanoyl-L-leucyl-L-phenylalanine N-methylamide;
(RS)-2-(Acetylthio)-2-phenylacetyl-L-leucyl-L-phenylalanine N-methylamide;
(RS)-2-(Acetylthio)-3-phenylpropanoyl-L-leucyl-L-phenylalanine N-methylamide;
(RS)-2-(Acetylthio)-4-phenylbutanoyl-L-leucyl-L-phenylalanine N-methylamide;
N-(Acetylmercaptoacyl)-L-threonyl-L-phenylalanine methylamide;
N-(Acetylmercaptoacyl)-L-leucyl-L-tryptophan methylamide;
(RS)-2-Mercaptopentanoyl-L-leucyl-L-phenylalanine N-methylamide;
(RS)-2-Mercaptopropanoyl-L-leucyl-L-phenylalanine N-methylamide;
(RS)-2-Mercapto-3-methylbutanoyl-L-leucyl-L-phenylalanine N-methylamide;
(RS)-2-Mercapto-2-phenylacetyl-L-leucyl-L-phenylalanine N-methylamide;
(RS)-2-Mercapto-3-phenylpropanoyl-L-leucyl-L-phenylalanine N-methylamide;
(RS)-2-Mercapto-4-phenylbutanoyl-L-leucyl-L-phenylalanine N-methylamide;
N-[N-(Mercaptoacetyl)-L-threonyl]-L-phenylalanine methylamide; and
N-[N-(Mercaptoacetyl)-L-leucyl]-L-tryptophan methylamide.

Additional matrix metalloproteinase (MMP) inhibitors which can be utilized to prevent and treat heart failure include the following:

[4-(N-Hydroxyamino)-2(R)-cyclohexylmethylsuccinyl]-L-β-cyclohexylalanine-N-(2-phenylethyl)amide;
[4-N-(Hydroxyamino)-2R-isobutylsuccinyl]-L-β-cyclohexylalanine-N-(2-phenylethyl)amide;
[4-(N-Hydroxyamino)-2R-phenylpropylsuccinyl]-L-β-cyclohexylalanine-N-(2-phenylethyl)amide;
[4-(N-Hydroxyamino)-2R-phenylpropylsuccinyl]-L-β-cyclohexylalanine-N-[2-(N,N-dimethylamino]ethyl)amide;
[4-(N-Hydroxyamino)-2R-phenylpropylsuccinyl]-L-β-cyclohexylalanine-N-[2-(p-sulphonamidophenyl)ethyl)amide;
[4-(N-Hydroxyamino)-2R-phenylpropylsuccinyl]-L-β-cyclohexylalanine-N-(2-(p-sulphonylphenyl)ethyl)amide;
[4-(N-Hydroxyamino)-2R-phenylpropylsuccinyl]-L-β-cyclohexylalanine-N-[2-(2-pyridyl)ethyl]amide;
[4-(N-Hydroxyamino)-2R-pentylsuccinyl]-L-β-cyclohexylalanine-N-(2-phenylethyl)amide;
[4-(N-Hydroxyamino)-2R-isoamylsuccinyl]-L-β-cyclohexylalanine-N-(2-phenylethyl)amide;
[4-(N-Hydroxyamino)-2R-phenylbutylsuccinyl]-L-β-cyclohexylalanine-N-(2-phenylethyl)amide;
[4-(N-Hydroxyamino)-2R-phenylpropylsuccinyl]-L-β-cyclohexylalanine-N-[3-(4-morpholinyl)propyl]amide;
[4-(N-Hydroxyamino)-2R-phenylpropylsuccinyl]-L-β-cyclohexylalanine-N-[β-alanine]amide;
[4-(N-Hydroxyamino)-2R-isobutylsuccinyl]-L-β-cyclohexylalanine amide;
[4-(N-Hydroxyamino)-2R-(3-phenylpropylsuccinyl]-L-β-cyclohexylalanine amide;
[4-(N-Hydroxyamino)-2R-(3-phenylbutyl)succinyl]-L-β-cyclohexylalanine amide;
[4-N-(Hydroxyamino)-2R-phenylethylsuccinyl]-L-leucine-N-(2-phenylethyl)amide;
[4-(N-Hydroxyamino)-2R-phenylpropylsuccinyl]-L-leucine-N-(2-phenylethyl)amide;
[4-(N-Hydroxyamino)-2(R)-isobutylsuccinyl]-L-tryptophan amide;
[4-(N-Hydroxyamino)-2(R)-isobutylsuccinyl]-L-valine amide;
[3-phosphono-2R,S-phenylpropyl-1-oxopropyl]-L-β-cyclohexylalanine-N-(2-phenylethyl)amide, dimethylester;
[3-Phosphono-2R-phenylpropyl-1-oxopropyl]-L-β-cyclohexylalanine-N-(2-phenylethyl)amide;
[3-Phosphono-2S-phenylpropyl-1-oxopropyl]-L-β-cyclohexylalanine-β-alanine;
[3-Phosphono-2R-phenylpropyl-1-oxopropyl]-L-β-cyclohexylalanine;
[3-Phosphono-2S-phenylpropyl-1-oxopropyl]-L-β-cyclohexylalanine-β-alanine, methyl ester;
[3-Phosphono-2R,S-phenylpropyl-1-oxopropyl]-L-β-cyclohexylalanine-N-[4(3-aminopropyl)morpholine] amide, bromine salt;
[3-Phosphono-2R,S-(4-methylphenyl)propyl-1-oxopropyl]-L-β-cyclohexylalanine-N-(2-phenylethyl)amide, diethylester;
[3-Phosphono-2R,S-(4-methylphenyl)propyl-1-oxopropyl]-L-β-cyclohexylalanine-N-(2-phenylethyl)-amide;
4-t-Butoxy-2(R)-[3-(2-phenoxyethyl)succinyl]-L-β-cyclohexylalanine-N-(2-phenylethyl)amide;
4-Hydroxy-2(R)-[3-(2-phenoxyethyl)succinyl]-L-β-cyclohexylalanine-N-(2-phenylethyl)amide;
4-(N-Hydroxyamino-2(R)-[3-(2-phenoxyethyl)succinyl]-L-β-cyclohexylalanine-N-(2-phenylethyl)amide;
{4-Hydroxy-2(R)-[3-(4-pyridinium)propyl]succinyl}-L-β-cyclohexylalanine-N-(2-phenylethyl)amide;
{4-(N-Hydroxyamino)-2(R)-[3-(4-pyridinium)propyl]succinyl}-L-β-cyclohexylalanine-N-(2-phenylethyl)amide;
{4-(N-Hydroxyamino)-2(R)-[3-(N-methyl-4-pyridinium)propyl]succinyl}-L-β-cyclohexylalanine-N-(2-phenylethyl)amide;
{4-Hydroxy-2-(R)-[3-(4-methylphenyl)propyl]succinyl}-L-β-cyclohexylalanine-N-[(2-morpholine-sulphonylamino)ethyl]amide;
{4-(N-Hydroxyamino)-2-(R)-[3-(4-methylphenyl)propyl]succinyl}-L-β-cyclohexylalanine-N-[(2-morpholinesulphonylamino)ethyl]amide;
{4-(N-Hydroxyamino)-2-(R)-[3-(4-chlorophenyl)propyl]succinyl}-L-β-cyclohexylalanine-N-[(2-morpholinesulphonylamino)ethyl]amide;
{4-N-Hydroxyamino)-2-(R)-[3-(4-methylphenyl)propyl]succinyl}-L-β-cyclohexylalanine-N-[(2-dimethylsulphonylamino)propyl]amide;
[4-(N-Hydroxyamino)-2(R)-[3-(4-chlorophenyl)propyl]succinyl]-L-[S-(methyl)penicillamine]-N-methylamide;
[4-(N-Hydroxyamino)-2(R)-[3-(4-chlorophenyl)propyl]succinyl]-L-[S-(methyl)penicillamine]amide;
[4-(N-Hydroxyamino)-2(R)-[3-(4-chlorophenyl)propyl]succinyl]-L-penicillamine]amide;

{4-(N-Hydroxyamino)-2(R)-[3-(4-chlorophenyl)propyl]
  succinyl}-L-[S-(methyl)penicillaminesulphone]-N-
  methylamide;
{4-(N-Hydroxyamino)-2(R)-[3-(4-chlorophenyl)propyl]
  succinyl}-L-[S-(methyl)penicillaminesulphoxide]-N-
  methylamide;
{4-(N-Hydroxyamino)-2(R)-[3-(4-chlorophenyl)propyl]
  succinyl}-L-penicillamine-N-methylamide;
[4-(N-Hydroxyamino)-2(R)-3-(2-methylpropyl)succinyl]-
  L-[S-methyl)penicillamine]-N-methylamide;
$N^4$-Hydroxy-$N^1$-(1-(S)-carbamoyl-2,2-dimethylpropyl)-2-
  (R)4-(chlorophenylpropyl)succinamide;
$N^4$-Hydroxy-$N^1$-(1-(S)-carbamoyl-2,2-dimethylpropyl)-2-
  (R)-(4-methylphenylpropyl)succinamide;
$N^4$-Hydroxy-$N^1$-(1-(S)-carbamoyl-2,2-dimethylpropyl)-2-
  (R)-(4-methoxyphenylpropyl)succinamide;
$N^4$-Hydroxy-$N^1$-(1-(S)-carbamoyl-2,2-dimethylpropyl)-2-
  (R)-(4-trifluoromethylphenylpropyl)succinamide;
$N^4$-Hydroxy-$N^1$-(1-(S)-carbamoyl-2,2-dimethylpropyl)-2-
  (R)-(4-chloromethylphenylpropyl)succinamide;
N-[N-(Mercaptoacetyl)-L-leucyl]-L-phenylalanine methylamide;
N-(Acetomercaptoacyl)-L-leucyl]-L-phenylalanine methylamide;
(RS)-2-(Acetylthio)pentanoyl-L-leucyl-L-phenylalanine
  N-methylamide;
(RS)-2-(Acetylthio)propanoyl-L-leucyl-L-phenylalanine
  N-methylamide;
(RS)-2-(Acetylthio)-o-methylbutanoyl -L-leucyl
  -L-phenylalanine N-methylamide;
(RS)-2-(Acetylthio)-2-phenylacetyl-L-leucyl-L-
  phenylalanine N-methylamide;
(RS)-2-(Acetylthio)-3-phenylpropanoyl-L-leucyl-L-
  phenylalanine N-methylamide;
(RS)-2-(Acetylthio)-4-phenylbutanoyl-L-leucyl-L-
  phenylalanine N-methylamide;
N-(Acetylmercaptoacyl)-L-threonyl-L-phenylalanine
  methylamide;
N-(Acetylmercaptoacyl)-L-leucyl-L-tryptophan methylamide;
(RS)-2-Mercaptopentanoyl-L-leucyl-L-phenylalanine
  N-methylamide;
(RS)-2-Mercaptopropanoyl-L-leucyl-L-phenylalanine
  N-methylamide;
(RS)-2-Mercapto-3-methylbutanoyl-L-leucyl-L-
  phenylalanine N-methylamide;
(RS)-2-Mercapto-2-phenylacetyl-L-leucyl-L-phenylalanine
  N-methylamide;
(RS)-2-Mercapto-3-phenylpropanoyl-L-leucyl-L-
  phenylalanine N-methylamide;
(RS)-2-Mercapto4-phenylbutanoyl-L-leucyl-L-
  phenylalanine N-methylamide;
N-[N-(Mercaptoacetyl)-L-threonyl]-L-phenylalanine
  methylamide;
N-[N-(Mercaptoacetyl)-L-leucyl]-L-tryptophan methylamide;
N-[2,3-bis-Acetylmercaptopropanoyl]-L-leucyl-L-
  phenylalanine N-methylamide;
N-[2-Acetylmercapto-3-methoxycarbonylpropanoyl]-L-
  leucyl-L-phenylalanine N-methylamide;
N-[2-Acetylmercapto-4-methoxycarbonylbutanoyl]-L-
  leucyl-L-phenylalanine N-methylamide;
N-[2-Acetylmercapto-5-methoxycarbonylpentanoyl]-L-
  leucyl-L-phenylalanine N-methylamide;
N-[2-Acetylmercapto-6-methoxycarbonylhexanoyl]-L-
  leucyl-L-phenylalanine N-methylamide;
N-[2-Acetylmercapto-4-phthalimidobutanoyl]-L-leucyl-L-
  phenylalanine N-methylamide;
N-[2-Acetylmercapto-5-phthalimidopentanoyl]-L-leucyl-L-
  phenylalanine N-methylamide;
N-[2-Acetylmercapto-6-phthalimidohexanoyl]-L-leucyl-L-
  phenylalanine N-methylamide;
N-[2,3-bis-Mercaptopropanoyl]-L-leucyl-L-phenylalanine
  N-methylamide;
N-[2-Mercapto-3-methoxycarbonylpropanoyl]-L-leucyl-L-
  phenylalanine N-methylamide;
N-[2-Mercapto-4-methoxycarbonylbutanoyl]-L-leucyl-L-
  phenylalanine N-methylamide;
N-[2-Mercapto-5-methoxycarbonylpentanoyl]-L-leucyl-L-
  phenylalanine N-methylamide;
N-[2-Mercapto-6-methoxycarbonylhexanoyl]-L-leucyl-L-
  phenylalanine N-methylamide;
N-[2-Mercapto-4-phthalimidobutanoyl]-L-leucyl-L-
  phenylalanine N-methylamide;
N-[2-Mercapto-5-phthalimidopentanoyl]-L-leucyl-L-
  phenylalanine N-methylamide;
N-[2-Mercapto-6-phthalimidohexanoyl]-L-leucyl-L-
  phenylalanine N-methylamide;
N-[2-Acetylmercapto-5-methoxycarbonylpentanoyl]-L-
  leucyl-L-phenylalanine N-methylamide;
N-[2-Acetylmercapto-6-methoxycarbonylhexanoyl]-L-
  leucyl-L-phenylalanine N-methylamide;
N-[2-Acetylmercapto-6-methoxycarbonylhexanoyl]-L-
  valinyl-L-phenylalanine N-methylamide;
N-[2-Acetylmercapto-6-methoxycarbonylhexanoyl]-L-
  leucyl-L-tryptophan N-methylamide;
N-[2-Acetylmercapto-5-phthalimidopentanoyl]-L-leucyl-L-
  phenylalanine N-methylamide;
N-[2-Acetylmercapto-5-phthalimidopentanoyl]-L-valinyl-
  L-phenylalanine N-methylamide;
N-[2-Acetylmercapto-5-phthalimidopentanoyl]-L-leucyl-L-
  tryptophan N-methylamide;
N-[2-Acetylmercapto-5-phthalimidopentanoyl]-L-leucyl-L-
  [β-(4-thiazolyl)]alanine N-methylamide;
N-[2-Acetylmercapto-5-phthalimidopentanoyl]-L-leucyl-L-
  [β-(2-pyridyl)]alanine N-methylamide;
N-[2-Acetylmercapto-5-phthalimidopentanoyl]-L-leucyl-5-
  methyl-L-glutamic acid N-methylamide;
N-[2-Acetylmercapto-6-phthalimidohexanoyl]-L-leucyl-L-
  phenylalanine N-methylamide;
N-[2-Acetylmercapto-2-(3-phthalimido)phenylacetyl]-L-
  leucyl-L-phenylalanine N-methylamide;
N-[2-Mercapto-5-methoxycarbonylpentanoyl]-L-leucyl-L-
  phenylalanine N-methylamide;
N-[2-Mercapto-6-methoxycarbonylhexanoyl]-L-leucyl-L-
  phenylalanine N-methylamide;
N-[2-Mercapto-6-methoxycarbonylhexanoyl]-L-leucyl-L-
  tryptophan N-methylamide;
N-[2-Mercapto-5-phthalimidopentanoyl]-L-leucyl-L-
  phenylalanine N-methylamide;
N-[2-Mercapto-5-phthalimidopentanoyl]-L-leucyl-L-
  tryptophan N-methylamide;
N-[2-Mercapto-5-phthalimidopentanoyl]-L-leucyl-L-[β-(4-
  thiazolyl)alanine N-methylamide;
N-[2-Mercapto-5-phthalimidopentanoyl]-L-leucyl-L-[β-(2-
  pyridyl)]alanine N-methylamide;
N-[2-Mercapto-5-phthalimidopentanoyl]-L-leucyl-5-
  methyl-L-glutamic acid N-methylamide;
N-[2-Mercapto-6-phthalimidohexanoyl]-L-leucyl-L-
  phenylalanine N-methylamide;
N-Hydroxy-2(R)-[[4-methoxybenzenesulfonyl]-(3-picolyl)
  amino]-3-methylbutanamide;
N-Hydroxy-2(R)-[[4-methoxybenzenesulfonyl]-3-picolyl)
  amino]-2-cyclohexylacetamide;
N-Hydroxy-2(R)-[[4-methoxybenzenesulfonyl]-(benzyl)
  amino]-4-methylpentanamide;

N-Hydroxy-2(R)-[[4-methoxybenzenesulfonyl]-(benzyl) amino]-6-[(N,N-dimethylglycyl)amino]hexanamide hydrochloride;
N-Hydroxy-2(R)-[[4-methoxybenzenesulfonyl]-(3-picolyl) amino]-3-methylbutanamide;
N-Hydroxy-2(R)-[[4-methoxybenzenesulfonyl]-(4-picolyl) amino]-2-cyclohexylacetamide;
N-Hydroxy-2(R)-[(4-methoxybenzenesulfonyl]-(4-picolyl) amino]-2-(2-tetrahydrofuranyl)acetamide;
N-Hydroxy-2(R)-[[4-methoxybenzenesulfonyl]-(3-picolyl) amino]-3-methylbutanamide;
[4-(N-Hydroxyamino)-2R-isobutyl-3S-methylsuccinyl]-$N^2$-(S)-piperazic acid N-methyl amide;
[4-(N-Hydroxyamino)-2R-isobutyl-3S-benzylsuccinyl]-$N^2$-(S)-piperazic acid N-methyl amide;
[4-(N-Hydroxyamino)-2R-isobutyl-3S-methoxyphenylsuccinyl]-$N^2$-(S)-piperazic acid N-methyl amide;
[4-(N-Hydroxyamino)-2R-isobutyl-3S-methoxybenzylsuccinyl]-$N^2$-(S)-piperazic acid N-methyl amide;
[4-(N-Hydroxyamino)-2R-isobutyl-3S-methylthiophenylsuccinyl]-$N^2$-(S)-piperazic acid N-methyl amide;
[4-(N-Hydroxyamino)-2R-isobutyl-3S-methylthiobenzylsuccinyl]-$N^2$-(S)-piperazic acid N-methyl amide;
[4-(N-Hydroxyamino)-2R-isobutyl-3S-(methylthio-2-thienyl)succinyl]-$N^2$-(S)-piperazic acid N-methyl amide;
[4-(N-Hydroxyamino)-2R-isobutyl-3S-methylacetate]-$N^2$-(S)-piperazic acid N-methyl amide;
[4-(N-Hydroxyamino)-2R-isobutyl-3S-methylisopropanoate]-$N^2$-(S)-piperazic acid N-methyl amide;
[4-(N-Hydroxyamino)-2R-isobutyl-3S-methyl-tert-butanoate]-$N^2$-(S)-piperazic acid N-methyl amide;
[4-(N-Hydroxyamino)-2R-isobutyl-3S-methyl-thioacetate]-$N^2$-(S)-piperazic acid N-methyl amide;
[4-(N-Hydroxyamino)-2R-isobutyl-3S-methylthioisopropanoate]-$N^2$-(S)-piperazic acid N-methyl amide;
[4-(N-Hydroxyamino)-2R-isobutyl-3S-methyl-(2-pyridyl)]-$N^2$-(S)-piperazic acid N-methyl amide;
[4-(N-Hydroxyamino)-2R-isobutyl-3S-methyl-(3-pyridyl)]-$N^2$-(S)-piperazic acid N-methyl amide;
[4-(N-Hydroxyamino)-2R-isobutyl-3S-methyl-(4-pyridyl)]-$N^2$-(S)-piperazic acid N-methyl amide;
[4-(N-Hydroxyamino)-2R-isobutyl-3S-methylthio-tert-butanoate]-$N^2$-(S)-piperazic acid N-methyl amide;
[4-(N-Hydroxyamino)-2R-hexyl-3S-methylsuccinyl]-$N^2$-(S)-piperazic acid N-methyl amide;
[4-(N-Hydroxyamino)-2R-hexyl-3S-benzylsuccinyl]-$N^2$-(S)-piperazic acid N-methyl amide;
[4-(N-Hydroxyamino)-2R-hexyl-3S-methoxyphenylsuccinyl]-$N^2$-(S)-piperazic acid N-methyl amide;
[4-(N-Hydroxyamino)-2R-hexyl-3S-methoxybenzylsuccinyl]-$N^2$-(S)-piperazic acid N-methyl amide;
[4-(N-Hydroxyamino)-2R-hexyl-3S-methylthiophenylsuccinyl]-$N^2$-(S)-piperazic acid N-methyl amide;
[4-(N-Hydroxyamino)-2R-hexyl-3S-methylthiobenzylsuccinyl]-$N^2$-(S)-piperazic acid N-methyl amide;
[4-(N-Hydroxyamino)-2R-hexyl-3S-(methylthio-2-thienyl)succinyl]-$N^2$-(S)-piperazic acid N-methyl amide;
[4-(N-Hydroxyamino)-2R-hexyl-3S-benzylsuccinyl]-$N^2$-(S)-piperazic acid N-methyl amide;
[4-(N-Hydroxyamino)-2R-hexyl-3S-methyl acetate]-$N^2$-(S)-piperazic acid N-methyl amide;
[4-(N-Hydroxyamino)-2R-hexyl-3S-methylisopropanoate]-$N^2$-(S)-piperazic acid N-methyl amide;
[4-(N-Hydroxyamino)-2R-hexyl-3S-methyl tert-butanoate]-$N^2$-(S)-piperazic acid N-methyl amide;
[4-(N-Hydroxyamino)-2R-hexyl-3S-methylthioacetate]-$N^2$-(S)-piperazic acid N-methyl amide;
[4-(N-Hydroxyamino)-2R-hexyl-3S-methylthioisopropanoate]-$N^2$-(S)-piperazic acid N-methyl amide;
[4-(N-Hydroxyamino)-2R-hexyl-3S-methylthio-tert-butanoate]-$N^2$-(S)-piperazic acid N-methyl amide;
[4-N-Hydroxyamino)-2R-hexyl-3S-methyl-(2-pyridyl)]-$N^2$-(S)-piperazic acid N-methyl amide;
[4-(N-Hydroxyamino)-2R-hexyl-3S-methyl-(3-pyridyl)]-$N^2$-(S)-piperazic acid N-methyl amide;
[4-(N-Hydroxyamino)-2R-hexyl-3S-methyl-(4-pyridyl)]-$N^2$-(S)-piperazic acid N-methyl amide;
[4-(N-Hydroxyamino)-2R-ethylphenyl-3S-methylsuccinyl]-$N^2$-(S)-piperazic acid N-methyl amide;
[4-(N-Hydroxyamino)-2R-ethylphenyl-3S-benzylsuccinyl]-$N^2$-(S)-piperazic acid N-methyl amide;
[4-(N-Hydroxyamino)-2R-ethylphenyl-3S-methoxyphenylsuccinyl]-$N^2$-(S)-piperazic acid N-methyl amide;
[4-(N-Hydroxyamino)-2R-ethylphenyl-3S-methoxybenzylsuccinyl]-$N^2$-(S)-piperazic acid N-methyl amide;
[4-(N-Hydroxyamino)-2R-ethylphenyl-3S-methylthiophenylsuccinyl]-$N^2$-(S)-piperazic acid N-methyl amide;
[4-(N-Hydroxyamino)-2R-ethylphenyl-3S-methylthiobenzylsuccinyl]-$N^2$-(S)-piperazic acid N-methyl amide;
[4-(N-Hydroxyamino)-2R-ethylphenyl-3S-(methylthio-2-thienyl)succinyl]-$N^2$-(S)-piperazic acid N-methyl amide;
[4-(N-Hydroxyamino)-2R-ethylphenyl-3S-benzylsuccinyl]-$N^2$-(S)-piperazic acid N-methyl amide;
[4-(N-Hydroxyamino)-2R-ethylphenyl-3S-methyl acetate]-$N^2$-(S)-piperazic acid N-methyl amide;
[4-(N-Hydroxyamino)-2R-ethylphenyl-3S-methylisopropanoate]-$N^2$-(S)-piperazic acid N-methyl amide;
[4-(N-Hydroxyamino)-2R-ethylphenyl-3S-methyl-tert-butanoate]-$N^2$-(S)-piperazic acid N-methyl amide;
[4-(N-Hydroxyamino)-2R-ethylphenyl-3S-methylthioacetate]-$N^2$-(S)-piperazic acid N-methyl amide;
[4-(N-Hydroxyamino)-2R-ethylphenyl-3S-methylthioisopropanoate]-$N^2$-(S)-piperazic acid N-methyl amide;
[4-(N-Hydroxyamino)-2R-ethylphenyl-3S-methylthio-tert-butanoate]-$N^2$-(S)-piperazic acid N-methyl amide;
[4-(N-Hydroxyamino)-2R-octyl-3S-methylsuccinyl]-$N^2$-(S)-piperazic acid N-methyl amide;
[4-(N-Hydroxyamino)-2R-octyl-3S-methylthiophenylsuccinyl]-$N^2$-(S)-piperazic acid N-methyl amide;
[4-(N-Hydroxyamino)-2R-octyl-3S-methylthiobenzylsuccinyl]-$N^2$-(S)-piperazic acid N-methyl amide;
[4-(N-Hydroxyamino)-2R-octyl-3S-methylthio-2-thienyl)succinyl]-$N^1$-(S)-piperazic acid N-methyl amide;
[4-(N-Hydroxyamino)-2R-octyl-3S-methyl acetate]-$N^2$-(S)-piperazic acid N-methyl amide;
[4-(N-Hydroxyamino)-2R-octyl-3S-methylisopropanoate]-$N^2$-(S)-piperazic acid N-methyl amide;

[4-(N-Hydroxyamino)-2R-octyl-3S-methyl tert-butanoate]-N²-(S)-piperazic acid N-methyl amide;
[4-(N-Hydroxyamino)-2R-octyl-3S-methylthioacetate]-N²-(S)-piperazic acid N-methyl amide;
[4-(N-Hydroxyamino)-2R-octyl-3S-methylthioisopropanoate]-N²-(S)-piperazic acid N-methyl amide;
[4-(N-Hydroxyamino)-2R-octyl-3S-methylthio-tert-butanoate]-N²-(S)-piperazic acid N-methyl amide;
[4-(N-Hydroxyamino)-2R-octyl-3S-methyl-(2-pyridyl)]-N²-(S)-piperazic acid N-methyl amide;
[4-(N-Hydroxyamino)-2R-octyl-3S-methyl-(3-pyridyl)]-N²-(S)-piperazic acid N-methyl amide;
[4-(N-Hydroxyamino)-2R-octyl-3S-methyl-(4-pyridyl)]-N²-(S)-piperazic acid N-methyl amide;
[4-(N-Hydroxyamino)-2R-isobutyl-3S-methylsuccinyl]-N²-(S)-4'(S/R)-benzylpiperazic acid N-methyl amide;
[4-(N-Hydroxyamino)-2R-isobutyl-3S-methylsuccinyl]-N²-(S)-5'(S/R)-benzylpiperazic acid N-methyl amide;
[4-(N-Hydroxyamino)-2R-isobutyl-3S-methylsuccinyl]-N²-(S)-6'(S/R)-benzylpiperazic acid N-methyl amide;
[4-(N-Hydroxyamino)-2R-isobutyl-3S-methylsuccinyl]-N²-(S)-[5',6']benzopiperazic acid N-methyl amide;
N-[1(R)-Carboxy-ethyl]-α-(S)-isobutylglycine-(S)-N²-piperazic acid methyl amide;
N-[1(R)-Carboxy-ethyl]-α-(S)-hexylglycine-(S)-N²-piperazic acid methyl amide;
N-[1(R)-Carboxy-ethyl]-α-(S)-heptylglycine-(S)-N²-piperazic acid methyl amide;
N-[1(R)-Carboxy-ethyl]-α-(S)-octylglycine-(S)-N²-piperazic acid methyl amide;
N-[1(R)-Carboxy-ethyl]-α-(S)-ethylphenylglycine-(S)-N²-piperazic acid methyl amide;
N-[1(R)-Carboxy-ethyl]-α-(S)-propylphenylclycine-(S)-N²-piperazic acid methyl amide;
N-[1(R)-Carboxy-ethylthiobenzyl]-α-(S)-isobutylglycine-(S)-N²-piperazic acid methyl amide;
N-[1(R)-Carboxy-ethylthiobenzyl]-α-(S)-hexylglycine-(S)-N²-piperazic acid methyl amide;
N-[1(R)-Carboxy-ethylthiobenzyl]-α-(S)-ethylphenylglycine-(S)-N²-piperazic acid methyl amide;
N-[1(R)-Carboxy-ethylthiobenzyl]-α-(S)-propylphenylglycine-(s)-N²-piperazic acid methyl amide;
N[1(R)-Carboxy-ethyloxybenzyl]-α-(S)-isobutylglycine-(s)-N²-piperazic acid methyl amide;
N[1(R)-Carboxy-ethyloxybenzyl]-α-(S)-hexylglycine-(S)-N²-piperazic acid methyl amide;
N-[1(R)-Carboxy-ethyloxybenzyl]-α-(S)-ethylphenylglycine-(S)-N²-piperazic acid methyl amide;
N[1(R)-Carboxy-ethyloxybenzyl]-α-(S)-propylphenylglycine-(S)-N²-piperazic acid methyl amide;
N[1(R)-Carboxy-4-(p-toluenesulfonyl)butyl]-α-(S)-phenethylglycyl-(S)-N²-piperazic acid methyl amide;
N[1(R)-Carboxyethyl]-α-[2-(4-phenylphenoxy)ethyl]-glycyl-(S)-N²-piperazic acid methyl amide;
2-[2(R)-[2-[1,1'-Biphenyl)yl]ethyl]-4-butyl-4(S)-carboxy-1-oxobutyl]-3(S)-methylaminocarbonyl-hexahydropyridazine;
2-[2(R)-[2-[1,1'-Biphenyl)yl]ethyl]-4-methyl-4(S)-carboxy-1-oxobutyl]-3(S)-methylaminocarbonyl-hexahydropyridazine;
2-[2(R)-[2-[1,1'-Biphenyl)yl]propyl]-4-butyl-4(S)-carboxy-1-oxobutyl]-3(S)-methylaminocarbonyl-hexahydropyridazine;
2-[2(R)-[2-(4-Propylphenyl)ethyl]-4-butyl-4(S)-carboxy-1-oxobutyl]-3(S)-methylaminocarbonyl-hexahydropyridazine;
2-[2(R)-[2-(4-Butylphenyl)ethyl]4-butyl-4(S)-carboxy-1-oxobutyl]-3(S)-methylaminocarbonyl-hexahydropyridazine;
2-[2(R)-[2-(4-t-Butylphenyl)ethyl]-4-butyl-4(S)-carboxy-1-oxobutyl]-3(S)-methylaminocarbonyl-hexahydropyridazine;
2-[2(R)-[2-[4-(4-Fluorophenyl)phenyl]ethyl]4-butyl-4(S)-carboxy 1-oxobutyl]-3(S)-methylaminocarbonyl-hexahydropyridazine;
2-[2(R)-[2-[4-(4-Fluorophenyl)phenyl]ethyl]-4-methyl-4(S)-carboxy-1-oxobutyl]-3(S)-methylaminocarbonyl-hexahydropyridazine;
2-[2(R)-[2-n-Octyl-4-methyl4(S)-carboxy-1-oxobutyl]-3(S)-methylaminocarbonyl-hexahydropyridazine;
2-[2(R)-[2-[(4-Thiazolyl)phenyl]ethyl]-4-butyl-4(S)-carboxy-1-oxobutyl]-3(S)-methylaminocarbonyl-hexahydropyridazine;
2-[2(R)-[2-[(4-Thiazolyl)phenyl]ethyl]-4-methyl-4(S)-carboxy-1-oxobutyl]-3(S)-methylaminocarbonyl-hexahydropyridazine;
2-[2(R)-[2-[(4-Thiazolyl)phenyl]ethyl]-4-[3-(phenylsulfonyl)propyl-4(S)-carboxy-1-oxobutyl]-3(S)-methylaminocarbonyl-hexahydropyridazine;
2-[2(R)-[2-[(4-Thiazolyl)phenyl]ethyl]-4-(3-phenylpropyl)-4(S)-carboxy-1-oxobutyl]-3(S)-methylaminocarbonyl-hexahydropyridazine;
2-[2(R)-[2-[(4-Oxazolyl)phenyl]ethyl]-4-butyl-4(S)-carboxy-1-oxobutyl]-3(S)-methylaminocarbonyl-hexahydropyridazine;
2-[2(R)-[2-[(4-Oxazolyl)phenyl]ethyl]-4-methyl4(S)-carboxy-1-oxobutyl]-3(S)-methylaminocarbonyl-hexahydropyridazine;
2-[2(R)-[2-[(4-Oxazolyl)phenyl]ethyl]-4-[3-(phenylsulfonyl)propyl-4(S)-carboxy-1-oxobutyl]-3(S)-methylaminocarbonyl-hexahydropyridazine;
2-[2(R)-[2-[(4-Oxazolyl)phenyl]ethyl]-4-(3-phenylpropyl)4(S)-carboxy-1-oxobutyl]-3(S)-methylaminocarbonyl-hexahydropyridazine;
2-[2(R)-[2-[4-(Dimethylamino)methylphenyl]ethyl]-4-butyl-4(S)-carboxy-1-oxobutyl]-3(S)-methylaminocarbonyl-hexahydropyridazine;
2-[2(R)-[2-[4-(Dimethylamino)methylphenyl]ethyl]-4-methyl-4(S)-carboxy-1-oxobutyl]-3(S)-methylaminocarbonyl-hexahydropyridazine;
2-[2(R)-[2-[4-(Dimethylamino)methylphenyl]ethyl]-4-[3-(phenylsulfonyl)propyl-4(S)-carboxy-1-oxobutyl]-3(S)-methylaminocarbonyl-hexahydropyridazine;
2[2(R)-[2-[4-(Dimethylamino)methylphenyl]ethyl]-4-(3-phenylpropyl)-4(S)-carboxy-1-oxobutyl]-3(S)-methylaminocarbonyl-hexahydropyridazine;
2-[2(R)-[2-[(4-Imidazolyl)phenyl]ethyl]-4-butyl-4(S)-carboxy-1-oxobutyl]-3(S)-methylaminocarbonyl-hexahydropyridazine;
2-[2(R)-[2-[(4-Imidazolyl)phenyl]ethyl]-4-methyl-4(S)-carboxy-1-oxobutyl]-3(S)-methylaminocarbonyl-hexahydropyridazine;
2-[2(R)-[2-[(4-Imidazolyl)phenyl]ethyl]-4-[3-(phenylsulfonyl)propyl-4(S)-carboxy-1-oxobutyl]-3(S)-methylaminocarbonyl-hexahydropyridazine;
2-[2(R)-[2-[(4-Imidazolyl)phenyl]ethyl]-4-[3-(phenylpropyl)-4(S)-carboxy-1-oxobutyl]-3(S)-methylaminocarbonyl-hexahydropyridazine;
HS(CH$_2$)$_2$-(S-D-Leu)-Phe-NHMe;
HS(S)CHMeCH$_2$-(S-D-Leu)-Phe-NHMe;
HS(S)CH(PhtNBu)CH$_2$-(S-D-Leu)-Phe-NHMe;
HS(S)CH(PhtNEt)CH$_2$-(S-D-Leu)-Phe-NHMe;
HS(1,2-cyclopentyl)(S-D-Leu)-Phe-NHMe Me—S(NH)₂—(CH₂-DL-Leu)-Trp-NHBn;
n-Bu—S(H)₂—(CH₂-DL-Leu)-Trp-NHBn;
n-Bu—S(NH)₂—(CH₂-DL-TyrOCH₃)-Trp-NHBn;
Me—RS—SO(NH)—(CH₂-L-Leu)-Phe-Ala-NH₂;
n-Bu—RS—SO(NH)—(CH₂-L-Leu)-Phe-Ala-NH₂;

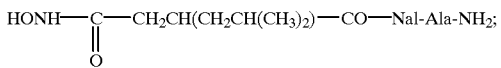
HONH—C(=O)—CH₂CH(CH₂CH(CH₃)₂)—CO—Nal-Ala-NH₂;

HO—NH—CO—CH₂—CH—(CH₂—CH(CH₃)₂—CO-Nal-Pro-NH₂;
HO—NH—CO—CH(CH₃—CH(CH₂)—CH(CH₃)₂)—CO-Nal-Ala-NH₂;

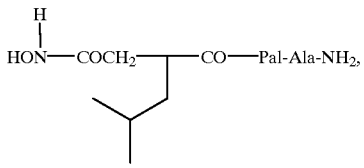
HON(H)—COCH₂—(CH(CH₂CH(CH₃)₂))—CO—Pal-Ala-NH₂, wherein Pal is 3-pyridylalanine;

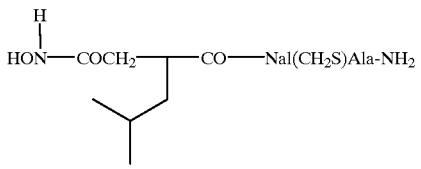
HON(H)—COCH₂—(CH(CH₂CH(CH₃)₂))—CO—Nal(CH₂S)Ala-NH₂

HO—NH—CO—CH₂—CH(CH₂CH(CH₃)₂)—CONal—(CH₂NH)-Ala-NH₂;

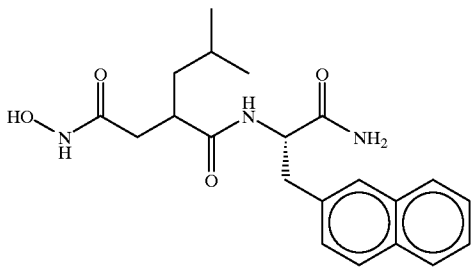

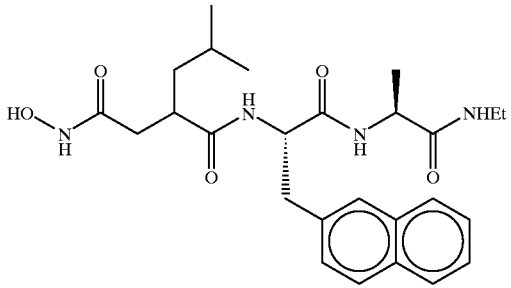

4-(1,3-Dihydro-1,3-dioxo-2H-benz[f]isoindol-2-yl)-2-(R)-[[3-methyl-1-(S)-[[(2-morpholin4-ylethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[methylamino]carbonyl]butyl]amino]-butanoic acid;
4-(1,3-Dihydro-1,3-dioxo-2H-benz[f]isoindol-2-yl)-2-(R)-[[3-methyl-1-(S)-[[(1H-imidazol-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(2-(phenyl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid;
4-(1,3-dihydro-1,3-dioxo-2H-benz[f]isoindol-2-yl)-2-(R)-[[3-methyl-1-(S)-[[(2-methyl-2H-tetrazo-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[2-(2-pyridin-3-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[1-(1H-tetrazol-5-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(6-oxo-1,6-dihydro-pyridazin-3-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(pyridin-4-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[2-(1H-imidazol4-yl)ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(pyridin-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-dimethylamino-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid;
4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid;
4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2,4-difluoro-benzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(4-methanesulfonylamino-benzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-methanesulfonylamino-benzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3,4-difluoro-benzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-trifluoromethyl-benzyl)amino]carbonyl]butyl]amino]-butanoic acid;

4-[2-(S)-1-(R)-Carboxy-3-(1,3-dioxo-1,3-dihydro-benzo[f]isoindol-2-yl)-propylamino]-4-methyl-pcentanoylaminomethyl)-benzoic acid;

4-(1,3-Dihydro-1,3-dioxo-2H-benz[f]isoindol-2-yl)-2-(R)-[[3-methyl-1-(S)-[[(2-hydroxy-1,1-bis-hydroxymethyl-ethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3,5-difluoro-benzyl)amino]carbonyl]butyl]amino]-butanoic acid;

4-(1,3-dihydro-1,3-dioxo-2H-benz[f]isoindol-2-yl)-2-(R)-[[3-methyl-1-(S)-[[benzylmethyl-amino]carbonyl]butyl]amino]-butanoic acid;

4-(1,3-dihydro-1,3-dioxo-2H-benz[f]isoindol-2-yl)-2-(R)-[[3-methyl-1-(S)-[[(2-dimethylaminoethyl)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1-azabicyclo[2.2.2]-oct-3(R)-amino]carbonyl]butyl]amino]-butanoic acid;

4-(1,3-Dihydro-1,3-dioxo-2H-benz[f]isoindol-2-yl)-2-(R)-[[3-methyl-1-(S)-[[(1-azabicyclo[2.2.2]oct-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-4-(S)-5-(R)-6-tetrahydrox-tetrahydra-pyran-2-(R)-ylmethyl)amino-carbonyl]butyl]amino]-butanoic acid;

4-(1,3-Dihydro-1,3-dioxo-2H-benz[f]isoindol-2-yl)-2-(R)-[[3-methyl-1-(S)-[[(N,N'-dimethyl-hydrazino)carbonyl]butyl]amino]-butanoic acid;

4-(1,3-Dihydro-1,3-dioxo-2H-benz[f]isoindol-2-yl)-2-(R)-[[3-methyl-1-(S)-[[(methylmethoxy)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(2-oxo-tetrahydro-thiophen-3-(S)-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydropyran-2-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[[benzyl(2-hydroxyethyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid;

4-(1,3-Dihydro-1,3-dioxo-2H-benz[f]isoindol-2-yl)-2-(R)-[[3-methyl-1-(S)-[4-methylpiperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[1-oxo-[1,4]thiazinane-4-carbonyl]butyl]amino]-butanoic acid;

4-(1,3-Dihydro-1,3-dioxo-2H-benz[f]isoindol-2-yl)-2-(R)-[[3-methyl-1-(S)-[morpholine-4-carbonyl]butyl]amino]-butanoic acid;

4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1]carbonyl]butyl]amino]-butanoic acid;

4-(1,3-Dihydro-1,3-dioxo-2H-benz[f]isoindol-2-yl)-2-(R)-[[3-methyl-1-(S)-[[(1-methyl-8-oxo-1,7-diazacyclotridec-9-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[methyl-1-methyl-piperidin-4-yl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]-amino]-butanoic acid;

4-(1,3-dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid;

4-(1,3-dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[2-(R)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[2-(S)-(pyridin-3-yl)-pyrrolidinecarbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(R)-phenyl-piperazine-1-carbonyl]butyl]amino]-butanoic acid;

4-(1,3-Dihydro-1,3-dioxo-2H-benz[f]isoindol-2-yl)-2-(R)-[[3-methyl-1-(S)-[3-oxo-2-(S)-phenyl-piperazine-1-carbonyl]butyl]amino]-butanoic acid; 4-(1,3-Dihydro-1,3-dioxo-2H-benz[f]isoindol-2-yl)-2-(R)-[[3-methyl-1-(S)-[(pyridine-3-carbonyl-hydrazino)carbonyl]butyl]amino]-butanoic acid;

4-(1,3-Dihydro-1,3-dioxo-2H-benz[f]isoindol-2-yl)-2-(R)-[[3-methyl-1-(S)-[[(benzenesulfonyl)amino]carbonyl]butyl]amino]-butanoic acid; 4-(1,3-Dihydro-1,3-dioxo-2H-benz[f]isoindol-2-yl)-2-(R)-[[3-methyl-1-(S)-[[(3-aminobenzyl)amino]carbonyl]butyl]amino]-butanoic acid;

4-(1,3-Dihydro-1,3-dioxo-2H-benz[f]isoindol-2-yl)-2-(R)-[[3-methyl-1-(S)-[[[4-(trifluoro-methanesulfonylamino)benzyl]amino]carbonyl]butyl]amino]-butanoic acid;

4-(1,3-Dihydro-1,3-dioxo-2H-benz[f]isoindol-2-yl)-2-(R)-[[3-methyl-1-(S)-[[[2-hydroxy-(R)-bicyclo[4.3.0]nona-3,6(1)-diene]amino]carbonyl]butyl]-amino]-butanoic acid;

4-(1,3-Dihydro-1,3-dioxo-2H-benz[f]isoindol-2-yl)-2-(R)-[[3-methyl-1-(S)-[[[2-hydroxy-(S)-bicyclo[4.3.0]nona-3,6(1)-diene]amino]carbonyl]butyl]-amino]-butanoic acid;

4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid;

4-(1,3-Dihydro-1,3-dioxo-2H-benz[f]isoindol-2-yl)-2-(R)-[[3-methyl-1-(S)-[(N-ethoxycarbonylmethyl-piperazine)-1-carbonyl]butyl]amino]-butanoic acid;

2-(R)-[1-(S)-(Benzylamino)carbonyl-3-methylbutylamino]4-(5-bromo-1,3-dioxo-1,3-dihydro-isoindol-2-yl)-butanoic acid;

2-(R)-[1-(S)-(Benzylamino)carbonyl-3-methylbutylamino]4-(5-propoxy-1,3-dioxo-1,3-dihydro-isoindol-2-yl)-butanoic acid;

2-(R)[1-(S)-(Benzylamino)carbonyl-3-methylbutylamino]-4-(5-nitro-1,3-dioxo-1,3-dihydro-isoindol-2-yl)-butanoic acid;

2-(R)[1-(S)-(Benzylamino)carbonyl-3-methylbutylamino]-4-(5-amino-1,3-dioxo-1,3-dihydro-isoindol-2-yl)-butanoic acid;

2-(R)[1-(S)-(Benzylamino)carbonyl-3-methyl butylamino]-4(5methyl1,3-dioxo-1,3-dihydro-isoindol-2-yl)-butanoic acid;

2-(R)-[1-(S)-(Benzylamino)carbonyl-3-methylbutylamino]-4-(5-methoxy-1,3-dioxo-1,3-dihydro-isoindol-2-yl)-butanoic acid;

2-(R)-[1-(S)-(Benzylamino)carbonyl-3-methylbutylamino]-4-(5-benzyloxy-1,3-dioxo-1,3-dihydro-isoindol-2-yl)-butanoic acid;

2-(R)[1-(S)-(Benzylamino)carbonyl-3-methylbutylamino]4-(5-phenyl-1,3-dioxo-1,3-dihydro-isoindol-2-yl)-butanoic acid;

2-(R)[1-(S)-(Benzylamino)carbonyl-3-methyl butylamino]-4-(1,3-dioxo-1,3-dhydro-isoindol-2-yl)-butanoic acid;

2-(R)-[1-(S)-(Benzylamino)carbonyl-3-methylbutylamino]4-(5-methanesulfonylamino-1,3-dioxo-1,3-dihydro-isoindol-2-yl)-butanoic acid;

2-(R)[1-(S)-(Benzylamino)carbonyl-3-methylbutylamino]4-(5-benzenesulfonylamino-1,3-dioxo-1,3-dihydro-isoindol-2-yl)-butanoic acid;

2-(R)[1-(S)-(Benzylamino)carbonyl-3-methyl butylamino]4-(5-hydroxy-1,3-dioxo-1,3-dihydro-isoindol-1,2-yl)-butanoic acid;

2-(R)-[[3-Methyl-1-(S)-[[(pyridin-3-ylmethyl)amino]carbonyl]-butyl]amino]-(1,3,5,7-tetraoxo-3,5,6-tetrahydro-1H-pyrolo[3,4-f]isoindol-2-yl)butanoic acid;

EtONHCONMe—CH$_2$CH(iBu)—CO—L-Trp-NHEt;
EtCONOEt—CH$_2$CH(iBu)—CO—L-Trp-NHEt;
n-PrCONOEt—CH$_2$CH(iBu)—CO—L-Trp-NHEt;
EtNHCONOMe—CH$_2$CH(iBu)—CO—L-Trp-NHEt;
MeNHCONOH—CH$_2$CH(iBu)—CO—L-Trp-NHEt;
EtONHCONMe—CH$_2$CH(iBu)—CO—L-Ala(2-naphthyl)-NHEt;
EtCONOH—CH$_2$CH(iBu)—CO—L-Ala(2-naphthyl)-NHEt;
n-PrCONOEt—CH$_2$CH(iBu)—CO—L-Ala(2-naphthyl)-NHEt;
EtNHCONOMe—CH$_2$CH(iBu)—CO—L-Ala(2-naphthyl)-NHEt;
MeNHCONOH—CH$_2$CH(iBu)—CO—L-Ala(2-naphthyl)-NHEt;
HONHCONHCH$_2$CH(iBu)—CO—L-TrpNHMe;
HONHCONHCH$_2$CH$_2$CH(iBu)—CO—L-TrpNHMe;
HONHCONHCH(iBu)—CO—L-TrpNHMe;
H$_2$NCON(OH)CH(iBu)—CO—L-TrpNHMe;
N(OH)CH$_2$CH(iBu)—CO—L-TrpNHMe;
H$_2$NCON(OH)CH$_2$CH$_2$CH(iBu)—CO -L-TrpNHMe;
CH$_3$CON(OH)CH(iBu)—CO—L-TrpNHMe;
CH$_3$CON(OH)CH$_2$CH(iBu)—CO—L-TrpNHMe;
CH$_3$CON(OH)CH$_2$CH$_2$CH(iBu)—CO—L-TrpNHMe;
NHOHCOCH$_2$CH(i-Bu)CO—L-Trp-NHMe;

HONHCONHCH$_2$CH(i-Bu)CONHCHCOOH,
|
R$^4$ or

ROOCCH$_2$CH(i-Bu)CONHCHCOOH;
|
R$^4$

N-{D,L-2-(Hydroxyaminocarbonyl)methyl-4-methylpentanoyl}-L-3-(2'-naphthyl)alanyl-L-alanine, 2-(amino)ethyl amide;

N-{D,L-2-(Hydroxyaminocarbonyl)methyl-4-methylpentanoyl}-L-3-amino-2-dimethylbutanoyl-L-alanine, 2-(amino)ethyl amide;

4(S)-[3-Hydroxyaminocarbonyl-2(R)-(2-methylpropyl) propanoyl]amino-1,2,3,4,5-tetrahydro-3H-2-benzazepin-3-one;

[4-(N-Hydroxyamino)-(2R)-isobutyl-3-methylsuccinyl]-L-phenylglycine-N-methylamide;

4(S)-[2(R)-[1(R)-Hydroxycarbamoyl-2-morpholinoethyl]-4-methylvaleryl]amino-1,2,4,5-tetrahydro-3H-2-benzazepine-3-one;

(1R,4S)-4-[(2R)-Hydroxycarbamoylmethyl-4-methylvaleryl]amino-3-oxo-1,2,4,5-tetrahydro-3H-2-benzazepine-1-carboxylic acid;

3-[2-(N-Methylcarbamoyl)ethylsulfinyl]-5-methylhexanohydroxamic acid;

N-[(2-Thenoylmercapto-3-methyl)-butanoyl]-homocysteine thiolactone;

N-[1(R)-Carboxy-ethyl]-α-(S)-(2-phenyl-ethyl)glycine-(L)-leucine, N-phenylamide;

N-[1(R)-Carboxy-ethyl]-α-(S)-(2-phenyl-ethyl)glycine-(L)-isoleucine, N-phenylamide;

N-[1(R)-Carboxy-ethyl]-α-(S)-(2-phenyl-ethyl)glycine-(L)-alanine, N-phenylamide;

N-[1(R)-Carboxy-ethyl]-α-(S)-(2-phenyl -ethyl)glycine-(L)-phenylalanine, N-phenylamide;

N-[1(R)-Carboxy-ethyl]-α-(S)-(2-phenyl-ethyl)glycine-(L)-serine-O-benzyl ether, N-phenylamide;

N-[1(R)-Carboxy-ethyl]-α-(S)-(2-phenyl-ethyl)glycine-(L)-tryptophan, N-phenylamide;

N[1(R)-Carboxy-ethyl]-α-(S)-(2-phenyl-ethyl)glycine-α-(S)-(2-phenylethyl)glycine, N-phenylamide;

N-[1(R)-Carboxy-ethyl]-α-(S)-(2-phenyl-ethyl)glycine-(L)-norleucine, N-phenylamide;

N-[1(R)-Carboxy-ethyl]-α-(S)-(2-phenyl-ethyl)glycine-(L)-valine, N-phenylamide;

N-[1(R)-Carboxy-ethyl]-α-(S)-(2-phenyl-ethyl)glycine-(L)-serine, N-phenylamide hydrochloride;

N-[1(R)-Carboxy-ethyl]-α-(S)-(2-phenyl-ethyl)glycine-(L)-asparagine, N-phenylamide;

N-[1(R)-Carboxy-ethyl]-α-(S)-(2-phenyl-ethyl)glycine-(L)-threonine, N-phenylamide hydrochloride;

N-[1(R)-Carboxy-ethyl]-α-(S)-(2-phenyl-ethyl)glycine-(L)-lysine, N-phenylamide;

N-[1(R)-Carboxy-ethyl]-α-(S)-(2-phenyl-ethyl)glycine-(L)-glutamic acid, N-phenylamide;

N-[1(R)-carboxy-ethyl]-α-(S)-(2-phenyl-ethyl)glycine-(L)-tyrosine, N-phenylamide hydrochloride;

N-[1(R)-Carboxy-5-(1,3-dioxo-isoindolin-2-yl)pentyl]-α-(S)-(2-phenyl-ethyl)glycine-(L)-leucine, N-phenylamide;

N-[1(R)-Carboxy-5-(1-oxo-isoindolin-2-yl)pentyl]-α-(S)-(2-phenyl-ethyl)-glycine-(S)-leucine, N-phenylamide hydrochloride;

N-[1(R)-Carboxy-5-(1-oxo-isoindolin-2-yl)pentyl]-α-(S)-(2-phenyl-ethyl)-glycine-(S)-arginine, N-phenylamide;
N-[1(R)-Carboxy-ethyl]-α-(S)-(2-(3-hydroxyphenyl)-ethyl) glycine-(S)-leucine, N-phenylamide hydrochloride;
N-[1(R)-Carboxy-ethyl]-α-(S)-(2-(4-methylphenyl)-ethyl) glycine-(S)-leucine, N-phenylamide hydrochloride;
N-[1(R)-Carboxy-ethyl]-α-(S)-(2-(2'-thienyl)ethyl)glycine-(L)-leucine, N-phenylamide;
N-[1(R)-Carboxy-ethyl]α-(S)-(2-(4-ethylphenyl)ethyl) glycine-(L)-leucine, N-phenylamide;
N-[1(R)-Carboxy-5-(1-oxo-isoindolin-2-yl)pentyl]-α-(S)-(2-(4-propylphenyl)ethyl)glycine-(L)-leucine, N-phenylamide;
N-[1(R)-Carboxy-ethyl]-α-(S)-(2-(4-chlorophenyl)ethyl) glycine-(L)-leucine, N-phenylamide;
N-[1(R)-Carboxy-ethyl]-α-(S)-(2-phenyl-ethyl)glycine-α-(S)-(2-cyclohexyl-ethyl)glycine, N-phenylamide;
N-[1(R)-Carboxy-ethyl]-α-(S)-(2-phenyl-ethyl)glycine-α-(S)-(cyclohexyl)glycine, N-phenylamide;
N-[1(R)-Carboxy-ethyl]-α-(S)-(2-phenyl-ethyl)glycine-α-(S)-(cyclohexylmethyl)glycine, N-phenylamide;
N-[1(R)-Carboxy-ethyl]-α-(S)-(2-phenyl-ethyl)glycine-(L)-β-naphthylalanine, N-phenylamide;
N-[1(R)-Carboxy-ethyl]-α-(S)-(2-phenyl-ethyl)glycine-(L)-α-naphthylalanine, N-phenylamide;
N-[1(R)-Carboxy-ethyl]-α-(S)-(2-phenyl-ethyl)glycine-[(L)-glutamic acid, α,L-bis-N-phenylamide;
N-[1(R)-Carboxy-ethyl]-α-(S)-(2-phenyl-ethyl)glycine-(L)-leucine, N-cyclohexylamide;
N-[(1(R)-Carboxy-ethyl)]-α-(S)-(2-phenyl-ethyl)glycine-α-(S)-(4-hydroxyphenyl-ethyl)glycine, N-phenylamide;
N-[1(R)-Carboxy-ethyl]-α-(S)-(2-phenyl-ethyl)glycine-(L)-phenylglycine, N-phenylamide;
N-[1(R)-Carboxy-ethyl]-α-(S)-(2-phenyl-ethyl)glycine-(L)-glutamic acid, N$_L$-benzylamide, N$_α$-phenylamide;
N-[1(R)-Carboxy-ethyl]-α-(S)-(2-phenyl-ethyl)glycine-(L)-ornithine, N-phenylamide;
N-[1(R)-Carboxy-ethyl]-α-(S)-(2-phenyl-ethyl)glycine-(L)-arginine, N-phenylamide;
N-[1(R)-Carboxy-ethyl]-α-(S)-(2-phenyl-ethyl)glycine-α-(S)-(3-phenylpropyl)glycine, N-phenylamide;
N-[1(R)-Carboxy-ethyl]-α-(S)-(2-phenyl-ethyl)glycine-α-(S)-n-octylglycine, N-phenylamide;
N-[1(R)-Carboxy-ethyl]-α-(S)-(2-phenyl-ethyl)glycine-(L)-leucine, N-(4-carboxyphenyl)amide;
N-[1(R)-Carboxy-ethyl]-α-(S)-(2-phenyl-ethyl)glycine-(L)-leucine, N-(4-trifluoromethylphenyl)amide;
N-[1(R)-Carboxy-ethyl]-α-(S)-(2-phenyl-ethyl)glycine-(L)-leucine, N-(3-pyridyl)amide;
N-[1(R)-Carboxy-ethyl]-α-(S)-(2-phenyl-ethyl)glycine-(L)-leucine, N-(benzothiazol-2-yl)amide;
N-[1(R)-Carboxy-ethyl]-α-(S)-(2-(4-n-propylphenyl)ethyl) glycine-(L) leucine, N-phenylamide;
N-[1(R)-Carboxy-ethyl]-α-(S)-(2-4-propylphenyl)ethyl) glycine-(L) arginine, N-phenylamide;
N-[1(R)-Carboxy-ethyl]-α-(S)-(2-(3,4-dimethylphenyl-ethyl)glycine-(L)-leucine, N-phenylamide;
(2-(((4-(1,3-Dihydro-1,3-dioxo-2H-isoindol-2-yl)-butyl) hydroxyphosphinyl)methyl)-4-phenylbutanoyl)-L-leucine, N-phenylamide;
(2-(((4-(1,3-Dihydro-1-oxo-2H-isoindol-2-yl)-butyl) hydroxyphosphinyl)methyl)-4-phenylbutanoyl)-L-leucine, N-phenylamide;
(2-(((4-(1,3-)-Dihydro-1-oxo-2H-isoindol-2-yl)butyl)(2-methyl-1-(1-oxopropoxy)propoxy)phosphinyl)methyl)-4-phenylbutanoyl)-L-leucine, N-phenylamide;
(2-((Hydroxy(methyl)phosphinyl)methyl)-4-phenylbutanoyl)-L-leucine, N-phenylamide;
[[Hydroxy[1(R)-[N-(N-acetyl-L-prolyl-L-alanyl)-amino]-ethyl]-phosphinyl]-methyl]-4-phenyl-butanoyl-L-leucyl, N-phenylamide;
[Hydroxy-[N-(N-(benzoyl)-L-prolyl)aminobutyl] phosphinyl]methyl]4-phenyl-butanoyl-L-leucine, N-phenylamide;
[Hydroxy-[2-Methylpropyloxycarbonyl-aminobutyl]-phosphinyl]methyl]-4-phenylbutanoyl-L-leucine, N-phenylamide;
[Hydroxy-1-Methylethylaminocarbonyl-aminobutyl]-phosphinyl]methyl]-4-phenylbutanoyl-L-leucine, N-phenylamide;
N-(2-Thiomethyl-4-phenylbutanoyl)-(L)-leucinamide;
N-(2-Thiomethyl-4-phenylbutanoyl)-(L)-leucine, N-phenylamide;
N-(2-Thiomethyl-4-phenylbutanoyl)-(L)-leucine, N-benzylamide;
N-(2-Thiomethyl-4-phenylbutanoyl)-(L)-leucine, N-(2-phenylethyl)amide;
N-(2-Thiomethyl-4-phenylbutanoyl)-(L)-phenylalaninamide;
N-(2-Thiomethyl-4-phenylbutanoyl)-(L)-phenylalanine N-phenylamide;
N-(2-Thiomethyl-4-phenylbutanoyl)-(L)-phenylalanine N-benzylamide;
N-(2-Thiomethyl-4-phenylbutanoyl)-(L)-phenylalanine-b-alanine;
2(R)-(2-(4-(1-n-Propyl)phenyl)ethyl)-1,5-pentanedioic acid 1-(L-leucine, N-phenylamide)amide;
2(R)-(2-(4-(1-n-Propyl)phenyl)ethyl)-1,5-pentanedioic acid 1-(2(S)-t-butyl)glycine, N-phenylamide)amide;
2(R)-(2-(4-(1-n-Propyl)phenyl)ethyl)-1,5-pentanedioic acid 1-(2(S)-t-butyl)glycine, N-(4-pyridylamide)amide;
2R)-(2-(4-(1-n-Propyl)phenyl)ethyl)-1,5-pentanedioic acid 1-(L-arginine, N-methylamide)amide;
2(R)-(2-(4-(1-n-Propyl)phenyl)ethyl)-4-methyl-1,5-pentanedioic acid 1-(L-leucine, N-phenylamide)amide;
2(R)-(2-(4-(1-n-Propyl)phenyl)ethyl)-4-methyl-1,5-pentanedioic acid 1-(2(S)-t-butyl)glycine, N-phenyl-amide)amide;
2(R)-(2-(4-(1-n-Propyl)phenyl)ethyl)-4-methyl-1,5-pentanedioic acid 1-(2(S)-(4-thiazolylmethyl)glycine, N-phenylamide)amide;
2(R)-(2-(4-(1-n-Propyl)phenyl)ethyl)-4-methyl-1,5-pentanedioic acid 1-(2(S)-(3-pyridylmethyl)glycine, N-phenylamide)amide;
2(R)-(2-(4-(1-n-Propyl)phenyl)ethyl)-4-methyl-1,5-pentanedioic acid 1-(L-leucine, N-(4-pyridyl)amide) amide;
2(R)-(2-(4-(1-n-Propyl)phenyl)ethyl)-4-methyl-1,5-pentanedioic acid 1-(2(S)-(2-pyridylmethyl)glycine, N-phenylamide)amide;
2(R)-(2-(4-(1-n-Propyl)phenyl)ethyl)-4-methyl-1,5-pentanedioic acid 1-(L-arginine, N-phenylamide)amide;
2(R)-(2-(4-(1-n-Propyl)phenyl)ethyl)-4-methyl-1,5-pentanedioic acid 1-(L-phenylalanine, N-4-pyridylamide) amide;
2(R)-(2-(4-(1-n-Propyl)phenyl)ethyl)-4-(1-(4-(N-(2-oxoisoindolinyl))-butyl))-1,5-pentanedioic acid 1-(L-leucine, N-phenylamide)amide;
2(R)-(2-(4-(1l-n-Propyl)phenyl)ethyl)-4-(1-(4-(N-(2-oxoisoindolinyl))-but-2-enyl))-1,5-pentanedioic acid 1-(L-leucine, N-phenylamide)amide;
2(R)-(2-(4-(4-Fluorophenyl)phenyl)ethyl)-4-methyl-1,5-pentanedioic acid 1-(L-leucine, N-phenylamide)amide;
2(R)-(2-(4-(Phenyl)phenyl)ethyl)-4-methyl-1,5-pentanedioic acid 1-(L-leucine, N-phenylamide)amide;

2(R)-(2-(4-(4-Methoxyphenyl)phenyl)ethyl)-4-methyl-1,5-pentanedioic acid 1-(L-leucine, phenylamide)amide;
2R)-(2-(4-(4-Methylphenyl)phenyl)ethyl)4-methyl-1,5-pentanedioic acid 1-(L-leucine, phenylamide)amide;
2(R)-(2-(4-(4-Hydroxy-n-butyl)-phenyl)-ethyl)-4-methylpentanedioic acid 1-(S-leucine, phenylamide)amide;
2(R),4(S)-(2-(4-(3-Hydroxy-n-propyl)phenyl)ethyl)-4-methyl-1,5-pentanedioic acid 1-(L-leucine, N-phenylamide)amide;
2(R)-(2-Phenylethyl)-4-methyl-1,5S-pentanedioic acid 1-(L-leucine, N-phenylamide)amide;
2(R)-(2-(4-(1-n-Propyl)phenyl)ethyl)-1,5-pentanedioic acid 1-(L-leucine, N-ethylamide)amide;
2(R)-(2-(4-(1-n-Propyl)phenyl)ethyl)-1,5-pentanedioic acid 1-(L-leucine, N-isopropylamide)amide;
2(R)-(2-(4-(1-n-Propyl)phenyl)propyl)-1,5-pentanedioic acid 1-(2(S)-tert-butyl-glycine, N-4-pyridyl)amide)amide;
2(R)-(3-(4-(1-n-Propyl)phenyl)propyl)-1,3-pentanedioic acid 1-(L-leucine, N-phenylamide)amide;
2(R)-(2-(4-(1-n-Propyl)phenyl)ethyl)-4-hexyl-1,5-pentanedioic acid 1-(L-leucine, N-phenylamide)amide;
2(R)-(2-(4-(1-n-Propyl)phenyl)ethyl)-4-butyl-1,5-pentanedioic acid 1-(L-leucine, N-phenylamide)amide;
2(R)-(2-(4-(1-n-Propyl)phenyl)ethyl)-4-(3-methylbenzyl)-1,5-pentanedioic acid 1-(L-leucine, N-phenylamide)amide;
2(R)-(2-(4-(1-n-Propyl)phenyl)ethyl)-4-(2-benzimidazolyl)butyl)-1,5-pentanedioic acid 1-(L-leucine, N-phenylamide)amide;
2(R)-(2-(4-(1-n-Propyl)phenyl)ethyl)-4-(2-benzthiazolyl)butyl)-1,5-pentanedioic acid 1-(L-leucine, N-phenylamide)amide;
2(R)-(2-(4-(1-n-Propyl)phenyl)ethyl)-4-(2-benzoxazolyl)butyl)-1,5-pentanedioic acid 1-(L-leucine, N-phenylamide)amide;
2(R)-(2-(4-(1-n-Propyl)phenyl)ethyl)-4-carboxy-1,9-nonanedioic acid 1-(L-leucine, N-phenylamide)amide 9-piperidineamide;
2(R)-(2-(4-(1-Propyl)phenyl)ethyl)-4-carboxy-1,9-nonanedioic acid 1-(L-leucine, N-methylamide)amide 9-phenylamide;
2(R)-(2-(4-(1-n-Propyl)phenyl)ethyl)-4-carboxy-1,9-nonanedioic acid 1-(L-leucine, N-methylamide)amide 9-tert-butylamide;
2(R)-(2-(4-(1-n-Propyl)phenyl)ethyl)-4-carboxy-1,9-nonanedioic acid 1-(L-leucine, N-methylamide)amide 9-benzylamide;
2(R)-(2-(4-(1-n-Propyl)phenyl)ethyl)-4-carboxy-1,9-nonanedioic acid 1-(L-leucine, N-methylamide)amide 9-morpholineamide;
2(R)-(2-(4-(1-n-Propyl)phenyl)ethyl)-4-carboxy-1,9-nonanedioic acid 1-(L-leucine, N-methylamide)amide 9-(1 (R)-phenylethyl)amide;
2(R)-(2-(4-(1-n-Propyl)phenyl)ethyl)-4-carboxy-1,9-nonanedioic acid 1-(L-leucine, N-methylamide)amide 9-(1(S)-phenylethyl)amide;
2(R)-(2-(4-(1-n-Propyl)phenyl)ethyl)-4-carboxy-1,9-nonanedioic acid 1-(L-leucine, N-methylamide)amide 9-(N-methyl-N-phenyl)amide;
2(R)-(2-(4-(1-n-Propyl)phenyl)ethyl)-4-carboxy-1,9-nonanedioic acid 1-(L-leucine, N-methylamide)amide 9-(N'-methylpiperazine)amide trifluoroacetic acid salt;
1(R)-(2-(4-(1-n-Propyl)phenyl)ethyl)-4-carboxy-1,9-nonanedioic acid 1-(L-leucine, N-methylamide)amide 9-(3-pyridyl)amide;
2(R)-(2-(4-(1-Propyl)phenyl)ethyl)-4-carboxy-1,9-nonanedioic acid 1-(L-leucine, N-methylamide)amide;
2(R)-(2-(4-(1-Propyl)phenyl)ethyl)-1,5-pentanedioic acid 1-(R)-(S-p-methoxybenzyl)penicillamine, N-phenylamide)amide;
2(R)-(2-(4-(1-Propyl)phenyl)ethyl)-1,5-pentanedioic acid 1-((R)-(S-p-methoxybenzyl)penicillamine sulfone, N-phenylamide)amide;
2-(2-(4-(1-Propyl)phenyl)ethyl)-4-(1-(4-(2-phthalimido))butyl)-1,5-pentandioic acid 1-(L-leucine, N-methylamide)amide;
2(R)-(2-(4-(1-n-Propyl)phenyl)ethyl)-4-(4-benzoylamino-1-butyl)-1,5-pentandioic acid 1-(L-leucine, N-methylamide)amide;
2(R)-(2-(4-(1-n-Propyl)phenyl)ethyl)-4-(4-pivaloylamino-1-butyl)-1,5-pentandioic acid 1-(L-leucine, N-methylamide)amide;
2(R)-(2-(4-(1-n-Propyl)phenyl)ethyl)-4-(4-phenylsulfonylamino-1-butyl)-1,5-pentandioic acid 1-(L-leucine, N-methylamide)amide;
2(R)-(2-(4-(1-n-Propyl)phenyl)ethyl)-4-(4-(N'-phenylureido)-1-butyl)-1,5-pentandioic acid 1-(L-leucine, N-methylamide)amide;
2(R)-(2-(4-(1-n-Propyl)phenyl)ethyl)-4-(4-phenyloxycarbonylamino-1-butyl)-1,5-pentandioic acid 1-(L-leucine, N-methylamide)amide;
2(R)-(2-(4-(1-n-Propyl)phenyl)ethyl)-4-(4-N'-benzyloxycarbonylamino-L-prolylamino)-1-butyl)-1,5-pentandioic acid 1-(L-leucine, N-methylamide)amide;
2(R)-(2-(4-(1-n-Propyl)phenyl)ethyl)-4-(4-cyclopentylamino-1-butyl)-1,5-pentandioic acid 1-(L-leucine, N-methylamide)amide;
2(R)-(2-(4-(1-n-Propyl)phenyl)ethyl)-4-(4-(2-carboxybenzoylamino)-1-butyl)-1,5-pentandioic acid 1-(L-leucine, N-methylamide)amide;
2(R)-(2-(4-(1-n-Propyl)phenyl)ethyl)-4-(4-cyano-1-butyl)-1,5-pentandioic acid 1-(L-leucine, N-phenylamide)amide;
N-[1(R)-Carboxyethyl]-α-(S)-(9-amino-n-nonyl)]glycine-(L)-leucine, N-phenylamide;
N-[1(R)-Carboxyethyl]-α-(S)-(n-octyl)]glycine-(L)-leucine, N-phenylamide;
N-[1(R)-Carboxyethyl]-α-(S)-(n-octyl)]glycine-(L)-arginine, N-phenylamide;
N-[1(R)-Carboxyethyl]-α-(S)-(9-amino-n-nonyl)]glycine-(L)-arginine, N-phenylamide;
N-[1(R)-Carboxyethyl]-α-(S)-(n-decyl)]glycine-(L)-leucine, N-phenylamide;
1-(2-(4-Propylphenyl)ethyl)cyclopentane-1,3-dicarboxylic acid 1-(L-leucine, N-phenylamide)amide;
1-(2-(4-Propylphenyl)ethyl)cyclohexane-1,3-dicarboxylic acid 1-(L-leucine, N-phenylamide)amide;
N-[1(R)-Carboxyethyl]-α-(S)-2-(4-fluorobiphenyl)-glycyl-(S)-2-(tert-butyl)glycine, N-phenylamide;
3S-[4-(N-Hydroxyamino)-2R-isobutylsuccinyl]amino-1-methoxy-3,4-dihydrocarbostyril;
3S-[4-(N-Hydroxyamino)-2R-isobutyl-3S-acetylthio-methylsuccinyl]amino-3,4-dihydrocarbostyril;
3S-[4-(N-Hydroxyamino)-2R-isobutyl-3S-methylsuccinyl]amino-1-methoxy-3,4-dihydrocarbostyril;
3S-[4-(N-Hydroxyamino)-2R-isobutylsuccinyl]amino-1-methoxymethyl-3,4-dihydrocarbostyril;
1-Carboxymethyl-3S-[4-N-hydroxyamino)-2R-isobutyl-3S-methylsuccinyl]amino-3,4-dihydrocarbostyril;
3S-[4-(N-Hydroxyamino)-2R-isobutylsuccinyl]amino-1-methoxyethoxymethyl-3,4-dihydrocarbostyril;
3S-[4-(N-Hydroxyamino)-2R-heptylsuccinyl]amino-1-methoxy-3,4-dihydrocarbostyril;

7-Chloro-3S-[4-(N-hydroxyamino)-2R-isobutylsuccinyl] amino 1-methoxymethyl-3,4-dihydrocarbostyril;

3S-[4-(N-Hydroxyamino)-2R-isobutylsuccinyl]amino-1-methoxyethyl-3,4-dihydrocarbostyril;

3S-[4-(N-Hydroxyamino)-2R-isobutylsuccinyl]amino-1-methoxyethyl-6,7-methylenedioxy-3,4-dihydrocarbostyril;

3R-[4-(N-Hydroxyamino)-2R-isobutylsuccinyl]amino-1-methoxyethyl-6,7-methylenedioxy-3,4-dihydrocarbostyril;

2-(R)-N-Hydroxy-2-[(4-methoxybenzenesulfonyl)(3-morpholin4-yl-3-oxopropyl)amino]-3-methylbutyramide;

2-(R)-2-[(2-Benzylcarbamoylethyl)(4-methoxy-benzenesulfonyl)amino]-N-hydroxy-3-methylbutyramide;

2-(R)-N-Hydroxy-2-((4-methoxybenzenesulfonyl) (2-[(pyridin-3-ylmethyl)carbamoyl]ethyl)amino)-3-methylbutyramide;

2-(R)-N-Hydroxy-2-([4-methoxybenzenesulfonyl]-[2-(methylpyridin-3-ylmethylcarbamoyl)ethyl]amino)-3-methylbutyramide;

4-(3-1-(R)[1-Hydroxycarbamoyl-2-methylpropyl)-(4-methoxybenzenesulfonyl)amino]propionyl)piperazine-1-carboxylic acid, tert-butyl ester;

2-(R)-N-Hydroxy-2-[(4-methoxybenzenesulfonyl)(3-oxo-3-piperazine-1-ylpropyl)amino)-3-methylbutyramide hydrochloride;

2-(R)-2-[(Benzylcarbamoylethyl)(4-methoxy-benzenesulfonyl)amino]-N-hydroxy-3-methylbutyramide;

2-(R)-N-Hydroxy-2-[(4-methoxybenzenesulfonyl][(2-morpholin-4-ylethylcarbamoyl)methyl]amino]-3-methylbutyramide;

2-(R)-N-Hydroxy-2-((4-methoxybenzenesulfonyl) ([(pyridin-3-ylmethyl)carbamoyl]methyl)amino)-3-methylbutyramide;

2-(R)-3,3,3,-Trifluoro-N-hydroxy-2-[(methoxy-benzenesulfonyl)(3-morpholin4-yl-3-oxopropyl)amino] propionamide;

2-(R)-N-Hydroxy-2-((4-phenoxybenzenesulfonyl)[2-methylpyridin-4-ylmethylcarbamoyl)ether]amino)-3-methylbutyramide;

4-[4-Methoxybenzenesulfonyl)(3-morpholin-4-yl-3-oxopropyl)amino]-1-methylpiperidene-4-carboxylic acid hydroxyamide;

2-(R)-N-Hydroxy-2-((4-methoxybenzenesulfonyl)-[3-(4-methylpiperazin-1-yl)-3-oxopropyl]amino)-3-methylbutyramide;

2-(R)-2-[(2-Carboxyethyl)(4-methoxybenzene-sulfonyl) amino]-N-hydroxy-3-methylbutyramide;

[(2-Carboxyethyl)(3,4-dimethoxybenzene-sulfonyl)amino]-N-hydroxy-acetamide;

2-(R)-2-[(2-Carbamoylethyl)(4-methoxybenzene-sulfonyl) amino]-N-hydroxy-3-methylbutyramide;

2-(R), 3-(R)-3, N-Dihydroxy-2-[(4-methoxybenzenesulfonyl)(3-oxo-3-piperidin-1-ylpropyl) amino]-butyramide;

2-(R)-N-Hydroxy-2-((4-methoxybenzenesulfonyl)[3-(methylpyridin-3-ylmethylcarbamoyl)propyl]amino)-3-methylbutyramide;

2-(R)-N-Hydroxy-2-((4-methoxybenzenesulfonyl)-[2-(methylcarboxymethylcarbamoyl)ethyl]amino)-3-methyl-butyramide;

2-(R)-N-Hydroxy-2-((4-methoxybenzenesulfonyl)[(1-methylpiperidin-4-ylcarbamoyl)methyl]amino)-3-methylbutyramide;

2-(R)-N-Cyclohexyl-N-hydroxy-2-((4-methoxy-benzenesulfonyl)-[3-(4-methylpiperazin-1-yl)-3-oxopropyl]amino)-acetamide;

2-(R)-N-Hydroxy-2-[(methoxybenzenesulfonyl)(3-morpholin-4-yl-[3-oxopropyl]amino)-4-(morpholin-4-yl) butyramide;

[4-N-Benzyloxyamino)-2(R)-isobutylsuccinyl]-L-leucyl-L-alanine ethyl ester;

[4-N-Benzyloxyamino)-2(R)-isobutylsuccinyl]-3(RS)-aminolaurolactam;

N$^a$-[4-(N-Benzyloxyamino)-2(R)-isobutylsuccinyl]-N$^e$-(N-benzyloxycarbonylglycyl)-L-lysyl-L-alanine ethyl ester;

[4-(N-Hydroxyamino)-2(RS)-isobutylsuccinyl]-L-leucylglycine ethyl ester;

[4-(N-Hydroxyamino)-2(RS)-isobutylsuccinyl]-L-leucylglycine isopentylamide;

[4-(N-Hydroxyamino)-2(RS)-isobutylsuccinyl]-L-valylglycine ethylamide;

[4-(N-Hydroxyamino)-2(RS)-isobutylsuccinyl]-L-leucylglycine ethylamide;

N$^a$-[4-(N-Hydroxyamino)-2(RS)-isobutylsuccinyl]-N$^e$-tert.butoxycarbonyl-L-lysylglycine ethylamide;

[4-(N-Hydroxyamino)-2(RS)-isobutylsuccinyl]-O-methyl-L-tyrosinylglycine ethyl ester;

[4-(N-Hydroxyamino)-2(RS)-isobutylsuccinyl]-O-methyl-L-tyrosinylglycine ethylamide;

[4-(N-Hydroxyamino)-2(RS)-isobutylsuccinyl]-L-leucyl-L-alanine ethyl ester;

[4-(N-Hydroxyamino)-2(RS)-isobutylsuccinyl]-L-leucylglycine isopentyl ester;

[4-N-Hydroxyamino)-2(R)-propylsuccinyl]-L-leucylglycine ethyl ester;

[4-(N-Hydroxyamino)-2(RS)-sec.butylsuccinyl]-L-leucylglycine ethyl ester;

[4-(N-Hydroxyamino)-2(R)-isobutylsuccinyl]-L-leucyl-L-alanine;

[4-(N-Hydroxyamino)-2(RS)-isobutylsuccinyl]-L-leucylglycine methyl ester;

[4-(N-Hydroxyamino)-2(RS)-isobutylsuccinyl]-L-leucylsarconsine ethyl ester;

[4-(N-Hydroxyamino)-2(RS)-isobutylsuccinyl]-L-leucyl-L-proline ethyl ester;

[4-(N-Hydroxyamino)-2(RS)-isobutylsuccinyl]-L-leucine-L-alanine isopropyl ester;

[4-(N-Hydroxyamino)-2(RS)-isobutylsuccinyl]-L-leucine-2-oxopropylamide;

[4-(N-Hydroxyamino)-2(RS)-isobutylsuccinyl]-L-leucine-2-methoxyethylamide;

[4-(N-Hydroxyamino)-2(RS)-isobutylsuccinyl]-L-leucine-2,2-dimethoxyethylamide;

N$^a$-[4-(N-Hydroxyamino)-2(R)-isobutylsuccinyl]-N$^e$-glycyl-L-lysine methylamide;

N$^a$-[4-(N-Hydroxyamino)-2(R)-isobutylsuccinyl]-N$^e$-(4-carboxybenzoyl)-L-lysyl-L-alanine ethyl ester;

N$^a$-[4-(N-Hydroxyamino)-2(R)-isobutylsuccinyl]N$^e$-(4-carboxybenzoyl)-L-lysyl-L-aline;

[4-(N-Hydroxyamino)-2(R)-isobutylsuccinyl]-3(RS)-aminooctahydro-2H-azonin-2-one;

[4-(N-Hydroxyamino)-3(S)-methyl-2(R)-isobutyl-succinyl]-L-leucylglycine ethyl ester;

[(3-Aminophthalimido)methyl][(RS)-4-methyl-2-[[(S)3-methyl-1-(methylcarbamoyl)butyl]carbamoyl]pentyl] phosphinic acid;

[(RS)4-Methyl-2-[[(S)-3-methyl-1-(methyl-carbamoyl) butyl]carbamoyl]pentyl](1,8-naphthalenedicarboximidomethyl)-phosphinic acid;

[(R or S)-4-Methyl-2-[[(R or S)-2-oxo-3-azacyclotridecyl] carbamoyl]pentyl](1,8-naphthalenedicarboximidomethyl)phosphinic acid;

N-[N-[(R or S)-2[[[[[N-[1-(Benzyloxy)carbonyl]-L-prolyl]-L-leucyl]amino]methyl]hydroxyphosphinyl]-methyl]-4-methylvaleryl]-L-leucyl]-L-alanine;

[[1,4-Dihydro-2,4-dioxo-3(2H)-quinazolinyl]-methyl][[(R or S)-4-methyl-2-[[(R or S)-2-oxo-3-azacyclotridecyl]carbamoyl]pentyl]phosphinic acid;

$N^2$-[(R)-Hydroxycarbamoylmethyl]-4-methylvaleryl]-$N^1$,3-dimethyl-L-valinamide;

$N^2$-[2(R or S)-[[[(5-Bromo-2,3-dihydro-6-hydroxy)-1,3-dioxo-1H-benz[d,e]isoquinol-2-yl)methyl]-[(hydroxy)phosphinyl]methyl]-4-methylvaleryl]-$N^1$,3-dimethyl-L-valinamide;

$N^2$-[(R or S)-[[(R)-(Amino)[(5-bromo-2,3-dihydro-6-hydroxy-1,3-dioxo-1H-benz[d,e]isoquinol-2-yl)methyl](hydroxy)-phosphinyl]methyl]4-methylvaleryl]-$N^1$,3-dimethyl-L-valinamide hydrobromide;

$N^2$-[2(R or S)-1(S)-(Hydroxycarbamoyl)ethyl-4-methylvaleryl]-$N^1$,3-dimethylvalinamide;

$N^2$-[2(R)[1(R or S)-(Hydroxycarbamoyl)-2-phthalimidoethyl]-4-methylvaleryl]-$N^1$,3-dimethyl-L-valinamide;

$N^2$-[2(R)[1(R or S)-(Hydroxycarbamoyl)-4-(methoxycarbonyl)butyl]-4-methylvaleryl]-$N^1$,3-dimethyl-L-valinamide;

$M^2$-[2(R)-[1(R or S)-(Hydroxycarbamoyl)-4-phenyl-butyl]-4-methylvaleryl]-$N^1$,3-dimethyl-L-valinamide;

$N^2$-[2(R)-[1(R or S)-(Hydroxycarbamoyl)-2-succinimidoethyl]-4-methylvaleryl]-$N^1$,3-dimethyl-L-valinamide;

4-[2(R)[1(R or S)-(Hydroxycarbamoyl)-2-phthalimidoethyl]-4-methylvaleryl]morpholine;

4-[2(R)-[1(R or S)-(Hydroxycarbamoyl)-2-phthalimidoethyl]-4-methylvaleryl]tetrahydro-1,4-thiazine;

1-[2(R)[1(R or S)-(Hydroxycarbamoyl)-2-phthalimidoethyl]-4-methylvaleryl]-4-piperidinol;

1-[2(R)-[1(R or S)-(Hydroxycarbamoyl)-2-(1,2-dimethyl-3,5-dioxo-1,2,4-triazolidin-4-yl)ethyl]-4-methylvaleryl)piperidine;

4-[2(R)-[1(R or S)-(Hydroxycarbamoyl)-2-(3-methyl-2,5-dioxo-1-imidazolidinyl)ethyl]-4-methylvaleryl]tetrahydro-1,4-thiazine;

Hexahydro-2-[2(R)[1(R or S)-(hydroxycarbamoyl)-2-phthalimidoethyl]-4-methylvaleryl]-N-methyl-3(S)-pyridazinecarboxamide;

1-[2(R)-(R or S)-(Hydroxycarbamoyl)-2-(3,4,4-trimethyl-2,5-dioxo-1-imidazolidinyl)ethyl]-4-methylvaleryl]-4-piperidinol;

[4-(N-Hydroxyamino)-2(R or S)-heptylsuccinyl]-L-leucyl-L-leucine ethylamide;

[4-(N-Hydroxyamino)-2(R or S)-nonylsuccinyl]-L-leucyl-L-leucine ethylamide;

[4-(N-Hydroxyamino)-2(R or S)-heptyl-3(S)-methylsuccinyl]-L-leucyl-L-leucine ethylamide;

[4-(N-Hydroxyamino)-2(R)-heptyl-3(R or S)-(phthalimidomethyl)succinyl]-L-leucyl-L-leucine ethylamide;

[4-(N-Hydroxyamino)-2(RS)-nonylsuccinyl]-L-tert.butylglycine methylamide;

[4-(N-Hydroxyamino)-2(RS)-heptylsuccinyl]-L-phenylalanine methylamide;

[4-(N-Hydroxyamino)-2(R)-heptyl-3(R or S)-phthalimidomethyl)succinyl]-L-tert.butylglycine methylamide;

[4-(N-Hydroxyamino)-2(R)-heptyl-3(R or S)-(3-phenylpropyl)-succinyl]-L-leucyl-L-leucine ethylamide;

[4-(N-Hydroxyamino)-2(RS)-heptylsuccinyl]-L-leucine methylamide;

[4-(N-Hydroxyamino)-2(RS)-heptylsuccinyl]-L-leucine neopentylamide;

[4-(N-Hydroxyamino)-2(RS)-heptylsuccinyl]-L-alanyl-L-leucine ethylamide;

[4-(N-Hydroxyamino)-2(RS)-heptylsuccinyl]-L-($N^e$-phthaloyl)-lysyl-L-leucine ethylamide;

[4-(N-Hydroxyamino)-2(RS)-undecylsuccinyl]-L-leucyl-L-leucine ethylamide;

[4-(N-Hydroxyamino)-2(RS)-heptylsuccinyl]-L-phenylalanyl-L-leucine ethyl amide;

[4-(N-Hydroxyamino)-2(RS)-heptylsuccinyl]-L-nonalyl-L-leucine ethylamide;

[4-(N-Hydroxyamino)-2(RS)-heptylsuccinyl]-phenylalanine tert.butylamide;

[4-(N-Hydroxyamino)-2(RS)-heptylsuccinyl]-L-tertbutylglycine methylamide;

[4-(N-Hydroxyamino)-2(RS)-heptylsuccinyl]-L-neopentylglycine methylamide;

[4-(N-Hydroxyamino)-2(RS)-heptylsuccinyl]-L-homophenylalanyl-L-leucine ethylamide;

[4-(N-Hydroxyamino)-2(RS)-heptylsuccinyl]-L-cyclohexylalanine methylamide;

[4-(N-Hydroxyamino)-2(RS)-isooctylsuccinyl]-L-phenylalanine methylamide;

[4-(N-Hydroxyamino)-2(R)-heptylsuccinyl]-L-neonpentylglycine methylamide;

[4-(N-Hydroxyamino)-2(R)-heptylsuccinyl]-(D or L)-β,β-dimethylphenylalanine methylamide;

[4-(N-Hydroxyamino)-2(R)-heptylsuccinyl]-(D or L)-erthro-β-methylphenylalanine methylamide;

[4-(N-Hydroxyamino)-2(R)-heptylsuccinyl]-DL-erthro-β-methylphenylalanine methylamide;

[4-(N-Hydroxyamino)-2(R)-heptyl-3(R or S)-[(3-methyl-2,5-dioxo-1-imidazolidinyl)methyl]succinyl]-L-leucyl-L-leucine ethylamide;

N2-[3-Cyclobutyl-2(R or S)-[(hydroxycarbamoyl)-methyl]-propionyl]-N1,3-dimethyl-L-valinamide;

N2-[3-Cyclopropyl-2(R or S)-[(hydroxycarbamoyl)-methyl]-propionyl]-N1,3-dimethyl-L-valinamide;

N2-[3-Cyclopentyl-2(R or S)-[(hydroxycarbamoyl)-methyl]-propionyl3-N1,3-dimethyl-L-valinamide;

N2-[3-Cyclopropyl-2(R)-[1(R or S)-[(hydroxy-carbamoyl)-2-(3,4,4-trimethyl-2,5-dioxo-1-imidazolidinyl)ethyl]propionyl]-N1,3-dimethyl-L-valinamide;

N2-[3-Cyclopropyl-2(R)-[1(R or S)-[(hydroxy-carbamoyl)-4-phenylbutyl)]propionyl]-$N^1$,3-dimethyl-L-valinamide;

N2-[3-Cyclobutyl-2(R)[1(R or S)-(hydroxy-carbamoyl)-4-phenylbutyl]propionyl]-N1,3-dimethyl-L-valinamide;

N2-[3-Cyclopentyl-2(R)[1(R or S)-(hydroxycarbamoyl)-4-phenylbutyl]propionyl]-N1,3-dimethyl-L-valinamide;

1-[3-Cyclopropyl-2(R)-[1(R or S)-(hydroxy-carbamoyl)-2-(3,4,4-trimethyl-2,5-dioxo-1-imidazolidinyl)ethyl]propionyl]piperidine;

1-[3-Cyclopropyl-2(R)[1(R or S)-(hydroxy-carbamoyl)-2-(3,4,4-trimethyl-2,5-dioxo-1-imidazolidinyl)ethyl]propionyl]-4-piperidinol;

1-[3-Cyclobutyl-2(R)[1(R or S)-(hydroxy-carbamoyl)-2-(3,4,4-trimethyl-2,5-dioxo-1-imidazolidinyl)ethyl]propionyl]piperidine;

1-[3-Cyclobutyl-2(R)[1(R or S)-(hydroxy-carbamoyl)-2-(3,4,4-trimethyl-2,5-dioxo-1-imidazolidinyl)ethyl]propionyl]-4-piperidinol;

1-[3-Cyclopentyl-2(R)[1(R or S)-(hydroxy-carbamoyl)-2-(3,4,4-trimethyl-2,5-dioxo-1-imidazolidinyl)ethyl]propionyl]-4-piperidinol;

1-[3-Cyclopentyl-2(R)[1(R or S)-(hydroxy-carbamoyl)-2-(3,4,4-trimethyl-2,5-dioxo-1-imidazolidinyl)ethyl]propionyl]piperidine;

3-[3-Cyclobutyl-2(R)-[1(R or S)-(hydroxycarbamoyl)-2-(3,4,4-trimethyl-2,5-dioxo-1-imidazolidinyl)ethyl]propionyl]-3-azabicyclo[3.2.2]nonane;

3-[3-Cyclopropyl-2(R)-[1(R or S)-(hydroxy-carbamoyl)-2-(3,4,4-trimethyl-2,5-dioxo-1-imidazolidinyl)ethyl]propionyl]-3-azabicyclo[3.2.2]nonane;

3-[3-Cyclopentyl-2(R)[1(R or S)-(hydroxy-carbamoyl)-2-(3,4,4-trimethyl-2,5-dioxo-1-imidazolidinyl)ethyl]propionyl]-3-azabicyclo[3.2.2]nonane;

1-[3-Cyclohexyl-2(R)-[1(R or S)-(hydroxycarbamoyl)-2-(3,4,4-trimethyl-2,5-dioxo-1-imidazolidinyl)ethyl]propionyl]piperidine;

4-[3-Cyclopentyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine;

4-[3-Cyclopentyl-2(R)[1(R or S)-(hydroxycarbamoyl)-2-(3,4,4-trimethyl-2,5-dioxo-1-imidazolidinyl)ethyl]propionyl]tetrahydro-1,4-thiazine S,S-dioxide;

4-[3-Cyclobutyl-2(R)-[1(R or S)-(hydroxycarbamoyl)-2-(3,4,4-trimethyl-2,5-dioxo-1-imidazolidinyl)ethyl]propionyl]tetrahydro-1,4-thiazine;

3-[3-Cyclopentyl-2(R)-[1(R or S)-(hydroxycarbamoyl)-2-(3,4,4-trimethyl-2,5-dioxo-1-imidazolidinyl)ethyl]propionyl]-5,5-dimethyl-N-propyl-[4(R)-thiazolidinecarboxamide;

4-[3-Cyclopentyl-2(R)-[1(R or S)-(hydroxycarbamoyl)-2-(3,4,4-trimethyl-2,5-dioxo-1-imidazolidinyl)ethyl]propionyl]morpholine;

3-[3-Cyclopentyl-2(R)-[1(R or S)-(hydroxy-carbamoyl)-2-(3,4,4-trimethyl-2,5-dioxo-1-imidazolidinyl)ethyl]propionyl]-N,5,5-trimethyl4(R)-thiazolidinecarboxamide;

4-[3-Cyclobutyl-2(R)-[1(R or S)-(hydroxy-carbamoyl)-2-(3,4,4-trimethyl-2,5-dioxo-1-imidazolidinyl)ethyl]propionyl]-4-phenylpiperazine;

4-[3-Cyclobutyl-2(R)[1(R or S)-(hydroxy-carbamoyl)-2-(3,4,4-trimethyl-2,5-dioxo-1-imidazolidinyl)ethyl]propionyl]morpholine;

1-[3-Cyclobutyl-2(R)[1(R or S)-(hydroxy-carbamoyl)-2-(3,4,4-trimethyl-2,5-dioxo-1-imidazolidinyl)ethyl]propionyl]pyrrolidine;

8-[3-Cyclobutyl-2(R)-[1(R or S)-(hydroxycarbamoyl)-2-(3,4,4-trimethyl-2,5-dioxo-1-imidazolidinyl)ethyl]propionyl]-1,4-dioxo-8-azaspiro[4,5]decane;

1-[3-Cyclobutyl-2(R)[1(R or S)-(hydroxycarbamoyl)-2-(3,4,4-trimethyl-2,5-dioxo-1-imidazolidinyl)ethyl]propionyl]-4-methoxypiperidine;

1-[3-Cyclobutyl-2(R)-[1(R or S)-(hydroxycarbamoyl)-2-(3,4,4-trimethyl-2,5-dioxo-1-imidazolidinyl)ethyl]propionyl]octahydroazocine;

1-[3-Cyclobutyl-2(R)-[1(R or S)-(hydroxycarbamoyl)-2-(5,5-dimethyl-2,4-dioxo-3-oxazolidinyl)ethyl]propionyl]piperidine;

1-[3-Cyclobutyl-2(R)[1(R or S)-(hydroxycarbamoyl)-2-(3,4,4-trimethyl-2,5-dioxo-1-imidazolidinyl)ethyl]propionyl]hexahydroazepine;

1-[3-Cyclobutyl-2(R)-[2-(hexahydro-1,3-dioxo-pyrazolo[1,2-a][1,2,4]-triazol-2-yl)-1(R or S)-(hydroxycarbamoyl)ethyl]propionyl]piperidine;

1-[3-Cyclobutyl-2(R)-[1(R or S)-(hydroxycarbamoyl)-2-phthalimidoethyl]propionyl]piperidine;

2-[2(R)[1(R or S)-(Hydroxycarbamoyl)-4-phenylbutyl]nonanoyl]hexahydro-N-methyl-3(S)-pyridazinecarboxamide;

N-Cyclohexyl-hexahydro-2-[2(R)-[1(RS)-(hydroxycarbamoyl)4-phenylbutyl]nonanoyl]-3(S)-pyridazinecarboxamide;

Hexahydro-2-[2(R)[1(RS)-(hydroxycarbamoyl)4-phenylbutyl]nonanoyl]-N-(2,2,6,6-tetramethyl-4-piperidinyl)-3(S)-pyridazinecarboxamide;

1-[2(R)-[1(R or S)-Hydroxycarbamoyl)-4-phenylbutyl]nonanoyl]piperidine;

N2-[2(R)-[1(RS)-(Hydroxycarbamoyl)-2-(3,4,4-trimethyl-2,5-dioxo-1-imidazolidinyl)ethyl]nonanoyl]-N1-methyl-L-prolinamide;

1-[2(R)-[1(R or S)-(Hydroxycarbamoyl)-2-(3,4,4-trimethyl-2,5-dioxo-1-imidazolidinyl)ethyl]nonanoyl]piperidine;

Hexahydro-2-[2(R)- (R or S)-(hydroxycarbamoyl)-2-(3,4,4-trimethyl-2,5-dioxo-1-imidazolidinyl)ethyl]nonanoyl]-N-methyl-3(S)-pyridazinecarboxamide;

Hexahydro-2-[2(R or S)-1(S)-(hydroxycarbamoyl)-3-phenylpropyl]undecanoyl]-N-methyl-3(S)-pyridazinecarboxamide;

Hexahydro-2-[2(R or S)-[1 (S)-(hydroxycarbamoyl)-3-phenylpropyl]undecanoyl]-N-methoxy-N-methyl-3(S)-pyridazinecarboxamide;

Hexahydro-2-[2(R or S)-[(1(S)-(hydroxycarbamoyl)-3-phenylpropyl]undecanoyl]-N-(1,2,2,6,6-pentamethyl4-piperidinyl)-3(S)-pyridazine-carboxamide;

Hexahydro-2-[2(R or S)-1(S)-(hydroxycarbamoyl)ethyl]undecanoyl]-N-methyl-3(S)-pyridazinecarboxamide;

Hexahydro-2-[2(R or S)-1(S)-(hydroxycarbamoyl)-3-phenylpropyl]nonanoyl]-N-methyl-3(S)-pyridazinecarboxamide;

Hexahydro-2-[2(R or S)-1(S)-(hydroxycarbamoyl)ethyl]nonanoyl]-N-methyl-3(S)-pyridazinecarboxamide;

1-[2(R or S)-[1(S)-(Hydroxycarbamoyl)ethyl]undecanoyl]piperidine;

1-[2-(R or S)-[1(S)-(hydroxycarbamoyl)-3-phenylpropyl]undecanoyl]piperidine;

Hexahydro-2-[2(R or S)-[1(S)-(hydroxycarbamoyl)-3-phenylpropyl]undecanoyl]-N-(2,2,6,6-tetramethyl-4-piperidinyl)-3(S)-pyridazinecarboxamide;

Hexahydro-2-[2(R or S)-[1(S)-(hydroxycarbamoyl)ethyl]undecanoyl]-N-(2,2,6,6-tetramethyl-4-piperidinyl)-3(S)-pyridazinecarboxamide;

1-[2(R or S)-[1(S)-(hydroxycarbamoyl)-4-phenylbutyl]undecanoyl]piperidine;

4-[2(R or S)-[1(S)-(hydroxycarbamoyl)-4-phenylbutyl]undecanoyl]morpholine;

1-(Benzyloxycarbonyl)-hexahydro-2-[2(R)-[(R or S)-(hydroxycarbamoyl)-4-phenylbutyl]nonanoyl]-N-α(S)-methylbenzyl)-3(S)-pyridazinecarboxamide;

N-[(2R)-2-[2'-(Hydroxyamino)-2'-(oxo)ethyl]-5-(carboxy)pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2''-(Hydroxyamino)-2''-(oxo)ethyl]-6'-(hydroxy)hexanoyl]amino-3,3-dimethylbutanoic acid N-methylamide;

(2S)-N-2-[(2'R)-2'-[2''-(Hydroxyamino)-2''-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'-oxobutylamino)hexanoyl]-L-phenylalanine N-methylamide;

2(S)-N-2-[(2'R)-2'-[2''-(Hydroxyamino)-2''-(oxo)ethyl]-6'-(oxo)-6'-(propylamino)hexanoyl]amino-3,3-dimethylbutanoic acid N-methylamide;

N-[(2R)-2-[(1'S)-1'-(Methyl)-2'-(hydroxyamino)-2'-(oxo)ethyl]-6-(phenylmethoxy)hexanoyl]-L-phenylalanine N-methylamide;

N-[(2R)-2-[(1'S)-1'-(Methyl)-2'-(hydroxyamino)-2'-(oxo)ethyl]-6-(oxo)-6-(propylamino)hexanoyl]-L-phenylalanine N-methylamide;

(2S)-N-2[(2'R)-[(1"R)-1"-(1,3-Dihydro-1,3-dioxo-2H-isoindol-2-yl)methyl-2"-(hydroxyamino)-2"-(oxo)ethyl]-6'-(phenylmethoxy)hexanoyl]amino-3,3-dimethylbutanoic acid N-methylamide;

N-[(2R)-2-[2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-2-phenylethylamide;

(2S)-N-2-[(2'R)-2'-[(1"S)-1"-(Methyl)-2"-(hyroxyamino)-2"-(oxo)ethyl]-6'-(oxo)-6'-(propylamino)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-(4'-sulfamoyl)phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

N-[2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

(2S)-N-2'-[(2'R)-2'-[2"-(Hydroxyamino)-2"-(oxo)ethyl]-6'-[(4-methoxy)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl)phenylethylamide;

(2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl)phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-methylamide;

(2S)-N-2-[(2'R)-2'-[(1"S)-1"-(2-Methylpropyl)-2"-(hydroxyamino)-2"-(oxo)ethyl]-6-(phenylmethoxy)hexanoyl]amino-3,3-dimethylbutanoic acid N-methylamide;

N-[(2R)-2-[2'-(Hydroxyamino)-2'-(oxo)ethyl]-6-(phenoxy)hexanoyl]-L-phenylalanine N-methylamide;

N-[(2R)-2-[2'-(Hydroxyamino)-2'-(oxo)ethyl]-7-(phenoxy)heptanoyl]-L-phenylalanine N-methylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)-phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylalanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl)-6'-[(3-methylphenoxy)hexanoyl]amino-3,3-dimethylbutanoic acid N-methylamide;

(2S)-N-2'-[(2'R)-2'-(carboxymethyl)-6'-(3-methylphenoxy)hexanoyl]amino-3,3-dimethylbutanoic acid N-methylamide;

N-[(2R)-2-[2'-(Hydroxyamino)-2'-(oxo)ethyl]-5-(carboxy)pentanoyl]-L-phenylalanine N-methylamide;

N-[(2R)-2-[2'-(Hydroxyamino)-2'-(oxo)ethyl]-6-(phenylmethoxy)hexanoyl]-L-phenylalanine N-methylamide;

N-[(2R)-2-[2'-(Hydroxyamino)-2'-(oxo)ethyl]-6-(propylamino)-6-(oxo)hexanoyl]-L-phenylalanine N-methylamide;

N-[(2R)-2-[2'-(Hydroxyamino)-2'-(oxo)ethyl]-(6RS)-6-(hydroxy)heptanoyl]-L-phenylalanine N-methylamide;

(2S)-N-2-[(2'R)-2'-[2"-(Hydroxyamino)-2"-(oxo)ethyl]-6'-(hydroxy)hexanoyl]amino-3,3-dimethylbutanoic acid N-methylamide;

(2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide;

N-[(2'R)-2-[2'-(Hydroxyamino)-2'-(oxo)ethyl]-6-(4'-oxobutylamino)hexanoyl]-L-phenylalanine N-methylamide;

2(S)-N-2-[(2'R)-2'-[2"-(Hydroxyamino)-2"-(oxo)ethyl]-6'-(oxo)-4'-(propylamino)hexanoyl]amino-3,3-dimethylbutanoic acid N-methylamide;

N-[(2R)-2-[(1'S)-1'-(Methyl)-2'-(hydroxyamino)-2'-(oxo)ethyl]-6-phenylmethoxy)hexanoyl]-L-phenylalanine N-methylamide;

N-[(2R)-2-[(1'S)-1'-(Methyl)-2'-(hydroxyamino)-2'-(oxo)ethyl]-6-(oxo)- (propylamino)hexanoyl]-L-phenylalanine N-methylamide;

(2S)-N-2[(2'R)-[(1"R)-1"-(1,3-Dihydro-1,3-dioxo-2H-isoindol-yl)methyl-2"-(hydroxyamino)-2"-(oxo)ethyl]-6'-(phenylmethoxy)hexanoyl]amino-3,3-dimethylbutanoic acid N-methylamide;

N-[(2R)-2-[2'-(Hydroxyamino)-2'-(oxo)ethyl]-6-(oxo)-6-(propylamino)hexanoyl]-L-phenylalanine N-2-phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-2-phenylethylamide;

(2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-phenylethylamide;

(2S)-N-2-[(2'R)-2'-[(1"S)-1-(Methyl)-2"-(hydroxyamino)-2"-(oxo)ethyl]-6'-(oxo)-6'-(propylamino)hexanoyl]amino-3,3-dimethylbutanoic acid N-2-(4'-sulfamoyl)phenylethylamide;

(2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

N-[(2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

(2S)-N-2'-[(2'R)-2'-[2"-(Hydroxyamino)-2"-(oxo)ethyl-6'-[(4-methoxy)phenoxy]hexanoyl]amino-3,3- dimethylbutanoic acid N-2-(4'-sulfamoyl) phenylethylamide;

(2S)-N-2'-[(2'R)-2'-[2"-(Hydroxyamino)-2"-(oxo)ethyl]-6'-[(4-methyl)phenoxy]hexanoyl]amino-3,3-dimethylbutanoic acid N-2-(4'-sulfamoyl) phenylethylamide;

(2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl) phenylethylamide;

(2S)-N-2-[(2'R)-2'-[(1"S)-1"-(Methyl)-2"-(hydroxyamino)-2"-(oxo)ethyl]-6-(phenylmethoxy)hexanoyl]amino-3,3-dimethylbutanoic acid N-methylamide;

(2S)-N-2-[(2'R)-2'-[(1"S)-1"-(2-Methylpropyl)-2"-(hydroxyamino)-2"-(oxo)ethyl]-6-(phenylmethoxy) hexanoyl]amino-3,3-dimethylbutanoic acid N-methylamide;

N-[(2R)-2-[2'-(Hydroxyamino)-2'-(oxo)ethyl-6-(phenoxy) hexanoyl]-L-phenylalanine N-methylamide;

N-[(2R)-2-[2'-(Hydroxyamino)-2'-(oxo)ethyl]-7-(phenoxy) heptanoyl]-L-phenylalanine N-methylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

(2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)phenylethylamide;

N-[(2R)-2-[2'-(Hydroxyamino)-2'-(oxo)ethyl]-5-(phenylmethoxy)pentanoyl]-L-phenylalanine N-methylamide;

N-[(2R)-2-[2'-(Hydroxyamino)-2'-(oxo)ethyl]-7-(phenylmethoxy)heptanoyl]-L-phenylalanine N-methylamide;

N-[(2R)-2-[2'-(Hydroxyamino)-2'-(oxo)ethyl]-6-(phenyloxy)hexanoyl]-L-phenylalanine N-methylamide;

N-[(2R)-2-[2'-(Hydroxyamino)-2'-(oxo)ethyl]-7-[(phenyloxy)heptanoyl]-L-phenylalanine N-methylamide;

(2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

(2S)-N-2'-[(2'R)-2'-[2"-(Hydroxyamino)-2"-(oxo)ethyl]-6'-[(3-methylphenoxy)hexanoyl)amino-3,3-dimethylbutanoic acid N-methylamide;

(2S)-N-2'-[(2'R)-2'-(Carboxymethyl)-6'-(3-methylphenoxy) hexanoyl]amino-3,3-dimethylbutanoic acid N-methylamide;

(3R,10S)-5-Methyl-3-(9-oxo-1,8-diazatricyclo [10.6.1.0] nonadeca-12(19),13(18),14,16-tetraen-10-ylcarbamoyl) hexanoic acid;

(3R,10S)-N-Hydroxy-5-methyl-3-(9-oxo-1,8-diazatricyclo [10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo [11.6.1.0]eicosa -13(20),14(19),15,17-tetraen-11-ylcarbamoyl)hexanamide;

(3R,9S)-5-Methyl-3-(8-oxo-1,7-diazatricyclo[9.6.1.0] octadeca-11(18),12(17),13,15-tetraen-9-ylcarbamoyl) hexanoic acid;

(3R,9S)-N-Hydroxy-5-methyl-3-(8-oxo-1,7-diazatricyclo [9.6.1.0]octadeca-11 (18),12(17),13,15-tetraen-9-ylcarbamoyl)hexanamide;

(10S)-[4-Methyl-2-(9-oxo-1,8-diazatricyclo[10.6.1.0] nonadeca-12(19),13(18),14,16-tetraen-10-ylcarbamoyl) pentyl]-(quinolin-2-ylthiomethyl)phosphinic acid;

(3R,10S)-N-Hydroxy-5-methyl-2-methoxycarbonyl-3-(9-oxo-1,8-diazatricyclo[10.6.1.0]nonadeca-12(19),13(18), 14,16-tetraen-10-ylcarbamoyl)hexanamide;

N-(4-Methyl-2-carboxymethylpentanoyl)-L-leucine-N'-(4-methoxycarbonylphenyl)carboxamide;

N-(4-Methyl-2-(N"-hydroxycarbamoyl)methylpentanoyl)-L-leucine-N'-(4-methoxycarbonylphenyl)carboxamide;

N-(4-Methyl-2-(N"-hydroxycarbamoyl)methylpentanoyl)-L-leucine-N'-(4-carboxyphenyl)carboxamide;

N-(4-Methyl-2-(N"-hydroxycarbamoyl)methylpentanoyl)-L-tryptophan-N'-(4-carboxyphenyl)carboxamide;

N-(4-Methyl-2-(N"-hydroxycarbamoyl)methylpentanoyl)-L-cyclohexylglycine-N'-(4-methoxycarbonylphenyl) carboxamide;

N-(4-Methyl-2-(N"-hydroxycarbamoyl)methylpentanoyl)-L-t-leucine-N'-(4-methoxycarbonylphenyl)carboxamide;

(3R,10S)-6-Biphenyl-4-yl)-3-(9-oxo-1,8-diazatricyclo [10.6.1.0]nonadeca-12(19),13(18),14,16-tetraen-10-ylcarbamoyl)hexanoic acid;

(3R,10S)-3-(9-Oxo-1,8-diazatricyclo[10.6.1.0]nonadeca-12 (19),13(18),14,16-tetraen-10-ylcarbamoyl)-5-(thiophen-2-yl)pentanoic acid;

(3R,10S)-3-Cyclopentyl-3-(9-oxo-1,8-diazatricyclo [10.6.1.0]nonadeca-12(19),13(18),14,16-tetraen-10-ylcarbamoyl)propionic acid;

(3R,10S)-4-Cyclopentyl-3-(9-oxo-1,8-diazatricyclo [10.6.1.0]nonadeca-12(19),13(18),14,16-tetraen-10-ylcarbamoyl)butanoic acid;

(3R,10S)4-Cyclopropyl-3-(9-oxo-1,8-diazatricyclo [10.6.1.0]nonadeca-2(19),13(18),14,16-tetraen-10-ylcarbamoyl)butanoic acid;

(3R,10S)-5-Methyl-3-(9-oxo-1,8-diazatricyclo [10.6.1.0] nonadeca-12(19),13(18),14,16-tetraen-10-ylcarbamoyl) hexanoic acid;

(3R,10S)-N-Hydroxy-5-methyl-3-(9-oxo-1,8-diazatricyclo [10.6.1.0]nonadeca-12(19),13(18),14,16-tetraen-10-ylcarbamoyl)hexanamide;

(3R,11S)-N-Hydroxy-5-methyl-3-(10-oxo-1,9-diazatricyclo (1.6.1.0]eicosa-13(20),14(19),15,17-tetraen-11-ylcarbamoyl)hexanamide;

(3R,9S)-N-5-Methyl-3-(8-oxo-1,7-diazatricyclo[9.6.1.0] octadeca-11(18),12(17),13,15-tetraen-9-ylcarbamoyl) hexanoic acid;

(3R,9S)-N-Hydroxy-5-methyl-3-(8-oxo-1,7-diazatricyclo [9.6.1.0]octadeca-11(18),12(17),13,15-tetraen-9-ylcarbamoyl)hexanamide;

(10S)-2-Mercaptomethyl-4-methyl-N-(9-oxo-1,8-diazatricyclo[10.6.1.0]nonadeca-12(19),13(18),14,16-tetraen-10-ylcarbamoyl)pentanamide;

(10S)-2-Acetylthiomethyl-4-methyl-N-(9-oxo-1,8-diazatricyclo[10.6.1.0]nonadeca-12(19),13(18),14,16-tetraen-10-ylcarbamoyl)pentanamide;

(3R,10S)-2-(Methanesulfonamidomethyl)-5-methyl-3-(9-oxo-1,8-diazatricyclo[10.6.1.0]nonadeca-12(19),13(18), 14,16-tetraen-10-ylcarbamoyl)hexanoic acid;

(3R,10S)-2-(3-Ethylureidomethyl)-5-methyl-3-(9-oxo-1,8-diazatricyclo[10.6.1.0]nonadeca-12(19),13(18),14,16-tetraen-10-ylcarbamoyl)hexanoic acid;

(3R,9S)-N-Hydroxy-2-hydroxy-5-methyl-3-(8-oxo-1,7-diazatricyclo[9.6.1.0]octadeca-11(18),12(17),14,16-tetraen-9-ylcarbamoyl)hexanamide or its (2S,3R,9S) stereoisomer;

(3R,10S)-N-Hydroxy-5-methyl-2-methoxycarbonyl-3-(9-oxo-1,8-diazatricyclo[10.6.1.0]nonadeca-12(19),13(18), 14,16-tetraen-10-ylcarbamoyl)-hexanamide;

(3R,9S)-5-Methyl-3-(8-oxo-4-oxo-1,7-diazatricyclo[9.61.0]
  octadeca-11(18),12,14,16-tetraen-9-ylcarbamoyl)
  hexanoic acid;
(3R,9S)-3-Cyclobutylmethyl-N-(8-oxo-4-oxo-1,7-
  diazatricyclo[9.6.1.0]octadeca-11(18),12,14,16-tetraen-
  9-ylcarbamoyl)succinamic acid;
(3R,9S)-3-(8-Oxo-4-oxo-1,7-diazatricyclo[9.6.1.0]
  octadeca-11(18),12,14,16-tetraen-9-ylcarbamoyl)-5-
  phenoxy-pentanoic acid;
(3R,9S)-5-(4-Chlorophenoxy)-3-(8-oxo-4-oxo-1,7-
  diazatricyclo[9.6.1.0]octadeca-11(18),12,14,16-tetraen-
  9-ylcarbamoyl)pentanoic acid;
(3R,9S)-5-(4-Chlorophenoxy)-3-(8-oxo-4-oxo-1,7-
  diazatricyclo[9.6.1.0]octadeca-11(18),12,14,16-tetraen-
  9-ylcarbamoyl)pentanoic acid ethyl ester;
(3R,9S)-3-(8-Oxo-1,7-diazatricyclo[9.6.1.0]octadeca-11
  (18),12,14,16-tetraen-9-ylcarbamoyl)pentanoic acid ethyl
  ester;
(3R,9S)-6-(4-Hydroxy-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-3-(8-Oxo-4-oxa-1,7-diazatricyclo[9.6.1.0]
  octadeca-11(18),12,14,16-tetraen-9-ylcarbamoyl)-6-
  pyridin-4-yl-hexanoic acid;
(3R,9S)-6-[4-(3-Hydroxy-propoxy)-phenyl]-3-(8-oxo-4-
  oxo-1,7-diazatricyclo[9.6.1.0]octadeca-11(18),12,14,16-
  tetraen-9-ylcarbamoyl)hexanoic acid;
(3R,9S)-3-(8-Oxo-4-oxo-1,7-diazatricyclo[9.6.1.0]
  octadeca-11 (18),12,14,16-tetraen-9-ylcarbamoyl)-5-(4-
  phenoxy-phenyl)pentanoic acid;
(3R,9S)-6-[4-(2-Hydroxy-ethoxy)-phenyl]-3-(8-oxo-4-oxo-
  1,7-diazatricyclo[9.6.1.0]octadeca-11(18),12,14,16-
  tetraen-9-ylcarbamoyl)hexanoic acid;
(3R,9S)-3-(8-Oxo-4-oxo-1,7-diazatricyclo[9.6.1.0]
  octadeca-11 (18),12,14,16-tetraen-9-ylcarbamoyl)-6-[4-
  (2-pyrrolidin-1-yl-ethoxyphenyl]hexanoic acid;
(3R,9S)-6-(4-Methoxy-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-6-[4-(2-Methoxy-ethoxy)-phenyl]-3-(8-oxo-4-oxo-
  1,7-diazatricyclo[9.6.1.0]octadeca-11(18),12,14,16-
  tetraen-9-ylcarbamoyl)hexanoic acid;
(3R,9S)-3-(8-Oxo4-oxo-1,7-diazatricyclo[9.6.1.0]octadeca-
  11 (1 8),12,14,16-tetraen-9-ylcarbamoyl)-5-phenyl-
  pentanoic acid;
(3R,9S)-3-(8-Oxo-4-oxo-1,7-diazatricyclo[9.61.0]octadeca-
  11 (18),12,14,16-tetraen-9-ylcarbamoyl)-6-phenyl-
  hexanoic acid;
(3R,9S)-6-(3-Hydroxy-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-3-(8-Oxo-4-oxo-1,7-diazatricyclo[9.6.1.0]
  octadeca-11 (1 8),12,14,16-tetraen-9-ylcarbamoyl)-6-[4-
  (3-piperidin-1-yl-propoxy)phenyl]hexanoic acid;
(3R,9S)-6-[4-(3-Dimethylamino-propoxy)-phenyl]-3-(8-
  oxo-4-oxo-1,7-diazatricyclo[9.6.1.0]octadeca-11(18),12,
  14,16-tetraen-9-ylcarbamoyl)hexanoic acid;
(3R,9S)-6-[4-(2-Dimethylamino-ethoxy)-phenyl]-3-(8-oxo-
  4-oxo-1,7-diazatricyclo [9.6.1.0]octadeca-11(18),12,14,
  16-tetraen-9-ylcarbamoyl)hexanoic acid;
(3R,9S)-6-(4-Cyano-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-6-Naphthalen-2-yl-3-(8-oxo-4-oxo-1,7-
  diazatricyclo[9.6.1.0]octadeca-11(18),12,14,16-tetraen-
  9-ylcarbamoyl)hexanoic acid;
(3R,9S)-3-(8-Oxo-4-oxo-1,7-diazatricyclo[9.6.1.0]
  octadeca-11(18),12,14,1 6-tetraen-9-ylcarbamoyl)-6-(4-
  pyrrol-1-yl)hexanoic acid;
(3R,9S)-6-(4-Hydroxy-3-methyl-phenyl)-3-(8-oxo-4-oxo-1,
  7-diazatricyclo[9.6.1.0]octadeca-11(18),12,14,16-
  tetraen-9-ylcarbamoyl)hexanoic acid;
(3R,9S)-6-(4-Benzyloxy-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-6-[4-(4-Aminobutoxy-phenyl)]-3-(8-oxo-4-oxo-1,
  7-diazatricyclo[9.6.1.0]octadeca-11(18),12,14,16-
  tetraen-9-ylcarbamoyl)hexanoic acid;
(3R,9S)-5-(4-Methoxy-phenyl)-3-(8-oxo-4-oxo-1,7-
  diazatricyclo[9.6.1.0]octadeca-11(18),12,14,16-tetraen-
  9-ylcarbamoyl)pentanoic acid;
(3R,9S)-6-(4-Amino-phenyl)-3-(8-oxo-4-oxo-1,7-
  diazatricyclo[9.6.1.0]octadeca-11(18),12,14,16-tetraen-
  9-ylcarbamoyl)hexanoic acid;
(3R,9S)-3-(8-Oxo-4-oxo-1,7-diazatricyclo[9.6.1.0]
  octadeca-11 (18),12,14,16-tetraen-9-ylcarbamoyl)-6-[4-
  (pyridin-4-ylmethoxy)phenyl]hexanoic acid;
(3R,9S)-6-(4-Acetylamino-phenyl)-3-(8-oxo-4-oxo-1,7-
  diazatricyclo[9.6.1.0]octadeca-11(18)12,14,16-tetraen-9-
  ylcarbamoyl)hexanoic acid;
N$^\alpha$-[[3-(N-Hydroxycarbamoyl)-4-methylthio-2-
  propoxymethyl]butylyl]-N,O-dimethyltyrosine amide;
N$^\alpha$-[[3-(N-Hydroxycarbamoyl)-4-isopropylthio-2-
  propoxymethyl]butylyl]-N,O-dimethyltyrosine amide;
N$^\alpha$-[[3-(N-Hydroxycarbamoyl)-2-propylthio]butylyl]-N,O-
  dimethyltyrosine amide;
N-[N-(1-Phosphono-3-phenylpropyl)-(S)-leucyl]-(S)-
  phenylalanine-N-methylamide;
N-[N-(1-Phosphono-3-(4-bromo-1,8-naphthalene-
  dicarboximido)propyl)-(S)-leucyl]-(S)-phenylalanine
  methylamnide;
N-[N-(1-Phosphono-3-(benzyloxycarbonylamino)propyl)-
  (S)-leucyl]-(S)-phenylalanine methylamide;
N-[N-(1-Phosphono-3-(2-hydroxyphenyl)propyl)-(S)-
  leucyl]-(S)-phenylalanine methylamide;
N-[N-(1-Phosphono-3-(methylmercapto)propyl)-(S)-
  leucyl]-(S)-phenylalanine-N-methylamide;
N-[N-(1-Phosphono-3-(methylsulphinyl)propyl)-(S)-
  leucyl]-(S)-phenylalanine-N-methylamide;
N-[N-(1-Phosphono-3-(methylsulphonyl)propyl)-(S)-
  leucyl]-(S)-phenylalanine-N-methylamide;
N-[N-(1-Phosphono-3-(1,8-naphthalenedicarboximido)
  propyl)-(S)-leucyl]-(S)-tryptophan-N-methylamide;
N-[N-(1-Phosphono-3-(1,8-naphthalenedicarboximido)
  propyl)-(S)-leucyl]-(S)-lysine-N-methylamide;
N-[N-(1-Phosphono-3-(1,8-naphthalenedicarboximido)
  propyl)-(S)-leucyl]-(−)-aminoazacyclotridecan-2-one;
N-[N-(1-Phosphono-3-(1,8-naphthalenedicarboximido)
  propyl)-(S)-leucyl]-(S)-lysine-N-(aminoethyl)amide;
N-[N-(1-Phosphono-3-(1,8-naphthalenedicarboximido)
  propyl)-(S)-leucyl]-(S)-lysine-N-(ethylpyrrolidine)
  amide;
N-[N-(1-Phosphono-3-(1,8-naphthalenedicarboximido)
  propyl)-(S)-leucyl]-(S)-lysine-N-(ethyl-N-
  methylpiperazine)amide;
N-[N-(1-Phosphono-3-[8-(7,9-dioxo-8-azaspiro[4,5]decyl)]
  propyl)-(S)-leucyl]-(S)-phenylalanine-N-methylamide; and
N-[N-(1-Phosphono-3-[8-(7,9-dioxo-8-azaspiro[4,5]decyl)]
  propyl)-(S)-leucyl]-(S)-lysine-N-methylamide.

As noted above, numerous inhibitors of matrix metalloproteinases are known. A large number of inhibitors are characterized as hydroxamic acid-based and/or carboxylic acid-based compounds. Typical of such compounds are those described in the following references, all of which are incorporated herein by reference since all of the disclosed compounds can be used in the method of this invention.

| US 4599361 | (Searle) |
|---|---|
| EP-A-2321081 | (ICI) |
| EP-A-0236872 | (Roche) |
| EP-A-0274453 | (Bellon) |
| WO 90/05716 | (British Biotechnology) |
| WO 90/05719 | (British Biotechnology) |
| WO 91/02716 | (British Biotechnology) |
| WO 92/09563 | (Glycomed) |
| US 5183900 | (Glycomed) |
| US 5270326 | (Glycomed) |
| WO 92/17460 | (Smith-Kline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Biotechnology) |
| WO 92/22523 | (Research Corporation Technologies) |
| WO 93/09090 | (Yamanouchi) |
| WO 93/09097 | (Sankyo) |
| WO 93/20047 | (British Biotechnology) |
| WO 93/24449 | (Celltech) |
| WO 93/24475 | (Celltech) |
| EP-A-0574758 | (Roche) |
| WO 94/02447 | (British Biotechnology) |
| WO 94/02446 | (British Biotechnology) |

An especially preferred group of compounds to be employed in the present method are those described in WO 95/35275 and WO 95/35276, both of which are incorporated herein by reference. Typical compounds from within these groups to be employed include:
N-Hydroxy-2-[[(2-(4-methoxy-phenoxy)-ethyl-(toluene-4-sulfonyl)-amino]-acetamide;
N-Hydroxy-2-[(4-phenoxy-ethyl)-toluene-4-sulfonyl) amino]-acetamide;
N-Hydroxy-2-[(4-methoxy-benzenesulfonyl)-nonyl-amino]-acetamide;
2-[-Decyl-(toluene-4-sulfonyl)-amino]-N-hydroxy-acetamide;
2-Benzyl-(octane-1-sulfonyl)-amino]-N-hydroxy-acetamide;
N-Hydroxy-2-[(2-methoxy-benzyl)-(octane-1-sulfonyl)-amino]-acetamide;
2-[(2-Ethoxy-benzyl)-(octane-1-sulfonyl)-amino]-N-hydroxy-acetamide;
N-Hydroxy-2-[(naphthalen-2-yl-methyl)-(octane-1-sulfonyl)-amino]-acetamide;
2-[(4-Chloro-benzyl)-(octane-1-sulfonyl)-amino]-N-hydroxy-acetamide, and salts, solvates, or hydrates thereof.

Another class of matrix metalloproteinase inhibitors are aryl sulfonamides of the formula

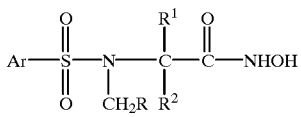

where Ar is carbocyclic or heterocyclic aryl, and R, $R^1$, and $R^2$ include hydrogen, alkyl, aryl, heteroaryl, amino, substituted and disubstituted amino. These compounds are disclosed in European Patent Number 0606046, incorporated herein by reference. Specific compounds to be employed in the present method include:
N-Hydroxy-2-[[4-methoxybenzenesulfonyl](isobutyl) amino]acetamide;
N-Hydroxy-2-[[4-methoxybenzenesulfonyl](cyclo-hexylmethyl)amino]acetamide;
N-Hydroxy-2-[[4-methoxybenzenesulfonyl](cyclo-hexyl) amino]acetamide;
N-Hydroxy-2-[[4-methoxybenzenesulfonyl](phenethyl) amino]acetamide;
N-Hydroxy-2-[[4-methoxybenzenesulfonyl](3-methylbutyl) amino]acetamide;
N-Hydroxy-2-[[4-methoxybenzenesulfonyl](sec-butyl) amino]acetamide;
N-Hydroxy-2-[[4-methoxybenzenesulfonyl](tert-butyl) amino]acetamide
N-Hydroxy-2-[[4-methoxybenzenesulfonyl](4-fluorobenzyl)amino]acetamide
N-Hydroxy-2-[[4-methoxybenzenesulfonyl](4-chlorobenzyl)amino]acetamide
N-Hydroxy-2-[[4-methoxybenzenesulfonyl](isopropyl)-amino]acetamide
N-Hydroxy-2-[[4-methoxybenzenesulfonyl](4-methylbenzyl)amino]acetamide
4-N-Hydroxy-carbamoyl)-4-[[4-methoxybenzene-sulfonyl (benzyl)-amino]-1-[dimethylaminoacetyl]-piperidine hydrochloride 4-N-Hydroxy-carbamoyl]-4-[[4-methoxybenzene-sulfonyl(benzyl)-amino]-1-[3-picolyl]-piperidine dihydrochloride 4-N-Hydroxy-carbamoyl]-4-[[4-methoxybenzene-sulfonyl(benzyl)-amino]-1-[carbomethoxymethyl]-piperidine hydrochloride 4-N-Hydroxy-carbamoyl]-4-[[4-methoxybenzene-sulfonyl (benzyl)-amino]-1-piperidine trifluoroacetate;
4-N-Hydroxy-carbamoyl]-4-[[4-methoxybenzene-sulfonyl (benzyl)-amino]-1-[t-butoxycarbonyl]-piperidine;
4-N-Hydroxycarbamoyl]-4-[[4-methoxybenzene-sulfonyl (benzyl)-amino]-1-[methylsulfonyl]-piperidine;
N-Hydroxycarbamoyl]-4-[[4-methoxybenzene-sulfonyl (benzyl)-amino]-1-[4-picolyl]-piperidine hydrochloride;
N-Hydroxycarbamoyl]4-[[4-methoxybenzene-sulfonyl (benzyl)amino]-1-[morpholinocarbonyl]-piperidine hydrochloride; and
N-(t-Butyloxy)-2-[[4-methoxybenzenesulfonyl(benzyl) amino]-2-[2-(4-morpholino)ethyl]acetamide.
The following compounds are prepared similarly to Example 7:
N-Hydroxy-2-[[4-methoxybenzenesulfonyl](isobutyl)-amino-2-(2-(4-morpholino)ethyl]acetamide;
N-Hydroxy-2-[[4-methoxybenzenesulfonyl](2-picoly)-amino-2-(2-(4-morpholino)ethyl]acetamide dihydrochloride;
N-Hydroxy-2-[[4-methoxybenzenesulfonyl](3-picolyl) amino]-2-[2-(4-morpholino)ethyl]acetamide dihydrochloride;
N-Hydroxy-2-[[4-methoxybenzenesulfonyl](2-methyl-thiazol-4-ylmethyl)amino]-2-[2-(4-morpholino)ethyl] acetamide dihydrochloride;
N-Hydroxy-2-[[4-methoxybenzenesulfonyl]benzyl)amino]-2-[2-(4-thiomorpholino]ethyl]acetamide;
N-Hydroxy-2-[[4-methoxybenzenesulfonyl](benzyl) amino]-2-[2-(4-methylthiazol-4-ylmethyl]acetamide;
N-Hydroxy-2-[[4-methoxybenzenesulfonyl(benzyl)amino]-2-[(6-chloropiperonyl]acetamide;
N-Hydroxy-2-[[4-methoxybenzenesulfonyl(benzyl)amino]-2-[(1-pyrazolyl)methyl]acetamide;
N-Hydroxy-2-[[4-methoxybenzenesulfonyl(3-picolyl) amino]-2-[3-picolyl]acetamide;
N-Hydroxy-2-[[4-methoxybenzenesulfonyl(benzyl)-amino]-2-[(1-methyl-4-imidazolyl)methyl]acetamide hydrochloride;
N-Hydroxy-2-[[4-methoxybenzenesulfonyl(isobutyl) amino]-2-[(1-methyl-4-imidazolyl)methyl]acetamide hydrochloride;

N-Hydroxy-2-[[4-methoxybenzenesulfonyl](3-picolyl) amino]-2-[(1-methyl-4-imidazolyl)methyl]acetamide hydrochloride;

N-Hydroxy-2-[[4-methoxybenzenesulfonyl(2-picolyl) amino]-2-[(1-methyl-4-imidazolyl)methyl]-acetamide hydrochloride; and N-Hydroxy-2-[[4-methoxybenzenesulfonyl](2-methylthiazol-4-ylmethyl)amino-2-[(1-methyl-4-imidazolyl)methyl]acetamide hydrochloride.

Another group of small peptide matrix metalloproteinase inhibitors are described in U.S. Pat. Nos. 5,270,326, 5,530, 161, 5,525,629, and 5 5,304,604 (incorporated herein by reference). The compounds are hydroxamic acids defined by the formula.

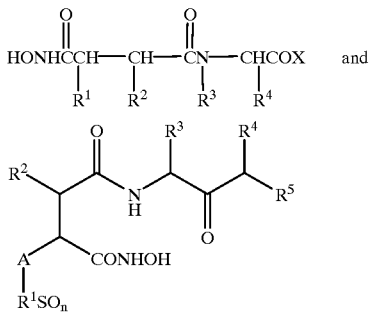

where $R^1$, $R^2$, $R^3$, and $R^4$ can be hydrogen or alkyl and X is $OR^5$ or $NHR^5$ where $R^5$ includes hydrogen, alkyl and aryl, A includes alkyl, and n is 0 to 2. Typical compounds to be employed in the instant method include the following:

N-[2-Isobutyl-3-(N'-hydroxycarbonylamido)-propanoyl]-D-tryptophan methyl amide;

N-[2-Isobutyl-3-(N'-hydroxycarbonylamido)-propanoyl]-N-methyl-L-tryptophan methylamide;

N-[2-Isobutyl-3)(-hydroxycarbonylamido)-propanoyl]-L-3-(2-naphthyl)-alanine methylamide;

N-[2-Isobutyl-3-(N'-hydroxycarbonylamido)-propanoyl]-L-tryptophan 2-hydroxyethylamide;

N-[2-Isobutyl-3-(N'-hydroxycarbonylamido)-propanoyl]-L-tryptophan amylamide;

N-[2-Isobutyl-3-(N'-hydroxycarbonylamido)-propanoyl]-L-tryptophan piperidinamide;

N-[2-isobutyl-3-(N'-hydroxycarbonylamido)-propanoyl-L-tryptophan dodecylamide;

N-[2-Isobutyl-3-(N'-hydroxycarbonylamido)-propanoyl]-L-tryptophan(S)-methylbenzylamide;

N-[L-2-Isobutyl-3-(N'-hydroxycarbonylamido)-propanoyl]-L-tryptophan(6-phenylmethoxycarbonyl-amino-hexyl-1) amide;

2S-Hydroxy-3R-[S -(3-methoxy-2,2-dimethyl-propylcarbamoyl)-2,2-dimethyl-propylcarbamoyl)-5-methyl-hexanohydroxamic acid;

2S-Hydroxy-3)R-[1S-(methylcarbamoyl)-2,2-dimethyl-propylcarbamoyl]-6-(4-chloro)phenyl-hexanohydroxamic acid;

2S-Hydroxy-3R-[1S-(methylcarbamoyl)-2,2-dimethyl-propylcarbamoyl]octanohydroxamic acid;

2S-Hydroxy-3R-[1S-(pyridin-2-ylmethylcarbamoyl)-2,2-dimethyl-propylcarbamoyl]-5-methyl-hexanohydroxamic acid;

2S-Hydroxy-3R-[1S-(pyridin-3-ylmethylcarbamoyl)-2,2-dimethylpropylcarbamoyl]-5-methyl-hexanohydroxamic acid;

2S-Hydroxy-3R-[1S-(pyridin-4-ylmethylcarbamoyl)-2,2-dimethyl-propylcarbamoyl]-5-methyl-hexanohydroxamic acid;

2S-Hydroxy-3R-[1S-(methylcarbamoyl)-2,2-dimethyl-propylcarbamoyl]-4-methoxy-butanohydroxamic acid;

2S-Hydroxy-3R-[1S-(methylcarbamoyl)-2,2-dimethyl-propyl carbamoyl]4-benzyloxy-butanohydroxamic acid;

2S-Hydroxy-3R-[1S-(methylcarbamoyl)-2,2-dimethyl-propylcarbamoyl]4-benzylthio-butanohydroxamic acid;

2S-Hydroxy-3R-[1S-(methylcarbamoyl)-2,2-dimethyl-buten-3-ylcarbamoyl]-5-methyl-hexanohydroxamic acid;

2S-Hydroxy-3R-[1S-(tert-butylcarbamoyl)-2,2-dimethyl-propylcarbamoyl]-5-methyl-hexanohydroxamic acid;

2S-Hydroxy-3R-[1S-(N,N-dimethyl-carbamoyl)-2,2-dimethyl-propylcarbamoyl]-5-methyl-hexanohydroxamic acid;

2S-Hydroxy-3R-[1S-(3-hydroxy-2,2-dimethyl-propylcarbamoyl)-2,2-dimethyl-propylcarbanoyl]-5-methyl-hexanohydroxamic acid;

2S-Hydroxy-3R-[1S-(methylcarbamoyl)-2,2-dimethyl-propylcarbamoyl]-6-phenyl-hexanohydroxamic acid;

2S-Hydroxy-3R-[1S-(methylcarbamoyl)-2,2-dimethyl-butylcarbamoyl]-5-methyl-hexanohydroxamic acid;

[4-(N-Hydroxyamino)-2R-isobutylsuccinyl)-L-phenylalanine-N-(2-hydroxyethyl)-amide;

[4-N-Hydroxyamino)-2R-isobutylsuccinyl]-L-phenylalanine-proline;

[4-(N-Hydroxyamino)-2R-isobutylsuccinyl]-L-phenylalanine-N-(2-hydroxyethyl)-N-methylamide;

[4-(N-Hydroxyamino)-2R-isobutylsuccinyl]-L-phenylalaninyl-D-prolinol;

(4-(N-Hydroxyamino)-2R-isobutylsuccinyl]-L-phenylalaninyl-L-prolinol;

[4-(N-Hydroxyamino)-2R-isobutylsuccinyl]-L-phenylalanine-N-(5-N-methyl-pentylcarboxamide) amide;

[4-(N-Hydroxyamino)-2R-isobutylsuccinyl]-L-phenylalanine-N-(2-ethylthioethyl)amide;

[4-(N-Hydroxyamino)-2R-isobutylsuccinyl]-L-phenylalanine-N-(2-methoxyethyl)amide;

[4-(N-Hydroxyamino)-2R-isobutylsuccinyl]-L-phenylalanine-N-(2-N-acetylethyl)amide;

[4-(N-Hydroxyamino)-2R-isobutylsuccinyl]-L-phenylalanine-N-(3-(2-pyrrolidone)propyl)amide;

[4-(N-Hydroxyamino)-2R-isobutylsuccinyl]-L-phenylalanine-N-(3-(2-pyrrolidone)propyl)amide sodium salt;

[4-(N-Hydroxyamino)-2R-isobutylsuccinyl]-L-phenylalanine-N-(2-acetoxyethyl)amide;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-methyl-N-(2-hydroxyethyl)amide;

[4-(N-Hydroxyamino)-2R-isobutyl-3S-methylsuccinyl]-L-phenylalanine-N-(2-hydroxyethyl)amide;

[4-(N-Hydroxyamino)-2R-isobutyl-3S-methyl succinyl]-L-phenylalaninyl-D-prolinol;

[4-(N-Hydroxyamino)-2R-isobutyl-3S-methylsuccinyl]-L-phenylalanine-N-(3-(2-pyrrolidone)propyl)amide sodium salt;

[4-(N-Hydroxyamino)-2R-isobutyl-3S-methylsuccinyl]-L-phenylalanine-N-(3-(2-pyrrolidone)propyl)amide;

[4-(N-Hydroxyamino)-2R-isobutyl-3S-methylsuccinyl]-L-phenylalanine-N-(3-(2-pyrrolidone)propyl)amide or a salt thereof;

$N^2$-[4-(N-Hydroxyamino)-3S-(4-hydroxyphenylthiomethyl)-2R-isobutylsuccinyl]-$N^6$-tert-butyloxycarbonyl-L-lysine-$N^1$-methylamide;

$N^2$-[4-(N-Hydroxyamino)-3S-(4-hydroxyphenylthiomethyl)-2R-isobutylsuccinyl]-$N^6$-tertbutyloxycarbonyl-$N^6$-(4-hydroxyphenylthiomethyl)-L-lysine-$N^1$-methylamide;

$N^2$-[4-(N-Hydroxyamino)-3S-(2-thienylthiomethyl)-2R-isobutylsuccinyl]-$N^6$-tert-butyloxycarbonyl-L-lysine-$N^1$-methylamide;

$N^2$-[4-(N-Hydroxyamino)-3S-(4-hydroxyphenylthiomethyl)-2R-isobutylsuccinyl]-O-tert-butyl-L-threonine-$N^1$-methylamide;

$N^2$-[4-(N-Hydroxyamino)-3S-(4-hydroxyphenylthiomethyl)-2R-isobutylsuccinyl]-L-glutamine-$N^1$,$N^5$-dimethylamide;

$N^2$-[4-(N-Hydroxyamino)-3S-(4-hydroxyphenylsulphonylmethyl)-2R-isobutylsuccinyl]-$N^6$-acetyl-L-lysine-$N^1$-methylamide;

3R-(3-Methoxycarbonyl-1S-methylcarbamoyl-propylcarbamoyl)-5-methyl-2S-2-propenyl-hexanohydroxamic acid;

3R-(1S-Methylcarbamoyl-2-thien-2-yl-ethylcarbamoyl)-5-methyl-2S-2-propenyl-hexanohydroxamic acid;

3R-(3-Methyl-1S-methylcarbamoyl-butylcarbamoyl)-5-methyl-2S-2-propenyl-hexanohydroxamic acid;

2S-[1S-Methylcarbamoyl-2-oxadiazol-5-yl-ethylcarbamoyl)-5-methyl-2S-2-propenyl-hexanohydroxamic acid;

[4-(N-Hydroxyamino)-2R-isobutylsuccinyl]-L-(4-oxymethylcarboxylic acid)phenylalanine-N-methylamide;

[4-(N-Hydroxyamino)-2R-isobutylsuccinyl]-L-(4-oxymethylcarboxy-N-methylamide)phenylalanine-N-methylamide;

[4-(N-Hydroxyamino)-2R-isobutylsuccinyl]-L-(4-oxymethylcarboxy-beta-alanine)phenylalanine-N-methylamide;

[4-(N-Hydroxyamino)-2R-isobutylsuccinyl]-L-(4-oxymethylcarboxyglycine)phenylalanine-N-methylamide;

[4-(N-Hydroxyamino)-2R-isobutylsuccinyl]-L-(4-oxymethylcarboxy-N-benzylamide)phenylalanine-N-methylamide;

[4-(N-Hydroxyamino)-2R-isobutylsuccinyl]-L-(4-cyano) phenylalanine-N-methylamide;

[4-(N-Hydroxyamino)-2R-isobutylsuccinyl]-L-(4-acetamido)phenylalanine-N-methylamide;

(4-(N-Hydroxyamino )-2R-isobutyl succinyl]-L-(4-oxymethylcarboxamide)-henylalanine-N-methylamide;

[4-(N-Hydroxyamino)-2R-isobutyl-3S-(2-thienylthiomethylsuccinyl]-L-(4-N-acetylamino)-henylalanine-N-methylamide;

[4-(N-Hydroxyamino)-2R-isobutyl-3S-(2-thienylthiomethylsuccinyl]-L-(4-N-methylsuccinylamide)phenylalanine-N-methylamide;

[4-(N-Hydroxyamino)-2R-isobutyl-3S-(4-aminophenylthiomethyl)succinyl]-L-(4-N-(methylsuccinylamide)phenylalanine-N-methylamide;

[4-(N-Hydroxyamino)-2R-isobutyl-3S-(4-aminophenylthiomethylsuccinyl]-L-(4-N-(4-(4-oxobutanoic acid)aminophenylalanine-N-methylamide;

[4-(N-Hydroxyamino)-2R-isobutyl-3S-(4-hydroxyphenylthiomethyl)succinyl]-L-(4-N-methylsuccinylamido)phenylalanine-N-methylamide;

[4-(N-Hydroxyamino)-2R-isobutyl-3S-(4-hydroxyphenylthiomethyl)-succinyl]-L-(4-N-(4-(4-oxobutanoic acid)aminophenylalanine-N-methylamide;

[4-(N-Hydroxyamino)-2R-isobutyl-3S-(2-thienylthiomethyl)-succinyl]-L-(4-oxymethylcarboxymethyl)phenylalanine-N-methylamide;

[4-(N-Hydroxyamino)-2R-isobutyl-3S-(2-thienylthiomethyl)-succinyl]-L-(4-N-(oxymethylcarboxylic acid)phenylalanine-N-methylamide;

[4-(N-Hydroxyamino)-2R-isobutyl-3S-(2-thienylthiomethyl)-succinyl]-L-4-oxymethylcarboxyglycyl methyl ester)-phenylalanine-N-methylamide;

[4-(N-Hydroxyamino)-2R-isobutyl-3S-(2-thienylthiomethyl)-succinyl]-L-4-oxymethylcarboxyglycine)phenylalanine-N-methylamide;

[4-(N-Hydroxyamino)-2R-isobutyl-3S-methyl-succinyl]-L4-(oxymethylcarboxyglycyl methyl ester)-phenylalanine-N-methylamide;

[4-(N-Hydroxyamino)-2R-isobutyl-3S-methyl)-succinyl]-L-4-(oxymethylcarboxyglycine)-phenylalanine-N-methylamide;

[4-(N-Hydroxyamino)-2R-isobutylsuccinyl]-L-4-oxymethylnitrile)-phenylalanine-N-methylamide;

[4-(N-Hydroxyamino)-2R-isobutylsuccinyl]-L-3-(1-(2-methyloxycarbonyl)-ethyl)-4-methoxyphenylalanine-N-methylamide;

[4-(N-Hydroxyamino)-2R-isobutylsuccinyl]-L-3-(hydroxymethyl)-4-methoxyphenylalanine-N-methylamide;

[4-(N-Hydroxyamino)-2R-isobutylsuccinyl]-L-3-methyl4-methoxyphenylalanine-N-methylamide;

2-[Benzyl-(octane-1-sulfonyl)-amino]-N-hydroxy-acetamide;

N-Hydroxy-2-[(2-methoxy-benzyl)-(octane-1-sulfonyl)-amino]acetamide;

2-[(2-Ethoxy-benzyl)-(octane-1-sulfonyl)-amino]-N-hydroxy-acetamide;

N-Hydroxy-2-[(naphthalen-2-yl-methyl)-(octane-1-sulfonyl)-amino]acetamide;

2-[(4-Chloro-benzyl)-(octane-1-sulfonyl)-amino]-N-hydroxy-acetamide;

$N^2$-[3S-Hydroxy-4-(N-hydroxyamino)-2R-isobutylsuccinyl]-L-leucine-$N^1$-methylamide;

$N^2$-[3S-Hydroxy-4-(N-hydroxyamino)-2R-isobutylsuccinyl)]-5-methyl-L-glutamic acid-$N^1$-methylamide;

$N^2$-[3S-Hydroxy-4-(N-hydroxyamino)-2R-isobutylsuccinyl)]-L-phenylalanine-$N^1$-methylamide;

[4-(N-Hydroxyamino)-2R-isobutyl-3S-(thienylthiomethyl) succinyl]-L-phenylalanine-N-methylamide;

[4-(N-Hydroxyamino)-2R-isobutyl-3S-phenylthiomethyl) succinyl]-L-phenylalanine-N-methylamide;

2S-(4-Methoxyphenylsulfanylmethyl)-3R-(2-phenyl-1S-methylcarbamoyl-ethylcarbamoyl)-5-methyl-hexanohydroxamic acid;

2S-(3-Chlorophenylsulfanylmethyl)-3R-(2-phenyl-1S-methylcarbamoyl-ethylcarbamoyl)-5-methyl-hexanohydroxamic acid;

2S-(Phenylsulfanylmethyl)-3R-(2-phenyl-1S-(pyrid-3-ylmethylcarbamoyl)-ethylcarbamoyl)-5-methyl-hexanohydroxamic acid;

2S-(3-Methylphenylsulfanylmethyl)-3R-(2-phenyl-1S-methylcarbamoyl-ethylcarbamoyl)-5-methyl-hexanohydroxamic acid;

2S-(Thien-2-ylsulfanylmethyl)-3R-(2-(4-carboxymethoxyphenyl)-1S-methylcarbamoyl-ethylcarbamoyl)-5-methyl-hexanohydroxamic acid;

2S-(Thien-2-ylsulfanylmethyl)-3R-(2-phenyl-1S-(pyrid-3-ylmethylcarbamoyl)-ethylcarbamoyl)-5-methyl-hexanohydroxamic acid;

2S-(4-Hydroxyphenylsulfanylmethyl)-3R-(2-phenyl-1S-(pyrid-3-ylmethylcarbamoyl)-ethylcarbamoyl)-5-methyl-hexanohydroxamic acid;
2S-(Thien-2-ylsulfanylmethyl)-3R-(2-naph-2-yl-1S-methylcarbamoyl-ethylcarbamoyl)-5-methyl-hexanohydroxamic acid;
2S-(4-Hydroxyphenylsulfanylmethyl)-3R-(2R-hydroxy-1S-methylcarbamoyl-propylcarbamoyl)-5-methyl-hexanohydroxamic acid;
2S-(4-Hydroxyphenylsulfanylmethyl)-3R-(5-acetamido-1S-methylcarbamoyl-pentylcarbamoyl)-5-methyl-hexanohydroxamic acid;
2S-(4-Hydroxyphenylsulfanylmethyl)-3R-(3-[1,1-dimethylethoxycarbonyl]-1S-methylcarbamoyl-propylcarbamoyl)-5-methyl-hexanohydroxamic acid;
2S-(Thien-2-ylsulfonylmethyl)-3R-(2-phenyl-1S-methylcarbamoyl-ethylcarbamoyl)-5-methyl-hexanohydroxamic acid;
3S-(2-[4-Acetamido-phenyl]-1S-methylcarbamoyl-ethylcarbamoyl)-5-methyl-hexanohydroxamic acid;
2S-(4-Phthalimido-butyl)-3R-(3-methyl-1S-ethoxycarbonylmethylcarbamoyl-butylcarbamoyl)-5-methyl-hexanohydroxamic acid;
3R-(2-[4-Methoxy-phenyl]-1S-methylcarbamoyl-ethylcarbamoyl)-2S,5-dimethyl-hexanohydroxamic acid;
3R-(2-Phenyl-1S-[2-oxo-pyrolid-1-yl]-propylcarbamoyl-ethylcarbamoyl)-5-methyl-hexanohydroxamic acid;
3R-(2-[4-Methoxy-phenyl]-1S-methylcarbamoyl-ethylcarbamoyl)-5-methyl-hexanohydroxamic acid;
3R-(2-Phenyl-1S-[pyrid-3-ylmethyl carbamoyl]-ethylcarbamoyl)-5-methyl-hexanohydroxamic acid;
3R-(2,2-Dimethyl-1S-methylcarbamoyl-propylcarbamoyl)-5-methyl-, hexanohydroxamic acid;
Isobutylmalonoyl-L-alanine-furfurylamide hydroxamate;
2-Isobutyl-3-carbonyl-3'-(4-acetylaniline)propionic acid;
N-Benzyloxycarbonyl-α-phosphonoglycyl-L-alanine furfurylamide;
[4-(N-Hydroxyamino)-2R-isobutyl-3S-(phenylthiomethyl)succinyl]-L-phenylalanine-N-methylamide;
[4-(N-Hydroxyamino)-2R-isobutyl-3S-(4-methoxyphenylthiomethyl)-succinyl]-L-phenylalanine-N-methylamide;
[4-(N-Hydroxyamino)-2R-isobutyl-3S-(4-hydroxyphenylthiomethyl)-succinyl]-L-phenylalanine-N-methylamide;
[4-(N-Hydroxyamino)-2R-isobutyl-3S-(2,4-dimethylphenylthiomethyl)-succinyl]-L-phenylalanine-N-methylamide;
[4-(N-Hydroxyamino)-2R-isobutyl-3S-(3-bromophenylthiomethyl)-succinyl]-L-phenylalanine-N-methylamide;
[4-(N-Hydroxyamino)-2R-isobutyl-3S-(3-chlorophenylthiomethyl)succinyl]-L-phenylalanine-N-methylamide;
[4-(N-Hydroxyamino)-2R-isobutyl-3S-(3-methylphenylthiomethyl)succinyl]-L-phenylalanine-N-methylamide;
[4-(N-Hydroxyamino)-2R-isobutyl-3S-(4-(N-acetyl)-aminophenylthiomethyl)succinyl]-L-phenylalanine-N-methylamide;
[4-(N-Hydroxyamino)-2R-isobutyl-3S-phenylsulphinylmethylsuccinyl]-L-phenylalanine-N-methylamide;
3R-(3-Methoxycarbonyl-1S-methylcarbamoyl-propylcarbamoyl)-5-methyl-2S-phenylsulfanylmethyl-hexanohydroxamic acid;
3R-(3-Methoxycarbonyl-1S-methylcarbamoyl-propylcarbamoyl)-5-methyl-2S-(thien-2-ylsulfanylmethyl)-hexanohydroxamic acid;
2S-(4-Methoxy-phenylsulfanylmethyl)-3R-(3-methoxycarbonyl-1S-methylcarbamoyl-propylcarbamoyl)-5-methyl-hexanohydroxamic acid;
2S-(4-Amino-phenylsulfanylmethyl)-3R-(3-methoxycarbonyl-1S-methylcarbamoyl-propylcarbamoyl)-5-methyl-hexanohydroxamic acid;
2S-(Ethylsulfanylmethyl)-3R-(3-methoxycarbonyl-1S-methylcarbamoyl propylcarbamoyl)-5-methyl-hexanohydroxamic acid;
2S-(Acetylsulfanylmethyl)-3R-(3-methoxycarbonyl-1S-methylcarbamoylpropylcarbamoyl)-5-methyl-hexanohydroxamic acid;
2S-(Benzylsulfanylmethyl)-3R-(3-methoxycarbonyl-1S-methylcarbamoylpropylcarbamoyl)-5-methyl-hexanohydroxamic acid;
2S-(tert-Butylsulfanylmethyl)-3R-(3-methoxycarbonyl-1S-methylcarbamoyl-propylcarbamoyl)-5-methyl-hexanohydroxamic acid;
2S-Thiomethyl-3R-(3-methoxycarbonyl-1S-methylcarbamoylpropylcarbamoyl)-5-methyl-hexanohydroxamic acid;
2S-(4-Hydroxy-phenylsulfanylmethyl)-3R-(2-tert-butoxycarbonyl-1S-methylcarbamoyl-ethylcarbamoyl)-5-methyl-hexanohydroxamic acid;
2S-(4-Hydroxy-phenylsulphinylmethyl)-3R-(3-methoxycarbonyl-1S-methylcarbamoyl-propylcarbamoyl)-5-methyl-hexanohydroxamic acid;
2S-(4-Hydroxy-phenylsulphonylmethyl)-3R-(3-methoxycarbonyl-1S-methylcarbamoyl-propylcarbamoyl)-5-methyl-hexanohydroxamic acid;
[4-(N-Hydroxyamino)-2R-isobutylsuccinyl]-L-phenylalanine-N-[1-(2-aminoethyl)-pyrrolidine]amide;
[4-(N-Hydroxyamino)-2R-isobutylsuccinyl]-L-phenylalanine-N-[1-(3-aminopropyl)-2(RS)-methylpiperidine]amide;
[4-(N-Hydroxyamino)-2R-isobutylsuccinyl]-L-phenylalanine-N-[2-(2-aminoethyl)-1-methylpyrrole]amide;
[4-(N-Hydroxyamino)-2R-isobutylsuccinyl]-L-phenylalanine-N-(3-aminomethylpyridine)amide;
[4-(N-Hydroxyamino)-2R-isobutylsuccinyl]-L-phenylalanine-N-(2-aminomethylpyridine)amide;
[4-(N-Hydroxyamino)-2(RS)-isobutylsuccinyl]-L-phenylalanine-N-(4-aminomethylpyridine)amide;
[4-(N-Hydroxyamino)-2(RS)-isobutylsuccinyl]-L-phenylalanine-N-(1-(3-aminopropyl)-imidazole)amide;
[4-(N-Hydroxyamino)-2(RS)-isobutylsuccinyl]-L-phenylalanine-N-(2-aminomethylbenzimdazole)amide;
[4-(N-Hydroxyamino)-2R-isobutyl-3S-methylsuccinyl]-L-phenylalanine-N-[4-(2-aminoethyl)-morpholino]amide;
[4-(N-Hydroxyamino)-2R-isobutylsuccinyl]-L-phenylalanine-N-[4-(2-aminoethyl)-morpholine]amide;
[4-(N-Hydroxyamino)-2(R,S)-isobutylsuccinyl]-L-phenylalanine-N-[2-(2-aminoethyl)-pyridine]amide;
[4-(N-Hydroxyamino)-2(R,S)-isobutylsuccinyl]-L-phenylalanine-N-[4-(2-aminopropyl)-morpholine]amide;
[4-(N-Hydroxyamino)-2R-isobutylsuccinyl]-L-phenylalanine-N-(3-aminomethylpyridine)amide hydrochloride; and
[4-(N-Hydroxyamino)-2R-isobutylsuccinyl]-L-phenylalanine-N-[4-(2-aminoethyl)-morpholine]amide hydrochloride.

In a preferred embodiment, tricyclic butyric acid derivatives which are inhibitors of matrix metalloprotienases are employed to treat neurological disorder and to promote wound healing according to this invention. A preferred group of tricyclic butyric acid derivatives are defined by the formula:

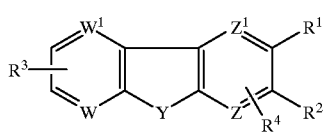

wherein one of $R^1$ or $R^2$ is

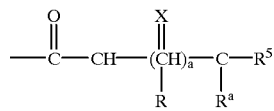

wherein

X is O,
N—$OR^6$ wherein $R^6$ is hydrogen,
—$(CH_2)_n$-aryl wherein n is zero or an integer of 1 to 5, alkyl, or
—$(CH_2)_n$-cycloalkyl wherein n is as defined above, or

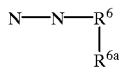

wherein
$R^6$ and $R^{6a}$ are each the same or different and each is as defined above for $R^6$;
R and $R^a$ are each the same or different and each is hydrogen,
—$(CH_2)_n$-aryl wherein n is as defined above,
—$(CH_2)_n$-heteroaryl wherein n is as defined above,
—$(CH_2)_p$-$R^7$—$(CH_2)_q$-aryl wherein $R^7$ is O or S and p or q is each zero or an integer of 1 to 5 and the sum of p+q equals an integer of 5,
—$(CH_2)_p$-$R^7$—$(CH_2)_q$-heteroaryl
wherein p, q, and $R^7$ are as defined above, alkyl,
—$(CH_2)_n$-cycloalkyl wherein n is as defined above, or
—$(CH_2)_r$-$NH_2$ wherein r is an integer of 1 to 9;
a is zero or an integer of 1 to 3;
$R^5$ is OH,
$OR^6$ wherein $R^6$ is as defined above,

wherein
$R^6$ and $R^{6a}$ are each the same or different and are as defined above for $R^6$, or NH—$OR^6$ wherein $R^6$ is as defined above;
$R^3$ and $R^4$ are each the same or different and each is hydrogen,
alkyl,
$NO_2$,
halogen,
$OR^6$ wherein $R^6$ is as defined above,
CN,
$CO_2R^6$ wherein $R^6$ is as defined above,
$SO_3R^6$ wherein $R^6$ is as defined above,

CHO,

wherein R is as defined above,

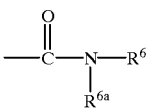

wherein $R^6$ and $R^{6a}$ are each the same or different and are as defined above for $R^6$, or

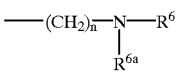

wherein $R^6$ and $R^{6a}$ are
each the same or different and are as defined above for $R^6$;
W, $W^1$, Z, and $Z^1$ are each the same or different and each is $CR^3$ wherein $R^3$ is as defined above, or
N providing only one of W or $W^1$ is
N and/or only one of Z or $Z^1$ is N; and
Y is

wherein R is as defined above,
—O—,
—S—$(O)_m$— wherein m is zero or an integer of 1 or 2,
—$CH_2$—,

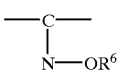

wherein $R^6$ is as defined above,

wherein $R^6$ is as defined above,

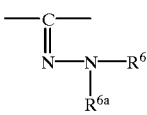

wherein $R^6$ and $R^{6a}$ are the same or different and are as defined above for $R^6$,

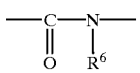

wherein $R^6$ is as defined above,

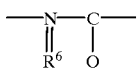

wherein $R^6$ is as defined above,

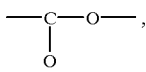

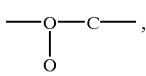

—CH$_2$—O—,
—O—CH$_2$—,
—CH$_2$—S(O)$_m$— wherein m is as defined above,
—S(O)$_m$—CH$_2$— wherein m is as defined above,

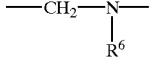

wherein $R^6$ is as defined above,

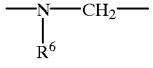

wherein $R^6$ is as defined above,
—CH=N—, or
—N=CH—;

with the proviso that when X is O, and $R^5$ is not NH—OR$^6$, at least one of R or $R^a$ is not hydrogen; and corresponding isomers thereof; or a pharmaceutically acceptable salt thereof.

Typical compounds from this class include:
4-Dibenzofuran-2-yl-4-hydroxylamino-butyric acid; 2-(2-Dibenzofuran-2-yl-2-hydroxylamino-ethyl)-4-methyl-pentanoic acid;
2-(2-Dibenzofuran-2-yl-2-hydroxylmino-ethyl)-5-phenyl-pentanoic acid;
4-Dibenzofuran-2-yl4-hydroxylmino-2-phenethyl-butyric acid;
5-(4-Chloro-phenyl)-2-(2-dibenzofuran-2-yl-2-hydroxylmino-ethyl)-pentanoic acid;
2-(2-Dibenzofuran-2-yl-2-hydroxylmino-ethyl)-5-(4-fluoro-phenyl)-pentanoic acid;
2-(2-Dibenzofuran-2-yl-2-hydroxylmino-ethyl)-5-(4-methoxy-phenyl)-pentanoic acid;
2-(2-Dibenzofuran-2-yl-2-hydroxylmino-ethyl)-5-β-tolyl-pentanoic acid;
3-(Dibenzofuran-2-yl-hydroxylmino-methyl)-5-methyl-hexanoic acid;
3-(Dibenzofuran-2-yl-hydroxylmino-methyl)-6-phenyl-hexanoic acid;
3-(Dibenzofuran-2-yl-hydroxylmino-methyl)-5-phenyl-pentanoic acid;
6-(4-Chloro-phenyl)-3-(dibenzofuran-2-yl-hydroxylmino-methyl)-hexanoic acid;
3-(Dibenzofuran-2-yl-hydroxylmino-methyl)-6-(4-fluoro-phenyl)-hexanoic acid;
3-(Dibenzofuran-2-yl-hydroxylmino-methyl)-6-(4-methoxyphenyl)-hexanoic acid; and
3-(Dibenzofuran-2-yl-hydroxylmino-methyl)-6-p-tolyl-hexanoic acid; and corresponding isomers thereof; or a pharmaceutically acceptable salt thereof.

Tricyclic butyric acids having an α-amino substituent are defined by the formula:

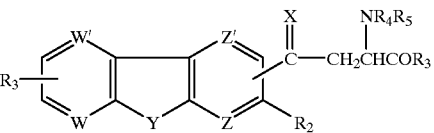

wherein

X is O, NOR$_9$, S, OH, SH, or

$R_7$ and $R^{7a}$ independently are
  hydrogen,
  $C_1$–$C_{20}$ alkyl or substituted $C_1$–$C_{20}$ alkyl,
  (CH$_2$)$_{0-6}$-aryl,
  (CH$_2$)$_{0-6}$-heteroaryl, or
  (CH$_2$)$_{0-6}$-cycloalkyl;
$R_1$ and $R_2$ independently are
  hydrogen,
  $C_1$–$C_{20}$ alkyl or substituted $C_1$–$C_{20}$ alkyl,
  halo,
  NO$_2$,
  CN,
  CHO,
  COR$_6$,
  COOR$_6$,
  SO$_3$R$_6$,
  OR$_6$,
  CONR$_4$R$_5$,
  (CH$_2$)$_{0-6}$-aryl,
  (CH$_2$)$_{0-6}$-heteroaryl, or
  (CH$_2$)$_{0-6}$-cycloalkyl;
$R_6$ is hydrogen,
  $C_1$–$C_{20}$ alkyl or substituted $C_1$–$C_{20}$ alkyl;
aryl is phenyl or substituted phenyl;
$R_3$ is hydroxy,
  O—$C_1$–$C_{20}$ alkyl or substituted O—$C_1$–$C_{20}$ alkyl,
  O—(CH$_2$)$_{1-3}$ aryl, or
  NHOR$_6$;
$R_4$ and $R_5$ independently are hydrogen,
  $C_1$–$C_{20}$ alkyl or substituted $C_1$–$C_{20}$ alkyl,
  (CH$_2$)$_{0-6}$-aryl,
  (CH$_2$)$_{0-6}$-heteroaryl; or one of $R_4$ and $R_5$ is hydrogen and the other is:
  COR$_8$,
  CSR$_8$,
  CONR$_8$R$_9$,
  CSNR$_8$R$_9$,

COOR₈,

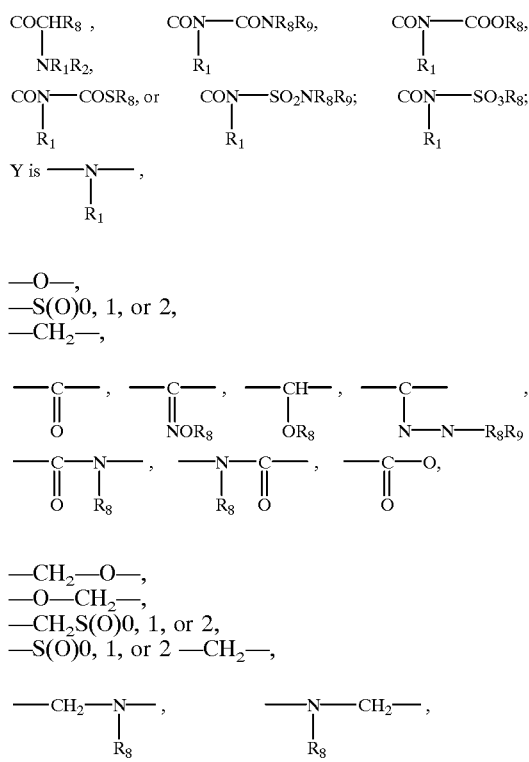

Y is —N—,
      |
      R₁

—O—,
—S(O)0, 1, or 2,
—CH₂—,

—CH₂—O—,
—O—CH₂—,
—CH₂S(O)0, 1, or 2,
—S(O)0, 1, or 2 —CH₂—,

—CH₂—N—,    —N—CH₂—,
     |           |
     R₈          R₈

—CH=N, or
—N=CH—;

R₈ and R₉ independently are
  hydrogen
  $C_1$–$C_{20}$ alkyl or substituted $C_1$–$C_{20}$ alkyl,
  $(CH_2)_{0-6}$-aryl,
  $(CH_2)_{0-6}$-heteroaryl, or
  $(CH_2)_{0-6}$-cycloalkyl;

W, W', Z, and Z' independently are $CR_1$ or N;
and the pharmaceutically acceptable salts, isomers, stereoisomers, and solvates thereof.

Specific examples of compounds to be employed in the present method include:
(S)-4-Dibenzofuran-2-yl-4-oxo-2-(2,2,2-trifluoroacetylamino)-butyric acid;
(R)-4-Dibenzofuran-2-yl-4-oxo-2-(2,2,2-trifluoroacetylamino)-butyric acid;
(S)-2-Amino-4-dibenzofuran-2-yl-4-oxo-butyric acid (S)-2-Acetylamino-4-dibenzofuran-2-yl-4-oxo-butyric;
(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]4-dibenzofuran-2-yl-4-oxo-butyric acid;
(S)-4-Dibenzofuran-2-yl-4-oxo-2-(dodecanoylamino)-butyric acid;
(S)-4-Dibenzofuran-2-yl-4-oxo-2-(dodecanoyl-amino)-butyric acid;
(S)-4-Dibenzofuran-2-yl-4-oxo-2-(2,2,2-trifluoroacetylamino)-butyric acid;
(R)4-Dibenzofuran-2-yl-4-oxo-2-(2,2,2-trifluoroacetylamino)-butyric acid;
(S)-2-Amino4-dibenzofuran-2-yl-4-oxo-butyric acid;
(S)-2-Acetylamino-4-dibenzofuran-2-yl-4-oxo-butyric acid;
(S)-4-Dibenzofuran-2-yl-2-[3-(2,6-diisopropyl-phenyl)-ureido]-4-oxo-butyric acid;
(S)-2-Benzoylamino-4-dibenzofuran-2-yl-4-oxo-butyric acid;
(S)-4-Dibenzofuran-2-yl-4-oxo-2-phenylacetylamino-butyric acid;
(S)-4-Dibenzofuran-2-yl-4-oxo-2-(3-phenyl-propionylamino)-butyric acid;
(S)-4-Dibenzofuran-2-yl-4-oxo-2-(7-phenyl-heptanoylamino)-butyric acid;
(S)-2-[(Biphenyl-4-carbonyl)-amino]-4-dibenzofuran-2-yl-4-oxo-butyric acid;
(S)4-Dibenzofuran-2-yl-4-oxo-2-(octanoylamino)-butyric acid; and
(S)-4-Dibenzofuran-2-yl-4-oxo-2-(dodecanoylamino)-butyric acid.

Tricyclic sulfonamide matrix metalloproteinase inhibitors include compounds of the formula

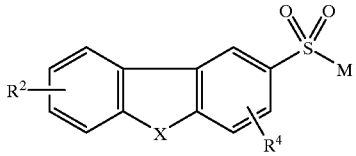

wherein M is a natural (L) alpha amino acid derivative having the structure

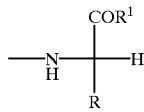

X is O, S, $S(O)_n$, $CH_2$, CO, or NH;
R is a side chain of a natural alpha amino acid;
$R^1$ is $C_1$–$C_5$ alkoxy, hydroxy, or —$NHOR^5$;
$R^2$ and $R^4$ are independently hydrogen, —$C_1$–$C_5$ alkyl, —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or
—$NHCOR^5$;
each $R^5$ and $R^6$ are independently hydrogen or $C_1$–$C_5$ alkyl; and
n is 0 to 2, and the pharmaceutically acceptable salts, ester, amides, and prodrugs thereof.

Specific compounds from this class to be employed include:
(L)-2-(Dibenzofuran-2-sulfonylamino)-4-methyl-pentanoic acid;
(L)-2-(Dibenzofuran-2-sulfonylamino)-3-methyl-pentanoic acid (L)-2-(Dibenzofuran-2-sulfonylamino)-3-phenyl-propionic acid;
(L)-2-(Dibenzofuran-2-sulfonylamino)-propionic acid;
(L)-2-(Dibenzofuran-2-sulfonylamino)-3-methyl-butyric acid;
(Dibenzofuran-2-sulfonylamino)-acetic acid;
(L)-2-(Dibenzofuran-2-sulfonylamino)-succinic acid;

(L)-2-(Dibenzofuran-2-sulfonylamino)-3-tritylsulfanyl-propionic acid;
(L)-2-(Dibenzofuran-2-sulfonylamino)-3-mercapto-propionic acid;
(L)-2-(Dibenzofuran-2-sulfonylamino)-3-methyl-pentanoic acid hydroxyamide;
(L)-2-(Dibenzofuran-2-sulfonylamino)-4-methyl-pentanoic acid;
(L)-2-(Dibenzofuran-2-sulfonylamino)-3-methyl-pentanoic acid;
(L)-2-(Dibenzofuran-2-sulfonylamino)-3-phenyl-propionic acid;
(L)-2-(Dibenzofuran-2-sulfonylamino)-propionic acid;
(L)-2-(Dibenzofuran-2-sulfonylamino)-3-methyl-butyric acid;
(Dibenzofuran-2-sulfonylamino)-acetic acid;
(L)-2-(Dibenzofuran-2-sulfonylamino)-succinic acid;
(L)-2-(Dibenzofuran-2-sulfonylamino)-3-tritylsulfanyl-propionic acid;
(L)-2-(Dibenzofuran-2-sulfonylamino)-3-mercapto-propionic acid; and
(L)-2-(Dibenzofuran-2-sulfonylamino)-3-methyl-pentanoic acid hydroxyamide.

Additional MMP inhibitors are defined by the formula:

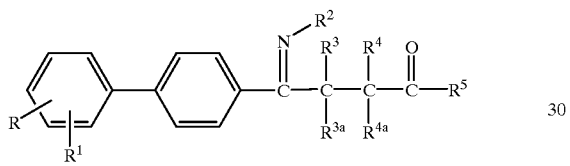

wherein
R and $R^1$ are the same of different and are
hydrogen,
alkyl,
halogen,
nitro,
cyano,
trifluoromethyl,
—$OR^6$ wherein $R^6$ is hydrogen,
  alkyl,
  aryl,
  arylalkyl,
  heteroaryl, or
  cycloalkyl,

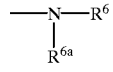

wherein $R^6$ and $R_{6a}$ are the same or different and are as defined above for $R^6$,

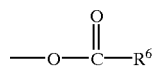

wherein $R^6$ is as defined above,

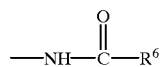

wherein $R^6$ is as defined above,

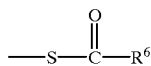

wherein $R^6$ is as defined above,
—$SR^6$ wherein $R^6$ is as defined above,

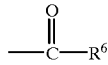

wherein $R^6$ is as defined above,
—$CH_2$—$OR^6$ wherein $R^6$ is as defined above,

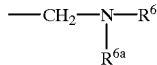

wherein $R^6$ and $R^{6a}$ are the same or different and are as defined above for $R^6$,

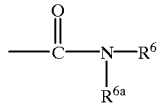

wherein $R^6$ and $R^{6a}$ are the same or different and are as defined above for $R^6$,

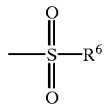

wherein
$R^6$ is as defined above, cycloalkyl, or
heteroaryl, with the proviso that R and $R^1$ are not both hydrogen;
$R^2$ is —$OR^6$ wherein $R^6$ is as defined above, or

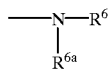

wherein
$R^6$ and $R^{6a}$ are the same or different and are as defined above for $R^6$;
$R^3$, $R^{3a}$, $R^4$, and $R^{4a}$ are the same or different and are
hydrogen,
fluorine,
alkyl,
—$(CH_2)_n$-aryl wherein n is an integer from 1 to 6,
—$(CH)_n$-heteroaryl wherein n is as defined above,
—$(CH_2)_n$-cycloalkyl wherein n is as defined above,
—$(CH_2)_p$—X—$(CH_2)_q$-aryl wherein X is O, S, SO, $SO_2$, or NH, and p and q are each zero or an integer of 1 to 6, and the sum of p+q is not greater than six,
—$(CH_2)_p$—X—$(CH_2)_q$-heteroaryl wherein X, p, and q are as defined above, or
—$(CH_2)_n$—$R^7$ wherein $R^7$ is
N-phthalimido,
N-2,3-naphthyimido, —OR$^6$ wherein R$^6$ is as defined above,

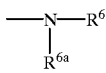

wherein R$^6$ and R$^{6a}$ are the same or different and are as defined above for R$^6$, —SR$^6$ where R$^6$ is as defined above,

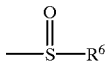

wherein R$^6$ is as defined above,

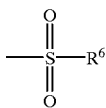

wherein R$^6$ is as defined above,

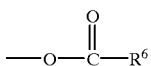

wherein R$^6$ is as defined above,

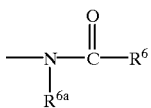

wherein R$^6$ and R$^{6a}$ are the same or different and as defined above for R$^6$,

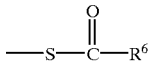

wherein R$^6$ is as defined above,

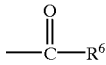

wherein R$^6$ is as defined above,

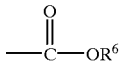

wherein R$^6$ is as defined above, or

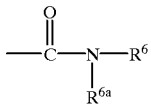

wherein R$^6$ and R$^{6a}$ are the same or different and are as defined above for R$^6$, and
n is as defined above;

R$^5$ is OH or SH; with the proviso that R$^3$, R$^{3a}$, R$^4$, and R$^{4a}$ are hydrogen or at least one of R$^3$, R$^{3a}$, R$^4$, or R$^{4a}$ is fluorine; and corresponding isomers thereof; or a pharmaceutically acceptable salt thereof.

Typical compounds from this class that are routinely utilized in the present method include:
4-(4'-Chloro-biphenyl-4-yl)-4-hydroxylmino-butyric acid;
4-(4'-Bromo-biphenyl4-yl)-4-hydroxylmino-butyric acid;
4-(4'-Chloro-biphenyl-4-yl)-4-(dimethylhydrazono)-butyric acid;
4-(4'-Fluoro-biphenyl4-yl)-4-hydroxylmino-butyric acid;
(±)-4-(4'-Chloro-biphenyl-4-yl)-4-hydroxy-butyric acid;
4-(4'-Bromo-2'-fluoro-biphenyl-4-yl)-4-hydroxylmino-butyric acid;
(±)-4-(4'-Chloro-biphenyl-4-yl)-3-fluoro-4-oxo-butyric acid;
4-(2',4'-Dichloro-biphenyl-4-yl)-4-hydroxylmino-butyric acid;
4-(2',4'-Difluoro-biphenyl4-yl)-4-hydroxylmino-butyric acid;
(±)-4-(4'-Chloro-biphenyl-4-yl)-4-hydroxylmino-2-fluoro-2-(3-phenylpropyl)-butyric acid;
(±)-4-(4'-Chloro-biphenyl-4-yl)-4-hydroxylmino-2-fluoro-2-(2-phenylethyl)-butyric acid;
(±)-4-(4'-Chloro-biphenyl-4-yl)-4-hydroxylmino-2-fluoro-2-(3-phthalimidopropyl)-butyric acid;
(±)-4-(4'-Chloro-biphenyl-4-yl)-4-hydroxylmino-2-fluoro-2-(phenylthiomethyl)-butyric acid;
4-(4'-Chloro-2'-fluoro-biphenyl-4-yl)-4-hydroxylmino-butyric acid;
4-Hydroxylmino-4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxylmino-butyric acid;
(±)-4-(4'-Chloro-biphenyl-4-yl)-4-hydroxylmino-2-fluoro-2-(1H-indol-3-yl)methyl-butyric acid;
(±)-4-(4'-Chloro-biphenyl-4-yl)-4-hydroxylmino-2-fluoro-2-methyl-butyric acid;
(±)-2-[2-(4'-Chloro-biphenyl-4-yl)-2-hydroxylminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxylmino-butyric acid;
(±)-2-[2-(4'-Chloro-biphenyl-4-yl)-2-hydroxylminoethyl]-6-(1,3-dioxo-1,3-dihydro-isoindol-2-yl)-2-fluoro-hexanoic acid;
(±)-4-(4'-Chloro-biphenyl-4-yl)-4-hydroxylmino-2-fluoro-2-[2-(phenylethylcarbamoyl)-ethyl]-butyric acid;
4-(4'-Chloro-biphenyl-4-yl)-3,3-difluoro-4-hydroxylmino-butyric acid;
(±)-4-(4'-Chloro-biphenyl-4-yl)-3,3-dimethyl-2-fluoro-4-hydroxylmino-butyric acid;
(±)-4-(4'-Chloro-biphenyl-4-yl)-2,2-dimethyl-3-fluoro-4-hydroxylmino-butyric acid;
4-(4'-Chloro-biphenyl-4-yl)-2,2-difluoro-4-hydroxylmino-butyric acid; and
4-(4'-Chloro-biphenyl-4-yl)-2,2,3,3-tetrafluoro-4-hydroxylmino-butyric acid.

A compound selected from the group consisting of:
4-(4'-Chloro-biphenyl-4-yl)-4-hydroxylmino-butyric acid;
4-(4'-Bromo-biphenyl-4-yl)-4-hydroxylmino-butyric acid;
4-(4'-Chloro-biphenyl-4-yl)-4-(dimethylhydrazono)-butyric acid;
4-(4'-Fluoro-biphenyl-4-yl)-4-hydroxylmino-butyric acid;
(±)-4-(4'-Chloro-biphenyl-4-yl)-4-hydroxy-butyric acid;

4-(4'-Bromo-2'-fluoro-biphenyl-4-yl)-4-hydroxylmino-butyric acid;
(±)-4-(4'-Chloro-biphenyl-4-yl)-3-fluoro-4-oxo-butyric acid;
4-(2',4'-Dichloro-biphenyl-4-yl)-4-hydroxylmino-butyric acid;
4-(2',4'-Difluoro-biphenyl-4-yl)-4-hydroxylmino-butyric acid;
(±)-4-(4'-Chloro-biphenyl-4-yl)-4-hydroxylmino-2-fluoro-2-(3-phenylpropyl)-butyric acid;
(±)-4-(4'-Chloro-biphenyl-4-yl)-4-hydroxylmino-2-fluoro-2-(2-phenylethyl)-butyric acid;
(±)-4-(4'-Chloro-biphenyl-4-yl)-4-hydroxylmino-2-fluoro-2-(3-phthalimidopropyl)-butyric acid;
(±)-4-(4'-Chloro-biphenyl-4-yl)-4-hydroxylmino-2-fluoro-2-(phenylthiomethyl)-butyric acid;
4-(4'-Chloro-2'-fluoro-biphenyl-4-yl)-4-hydroxylmino-butyric acid;
4-Hydroxylmino4-(4'-trifluoromethyl-biphenyl-4-yl)-butyric acid;
4-(4'-Chloro-biphenyl-4-yl)-4-methoxyimino-butyric acid;
(±)-4-(4'-Chloro-biphenyl-4-yl)-2-fluoro-2-[2-(1,3-dioxo-1,3-dihydro-isoindol-2-yl)-ethyl]-4-hydroxylmino-butyric acid;
(±)-4-(4'-Chloro-biphenyl-4-yl)-4-hydroxylmino-2-fluoro-2-(1H-indol-3-yl)methyl-butyric acid;
(±)-4-(4'-Chloro-biphenyl-4-yl)-4-hydroxylmino-2-fluoro-2-methyl-butyric acid;
(±)-2-[2-(4'-Chloro-biphenyl-4-yl)-2-hydroxylminoethyl]-2-fluoro-6-phenyl-hexanoic acid;
(±)-4-(4'-Chloro-biphenyl-4-yl)-2-fluoro-2-[2-(1,3-dioxo-1,3-dihydro-benzo[F]isoindol-2-yl)-ethyl]-4-hydroxylmino-butyric acid;
(±)-2-[2-(4'-Chloro-biphenyl-4-yl)-2-hydroxylminoethyl]-6-(1,3-dioxo-1,3-dihydro-isoindol-2-yl)-2-fluoro-hexanoic acid;
(±)-4-(4'-Chloro-biphenyl-4-yl)-4-hydroxylmino-2-fluoro-2-[2-(phenyl -ethylcarbamoyl)-ethyl]-butyric acid;
4-(4'-Chloro-biphenyl-4-yl)-3,3-difluoro-4-hydroxylmino-butyric acid;
(±)-4-(4'-Chloro-biphenyl-4-yl)-3,3-dimethyl-2-fluoro-4-hydroxylmino-butyric acid;
(±)-4-(4'-Chloro-biphenyl-4-yl)-2,2-dimethyl-3-fluoro-4-hydroxylmino-butyric acid;
4-(4'-Chloro-biphenyl-4-yl)-2,2-difluoro-4-hydroxylmino-butyric acid; and
4-(4'-Chloro-biphenyl-4-yl)-2,2,3,3-tetrafluoro-4-hydroxylmino-butyric acid.

Biphenyl sulfonamides are also particularly good in the present method. Such compounds include those of the formula:

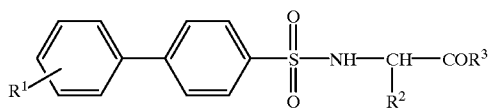

wherein:

$R^1$ is $C_1$–$C_6$ alkyl, halo, nitro, $NR^4R^5$, cyano, $OR^4$, and $COOR^4$;

$R^2$ is $C_1$–$C_6$ alkyl, optionally substituted by phenyl, substituted phenyl, $NR^4R^5$, $OR^6$, carboxy, carboxamido,

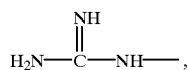

thio, methylthio, indole, imidazole, phthalimido, phenyl, and substituted phenyl;

$R^3$ is OH, $OC_1$–$C_6$ alkyl, or NHOH;

$R^4$ is hydrogen, $C_1$–$C_6$ alkyl, or $C_1$–$C_6$ alkanoyl;

$R^5$ is hydrogen or $C_1$–$C_6$ alkyl; and $R^6$ is hydrogen, $C_1$–$C_6$ alkyl, $C_1$–$C_6$ alkanoyl, phenyl, or substituted phenyl.

Specific compounds which can be employed include a compound of the above formula wherein $R^1$ is at the 4' position.

Another class of matrix metalloproteinase inhibitors useful in the present method are the heterocyclic substituted phenyl butyric acid derivatives, for example those defined by the formula:

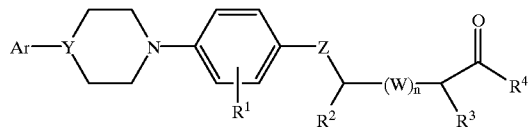

Ar is selected from phenyl,
  phenyl substituted with
    alkyl,
    $NO_2$,
    halogen,
    $OR^5$ wherein $R^5$ is hydrogen or alkyl,
    CN,
    $CO_2R^5$ wherein $R^5$ is as defined above,
    $SO_3R^5$ wherein $R^5$ is as defined above,
    CHO,
    $COR^5$ wherein $R^5$ is as defined above,
    $CONHR^5$ wherein $R^5$ is as defined above, or
    $NHCOR^5$ wherein $R^5$ is as defined above,
  2-naphthyl, or
  heteroaryl;

$R^1$ is selected from hydrogen,
  methyl,
  ethyl,
  $NO_2$,
  halogen,
  $OR^5$ wherein $R^5$ is as defined above,
  CN,
  $CO_2R^5$ wherein $R^5$ is as defined above,
  $SO_3R^5$ wherein $R^5$ is as defined above,
  CHO, or
  $COR^5$ wherein $R^5$ is as defined above;

$R^2$ and $R^3$ are the same or different and independently selected from hydrogen,
  alkyl,
  —$(CH_2)_v$-aryl wherein v is an integer from 1 to 5,
  —$(CH_2)_v$-heteroaryl wherein v is as defined above,
  —$(CH_2)_v$-cycloalkyl wherein v is as defined above,
  —$(CH_2)_p$—X—$(CH_2)_q$-aryl wherein X is O or S and p and q is each zero or an integer of 1 to 5, and the sum of p+q is not greater than an integer of 5,
  —$(CH_2)_p$—X—$(CH_2)_q$-heteroaryl wherein X, p, and q are as defined above,
  —$(CH_2)_tNR^6R^{6a}$, wherein t is zero or an integer of from 1 to 9 and $R^6$ and $R^{6a}$ are each the same or different and are as defined above for $R^5$, —$(CH_2)_vSR^5$, wherein v and $R^5$ are as defined above,
—$(CH_2)_vCO_2R^5$, wherein v and $R^5$ are as defined above, or
—$(CH_2)_vCONR^6R^{6a}$, wherein $R^6$ and $R^{6a}$ are the same or different and are as defined above for $R^5$ and v is as defined above;

$R^3$ is additionally —$(CH_2)_rR^7$ wherein r is an integer from 1 to 5 and $R^7$ is 1,3-dihydro-1,3-dioxo-2H-isoindol-2-yl, or 1,3,-dihydro-1,3-dioxo-benzo[f]isoindol-2-yl;

Y is CH or N;

Z is,

wherein $R^{10}$ is as defined above for $R^2$ and $R^3$, and is independently the same or different from $R^2$ and $R^3$ provided that
when Z is

then
$R^4$ must be OH,
C=O,
C=$NOR^5$ wherein $R^5$ is as defined above, or
C=N—$NR^6R^{6a}$ wherein $R^6$ and $R^{6a}$ are the same or different and are as defined above for $R^5$;

W is —$CHR^5$ wherein $R^5$ is as defined above;

n is zero or an integer of 1;

$R^4$ is OH,
$NR^6R^{6a}$ wherein $R^6$ and $R^{6a}$ are the same or different and are as defined above for $R^5$, when $R^4$ is $NR^6R^{6a}$ then Z must be C=O or
$NHOR^9$ wherein $R^9$ is hydrogen, alkyl, or benzyl; and corresponding isomers thereof; or a pharmaceutically acceptable salt thereof.

Especially preferred MMP inhibitors have the formula

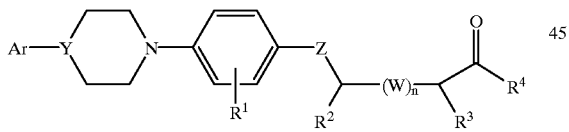

Ar is selected from phenyl,
phenyl substituted with
alkyl,
$NO_2$,
halogen,
$OR^5$ wherein $R^5$ is hydrogen or alkyl,
CN,
$CO_2R^5$ wherein $R^5$ is as defined above,
$SO_3R^5$ wherein $R^5$ is as defined above,
CHO,
$COR^5$ wherein $R^5$ is as defined above,
$CONHR^5$ wherein $R^5$ is as defined above, or
$NHCOR^5$ wherein $R^5$ is as defined above,
2-naphthyl, or
heteroaryl;

$R^1$ is selected from hydrogen,
methyl,
ethyl,
$NO_2$,
halogen,
$OR^5$ wherein $R^5$ is as defined above,
CN,
$CO_2R^5$ wherein $R^5$ is as defined above,
$SO_3R^5$ wherein $R^5$ is as defined above,
CHO, or
$COR^5$ wherein $R^5$ is as defined above;

$R^2$ and $R^3$ are the same or different and independently selected from hydrogen,
alkyl,
—$(CH_2)_v$-aryl wherein v is an integer from 1 to 5,
—$(CH_2)_v$-heteroaryl wherein v is as defined above,
—$(CH_2)_v$-cycloalkyl wherein v is as defined above,
—$(CH_2)_p$—X—$(CH_2)_q$-aryl wherein X is O or S and p and q is each zero or an integer of 1 to 5, and the sum of p+q is not greater than an integer of 5,
—$(CH_2)_p$—X—$(CH_2)_q$-heteroaryl wherein X, p, and q are as defined above,
—$(CH_2)_tNR^6R^{6a}$, wherein t is zero or an integer of from 1 to 9 and $R^6$ and $R^{6a}$ are each the same or different and are as defined above for $R^5$,
—$(CH_2)_vSR^5$, wherein v and $R^5$ are as defined above,
—$(CH_2)_vCO_2R^5$, wherein v and $R^5$ are as defined above, or
—$(CH_2)_vCONR^6R^{6a}$, wherein $R^6$ and $R^{6a}$ are the same or different and are as defined above for $R^5$ and v is as defined above;

$R^3$ is additionally —$(CH_2)_rR^7$ wherein r is an integer from 1 to 5 and $R^7$ is 1,3-dihydro-1,3-dioxo-2H-isoindol-2-yl, or 1,3,-dihydro-1,3-dioxo-benzo[f]isoindol-2-yl;

Y is CH or N;

Z is

wherein $R^{10}$ is as defined above for $R^2$ and $R^3$, and is independently the same or different from $R^2$ and $R^3$ provided that
when Z is

then
$R^4$ must be OH,
C=O,
C=$NOR^5$ wherein $R^5$ is as defined above, or
C=N—$NR^6R^{6a}$ wherein $R^6$ and $R^{6a}$ are the same or different and are as defined above for $R^5$;

W is —$CHR^5$ wherein $R^5$ is as defined above;

n is zero or an integer of 1;

$R^4$ is OH,
$NR^6R^{6a}$ wherein $R^6$ and $R^{6a}$ are the same or different and are as defined above for $R^5$, when $R^4$ is $NR^6R^{6a}$ then Z must be C=O or
$NHOR^9$ wherein $R^9$ is hydrogen, alkyl, or benzyl;
and corresponding isomers thereof; or a pharmaceutically acceptable salt thereof.

Preferred compounds to be employed include:
4-Oxo-4-[4-(4-phenyl-piperidin-1-yl)-phenyl]-butyric acid;

4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxylmino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazine-1-yl)-phenyl]-butyric acid; and
(±)3-Methyl-5-oxo-5-[4-(4-phenyl-piperidin-1-yl)-phenyl]-pentanoic acid.

A compound which is 4-oxo-4-[4-(4-phenyl-piperidin-1-yl)-phenyl]-butyric acid.

A compound according to claim 5 which is selected from the group consisting of:
4-Oxo-4-[4-(4-phenyl-piperidin.1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxylmino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid; and
(±)3-Methyl-5-oxo-5-[4-(4-phenyl-piperidin-1-yl)-phenyl]-pentanoic acid.

A compound which is 4-oxo-4-[4-(4-phenyl-piperidin-1-yl)-phenyl]-butyric acid.

Similar compounds which are sulfonamide derivatives have the formula:

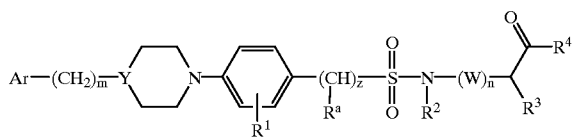

wherein:
Ar is selected from phenyl;
phenyl substituted with alkyl, —$NO_2$, halogen, —$OR^5$, —CN, —$CO_2R^5$, —$SO_3R^5$, —CHO, —$COR^5$, —$CONHR^5$, —$NHR^5$, or —$NHCOR^5$;
heteroaryl; or
2-naphthyl;
$R^1$ is hydrogen, methyl, —$NO_2$, —Cl, —$NH_2$, —$NHCO_2CH_3$, —OH, or —$CO_2H$;
$R^2$ and $R^3$ are the same or different and are independently selected from hydrogen, alkyl, —$(CH_2)_v$-aryl, —$(CH_2)_v$-heteroaryl, —$(CH_2)_v$-cycloalkyl, —$(CH_2)_p$—X—$(CH_2)_q$-aryl, —$(CH_2)_p$—X—$(CH_2)_q$-heteroaryl, —$(CH_2)_t NR^6R^{6a}$, —$(CH_2)_v R^7$, —$(CH_2)_v CO_2R^5$, —$(CH_2)_v CONR^6R^{6a}$, or —$(CH_2)_v SR^5$;
m is zero or 1;
Y is CH or N; provided that when m=1, Y does not=N;
z is zero or 1;
z is zero or 1;
W is —$CHR^8$;
n is zero or 1;
$R^4$ is —OH, —$NR^6R^{6a}$, or —$NHOR^9$;
$R^5$ is hydrogen or alkyl;
v is 1 to 5;
X is O or S;
p and q are independently 1 to 5, provided that p+q is not greater than 5;
t is 1 to 9;
$R^6$ and $R^{6a}$ are each the same or different and are hydrogen or alkyl;
$R^7$ is 1,3-dihydro-1,3-dioxo-2H-isoindol-2-yl, or 1,3-dihydro-1,3-dioxo-benzo[f]isoindol-2-yl;
$R^8$ is hydrogen or alkyl; and
$R^9$ is hydrogen, alkyl, or benzyl; or
a pharmaceutically acceptable salt thereof

| Tablet Formulation | |
|---|---|
| Ingredient | Amount (mg) |
| 2-(4'-bromobiphenyl-4-sulfonylamino)-3-methyl-butyric acid | 25 |
| Lactose | 50 |
| Corn starch (for mix) | 10 |
| Corn starch (paste) | 10 |
| Magnesium stearate (1%) | 5 |
| Total | 100 |

The biphenylsulfonamide, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four

| Preparation for Oral Solution | |
|---|---|
| Ingredient | Amount |
| (R)-2-(4'-Cyanobiphenyl-4-sulfonylamino)-3-phenyl-propionic acid sodium salt | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the biphenylsulfonamide is dissolved therein. The saccharin, sodium benzoate, flavor, and dye are added and dissolved. The volume is adjusted to 100 mL with distilled water. Each milliliter of syrup contains 4 mg of invention compound.

PARENTAL SOLUTION

In a solution of 700 mL of propylene glycol and 200 mL of water for injection is suspended 20 g of (S)-2-(4'-amino-biphenyl-4-sulfonylamino)-3-(3-ethoxyphenyl)-propionic acid. After suspension is complete, the pH is adjusted to 6.5 with 1N sodium hydroxide, and the volume is made up to 1000 mL with water for injection. The formulation is sterilized, filled into 5.0 mL ampoules each containing 2.0 mL, and sealed under nitrogen.

What is claimed is:
1. A method for treating a neurological disorder in a mammal, comprising:

administering to a mammal in need thereof an effective amount of a matrix metalloproteinase inhibitor, wherein the MMP inhibitor utilized is a compound of the formula

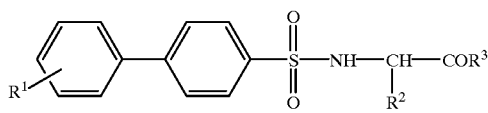

wherein:
R$^1$ is C$_1$–C$_6$ allyl, halo, nitro, NR$^4$R$^5$, cyano, OR$^4$, and COOR$^4$;
R$^2$ is C$_1$–C$_6$ alkyl, optionally substituted by phenyl, substituted phenyl, NR$^4$R$^5$, OR$^6$, carboxy, carboxamido,

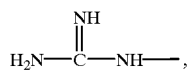

thio, methylthio, indole, imidazole, phthalimido, phenyl, and substituted phenyl;
R$^3$ is OH, OC$_1$–C$_6$ alkyl, or NHOH;
R$^4$ is hydrogen, C$_1$–C$_6$ alkyl, or C$_1$–C$_6$ alkanoyl;
R$^5$ is hydrogen or C$_1$–C$_6$ alkyl; and
R$^6$ is hydrogen, C$_1$–C$_6$ alkyl, C$_1$–C$_6$ alkanoyl, phenyl, or substituted phenyl.

2. The method of claim 1 wherein the neurological disorder is Alzheimer's disease.

3. The method of claim 1 wherein the neurological disorder is Huntington's disease.

4. The method of claim 1 wherein the neurological disorder is Parkinson's disease.

5. The method of claim 1 wherein the neurological disorder is amyotrophic lateral sclerosis.

6. The method of claim 1 employing 2-(4'-bromobiphenyl-4-(sulfonylamino)-3-methyl-butyric acid.

7. A method of promoting wound healing in a mammal, comprising:
administering to a mammal in need thereof an effective amount of a matrix metalloproteinase inhibitor, wherein the MMP inhibitor utilized is a compound of the formula

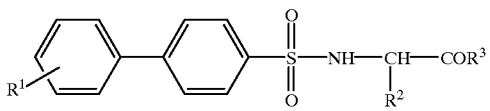

wherein:
R$^1$ is C$_1$–C$_6$ allyl, halo, nitro, NR$^4$R$^5$, cyano, OR$^4$, and COOR$^4$;
R$^2$ is C$_1$–C$_6$ alkyl, optionally substituted by phenyl, substituted phenyl, NR$^4$R$^5$, OR$^6$, carboxy, carboximido,

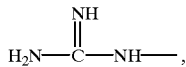

thio, methylthio, indole, imidazole, phthalimido, phenyl, and substituted phenyl;
R$^3$ is OH, OC$_1$–C$_6$ alkyl, or NHOH;
R$^4$ is hydrogen, C$_1$–C$_6$ alkyl, or C$_1$–C$_6$ alkanoyl;
R$^5$ is hydrogen or C$_1$–C$_6$ alkyl; and
R$_6$ is hydrogen, C$_1$–C$_6$ alkyl, C$_1$–C$_6$ alkanoyl, phenyl, or substituted phenyl.

8. The method of claim 7 wherein the MMP inhibitor utilized is 2-(4'-bromobiphenyl-4-sulfonylamino)-3-methyl-butyric acid.

* * * * *

UNITED STATES PATENT AND TRADEMARK OFFICE
CERTIFICATE OF CORRECTION

PATENT NO.     : 6,340,709 B1
DATED          : January 22, 2002
INVENTOR(S)    : Bocan et al.

It is certified that error appears in the above-identified patent and that said Letters Patent is hereby corrected as shown below:

Column 79,
Line 12, "$C_1$-$C_6$ allyl" should read -- $C_1$-$C_6$ alkyl --.

Column 80,
Line 16, "$C_1$-$C_6$ allyl" should read -- $C_1$-$C_6$ alkyl --.
Line 33, "$R_6$" should read -- $R^6$ --.

Signed and Sealed this

Eleventh Day of March, 2003

JAMES E. ROGAN
*Director of the United States Patent and Trademark Office*